(12) United States Patent
Hansen et al.

(10) Patent No.: US 12,012,450 B2
(45) Date of Patent: Jun. 18, 2024

(54) ANTI-NKG2A ANTIBODIES AND COMPOSITIONS

(71) Applicant: LES LABORATOIRES SERVIER, Suresnes (FR)

(72) Inventors: Randi Westh Hansen, Roskilde (DK); Franziska Katharina Uhlenbrock, Værløse (DK); Nikolaj Dietrich, Hellerup (DK); Anne Worsaae, Kongens Lyngby (DK); Michael Monrad Grandal, Ballerup (DK)

(73) Assignee: LES LABORATOIRES SERVIER, Suresnes (FR)

( * ) Notice: Subject to any disclaimer, the term of this patent is extended or adjusted under 35 U.S.C. 154(b) by 0 days.

(21) Appl. No.: 17/828,740

(22) Filed: May 31, 2022

(65) Prior Publication Data

US 2022/0389100 A1 Dec. 8, 2022

Related U.S. Application Data

(60) Provisional application No. 63/195,470, filed on Jun. 1, 2021.

(51) Int. Cl.
*C07K 16/28* (2006.01)
*A61K 45/06* (2006.01)
*A61P 35/00* (2006.01)

(52) U.S. Cl.
CPC .......... *C07K 16/2803* (2013.01); *A61K 45/06* (2013.01); *A61P 35/00* (2018.01); *C07K 2317/31* (2013.01); *C07K 2317/51* (2013.01); *C07K 2317/52* (2013.01); *C07K 2317/76* (2013.01); *C07K 2317/92* (2013.01)

(58) Field of Classification Search
CPC ............ C07K 16/2803; C07K 2317/31; C07K 2317/51; C07K 2317/52; C07K 2317/76; C07K 2317/92; C07K 2317/21; C07K 2317/71; C07K 2317/74; A61K 45/06; A61P 35/00
See application file for complete search history.

(56) References Cited

U.S. PATENT DOCUMENTS

| | | |
|---|---|---|
| 9,422,368 B2 | 8/2016 | Spee et al. |
| 10,329,348 B2 | 6/2019 | Andre et al. |
| 2020/0199226 A1 | 6/2020 | Bezman et al. |

FOREIGN PATENT DOCUMENTS

| | | |
|---|---|---|
| EP | 2374818 A1 | 10/2011 |
| WO | 2016/041947 A1 | 3/2016 |
| WO | 2016/062851 A1 | 4/2016 |
| WO | 2017/046774 A2 | 3/2017 |
| WO | 2017/178493 A1 | 10/2017 |
| WO | 2020/094071 A1 | 5/2020 |

OTHER PUBLICATIONS

Greenspan et al., "Defining epitopes: It's not as easy as it seems," Nat. Biotechnol. (1999) 17(10):936-7.
Huang et al., "Higher-Order Structure Characterization of NKG2A/CD94 Protein Complex and Anti-NKG2A Antibody Binding Epitopes by Mass Spectrometry-Based Protein Footprinting Strategies" J. Am. Soc. Mass Spectrom. (2021) 32(7):1567-1574.
Kaiser et al., "Structural basis for NKG2A/CD94 recognition of HLA-E," PNAS (2008) 105(18):6696-701.
Levy et al., "Cetuximab-mediated cellular cytotoxicity is inhibited by HLA-E membrane expression in colon cancer cells," Innate Immun. (2009) 15(2):91-100.

*Primary Examiner* — Nelson B Moseley, II
*Assistant Examiner* — Alyssa Rae Stonebraker
(74) *Attorney, Agent, or Firm* — Steptoe LLP; Z. Ying Li; Wyan-Ching M. Lee

(57) ABSTRACT

This invention relates to anti-NKG2A antibodies and methods of using them in enhancing immunity in a patient in need thereof and in treating cancer.

20 Claims, 19 Drawing Sheets

Specification includes a Sequence Listing.

ANTI-NKG2A ANTIBODIES AND COMPOSITIONS

CROSS-REFERENCE TO RELATED APPLICATIONS

This application claims priority from U.S. Provisional Patent Application 63/195,470, filed Jun. 1, 2021. The disclosure of that priority application is incorporated by reference in its entirety.

SEQUENCE LISTING

The instant application contains a Sequence Listing which has been submitted electronically in ASCII format and is hereby incorporated by reference in its entirety. The electronic copy of the Sequence Listing, created on May 30, 2022, is named 022675_WO065_SL.txt and is 43,564 bytes in size.

BACKGROUND OF THE INVENTION

NKG2 proteins are C-type lectin receptors that dimerize with CD94 at the cell surface. NKG2A is an inhibitory member of the family and is expressed on natural killer (NK) cells and a subset of $CD8^+$ T cells. Engagement of the NKG2A/CD94 heterodimer with the non-classical MHC class I molecule HLA-E causes phosphorylation of immunoreceptor tyrosine-based inhibitory motifs (ITIMs) in the cytoplasmic tail of NKG2A, resulting in inhibitory signal transmission and consequent inhibition of NK cell and T cell activation.

HLA-E is expressed on the cells of many solid tumors and hematological cancers. By overexpressing HLA-E, cancer cells may enhance inhibitory signal transduction by the NKG2A/CD94/HLA-E complex and thus obtain protection from the cytotoxic activity of NK cells and T cells, leading to poorer patient outcomes.

In view of the role of NKG2A in cancer, there is a need for new and improved anti-cancer therapies that target NKG2A.

SUMMARY OF THE INVENTION

The present disclosure provides anti-NKG2A antibodies that can enhance activation of NK cells and T cells. The antibodies can be used to stimulate the immune response of a patient in need thereof, for example, a patient having cancer or an immune deficiency. Also provided are pharmaceutical compositions comprising one or more of these antibodies, and use of the antibodies and pharmaceutical compositions for treatment of cancer. The antibodies and compositions described herein may be used in a method for treating cancer in a patient; may be used for the manufacture of a medicament for treating cancer in a patient; or may be for use in treating cancer in a patient. Compared to currently available treatments for such cancers, including antibody treatments, it is contemplated that the antibodies and compositions described herein may provide a superior clinical response either alone or in combination with another cancer therapeutic.

In some embodiments, the present disclosure provides an anti-NKG2A antibody or an antigen-binding portion thereof that competes or cross-competes for binding with or binds to the same epitope of human NKG2A as antibody 24208, 23765, 23686, 23566, 23925, or 24135. In certain embodiments, the anti-NKG2A antibody or antigen-binding portion is defined by the amino acid sequences of the six CDRs, heavy and light chain variable domains, or heavy and light chains of said antibody.

In some embodiments, the present disclosure provides an anti-NKG2A antibody or an antigen-binding portion thereof, wherein
a) the heavy chain of said antibody comprises:
   i) heavy chain complementarity determining regions (H-CDR)-1-3 comprising the amino acid sequences of SEQ ID NOs: 5-7, respectively;
   ii) a heavy chain variable domain (VH) comprising an amino acid sequence at least 90% identical to the amino acid sequence of SEQ ID NO: 3;
   iii) a VH comprising the amino acid sequence of SEQ ID NO: 3; or
   iv) a heavy chain (HC) comprising the amino acid sequences of SEQ ID NOs: 3 and 61; and
b) the light chain of said antibody comprises:
   i) light chain complementarity determining regions (L-CDR)-1-3 comprising the amino acid sequences of SEQ ID NOs: 8-10, respectively;
   ii) a light chain variable domain (VL) comprising an amino acid sequence at least 90% identical to the amino acid sequence of SEQ ID NO: 4;
   iii) a VL comprising the amino acid sequence of SEQ ID NO: 4; or
   iv) a light chain (LC) comprising the amino acid sequences of SEQ ID NOs: 4 and 62.

In some embodiments, the present disclosure provides an anti-NKG2A antibody or an antigen-binding portion thereof, wherein
a) the heavy chain of said antibody comprises:
   i) H-CDR-1-3 comprising the amino acid sequences of SEQ ID NOs: 15-17, respectively;
   ii) a VH comprising an amino acid sequence at least 90% identical to the amino acid sequence of SEQ ID NO: 13;
   iii) a VH comprising the amino acid sequence of SEQ ID NO: 13; or
   iv) an HC comprising the amino acid sequences of SEQ ID NOs: 13 and 61; and
b) the light chain of said antibody comprises:
   i) L-CDR-1-3 comprising the amino acid sequences of SEQ ID NOs: 18-20, respectively;
   ii) a VL comprising an amino acid sequence at least 90% identical to the amino acid sequence of SEQ ID NO: 14;
   iii) a VL comprising the amino acid sequence of SEQ ID NO: 14; or
   iv) an LC comprising the amino acid sequences of SEQ ID NOs: 14 and 62.

In some embodiments, the present disclosure provides an anti-NKG2A antibody or an antigen-binding portion thereof, wherein
a) the heavy chain of said antibody comprises:
   i) H-CDR-1-3 comprising the amino acid sequences of SEQ ID NOs: 25-27, respectively;
   ii) a VH comprising an amino acid sequence at least 90% identical to the amino acid sequence of SEQ ID NO: 23;
   iii) a VH comprising the amino acid sequence of SEQ ID NO: 23; or
   iv) an HC comprising the amino acid sequences of SEQ ID NOs: 23 and 61; and
b) the light chain of said antibody comprises:
   i) L-CDR-1-3 comprising the amino acid sequences of SEQ ID NOs: 28-30, respectively;

ii) a VL comprising an amino acid sequence at least 90% identical to the amino acid sequence of SEQ ID NO: 24;
iii) a VL comprising the amino acid sequence of SEQ ID NO: 24; or
iv) an LC comprising the amino acid sequences of SEQ ID NOs: 24 and 62.

In some embodiments, the present disclosure provides an anti-NKG2A antibody or an antigen-binding portion thereof, wherein
a) the heavy chain of said antibody comprises:
   i) H-CDR-1-3 comprising the amino acid sequences of SEQ ID NOs: 35-37, respectively;
   ii) a VH comprising an amino acid sequence at least 90% identical to the amino acid sequence of SEQ ID NO: 33;
   iii) a VH comprising the amino acid sequence of SEQ ID NO: 33; or
   iv) an HC comprising the amino acid sequences of SEQ ID NOs: 33 and 61; and
b) the light chain of said antibody comprises:
   i) L-CDR-1-3 comprising the amino acid sequences of SEQ ID NOs: 38-40, respectively;
   ii) a VL comprising an amino acid sequence at least 90% identical to the amino acid sequence of SEQ ID NO: 34;
   iii) a VL comprising the amino acid sequence of SEQ ID NO: 34; or
   iv) an LC comprising the amino acid sequences of SEQ ID NOs: 34 and 62.

In some embodiments, the present disclosure provides an anti-NKG2A antibody or an antigen-binding portion thereof, wherein
a) the heavy chain of said antibody comprises:
   i) H-CDR-1-3 comprising the amino acid sequences of SEQ ID NOs: 45-47, respectively;
   ii) a VH comprising an amino acid sequence at least 90% identical to the amino acid sequence of SEQ ID NO: 43;
   iii) a VH comprising the amino acid sequence of SEQ ID NO: 43; or
   iv) an HC comprising the amino acid sequences of SEQ ID NOs: 43 and 61; and
b) the light chain of said antibody comprises:
   i) L-CDR-1-3 comprising the amino acid sequences of SEQ ID NOs: 48-50, respectively;
   ii) a VL comprising an amino acid sequence at least 90% identical to the amino acid sequence of SEQ ID NO: 44;
   iii) a VL comprising the amino acid sequence of SEQ ID NO: 44; or
   iv) an LC comprising the amino acid sequences of SEQ ID NOs: 44 and 62.

In some embodiments, the present disclosure provides an anti-NKG2A antibody or an antigen-binding portion thereof, wherein
a) the heavy chain of said antibody comprises:
   i) H-CDR-1-3 comprising the amino acid sequences of SEQ ID NOs: 55-57, respectively;
   ii) a VH comprising an amino acid sequence at least 90% identical to the amino acid sequence of SEQ ID NO: 53;
   iii) a VH comprising the amino acid sequence of SEQ ID NO: 53; or
   iv) an HC comprising the amino acid sequences of SEQ ID NOs: 53 and 61; and
b) the light chain of said antibody comprises:
   i) L-CDR-1-3 comprising the amino acid sequences of SEQ ID NOs: 58-60, respectively;
   ii) a VL comprising an amino acid sequence at least 90% identical to the amino acid sequence of SEQ ID NO: 54;
   iii) a VL comprising the amino acid sequence of SEQ ID NO: 54; or
   iv) an LC comprising the amino acid sequences of SEQ ID NOs: 54 and 62.

The present disclosure also provides isolated nucleic acid molecules, vectors, and host cells comprising nucleotide sequences that encode the heavy chain or an antigen-binding portion thereof, the light chain or an antigen-binding portion thereof, or both, of an anti-NKG2A antibody or antigen-binding portion described herein. Further, the present disclosure provides methods for producing an anti-NKG2A antibody or antigen-binding portion described herein by culturing said host cells, as well as methods for producing an antibody composition by admixing antibodies or antigen-binding portions described herein.

Other features, objectives, and advantages of the invention are apparent in the detailed description that follows. It should be understood, however, that the detailed description, while indicating embodiments and aspects of the invention, is given by way of illustration only, not limitation. Various changes and modifications within the scope of the invention will become apparent to those skilled in the art from the detailed description.

DETAILED DESCRIPTION OF THE INVENTION

Figure 1:
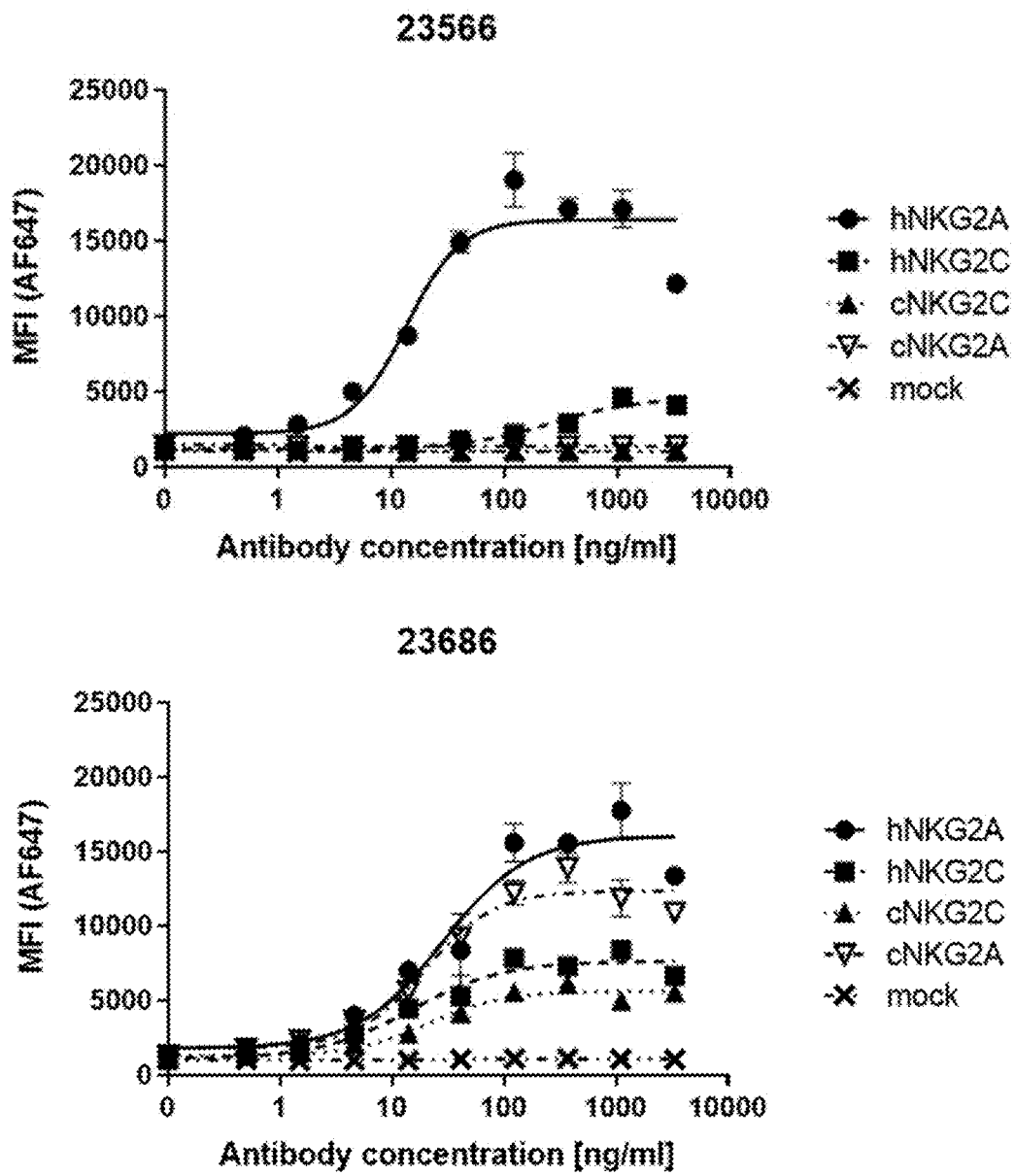
FIG. 1 is a set of graphs showing the binding profiles of six anti-human NKG2A antibodies, a reference antibody, and a control antibody to human and cynomolgus NKG2A and NKG2C expressed on transiently transfected CHO-C cells. Antibody binding was measured by flow cytometry (MFI: mean fluorescence intensity).
Figure 1:
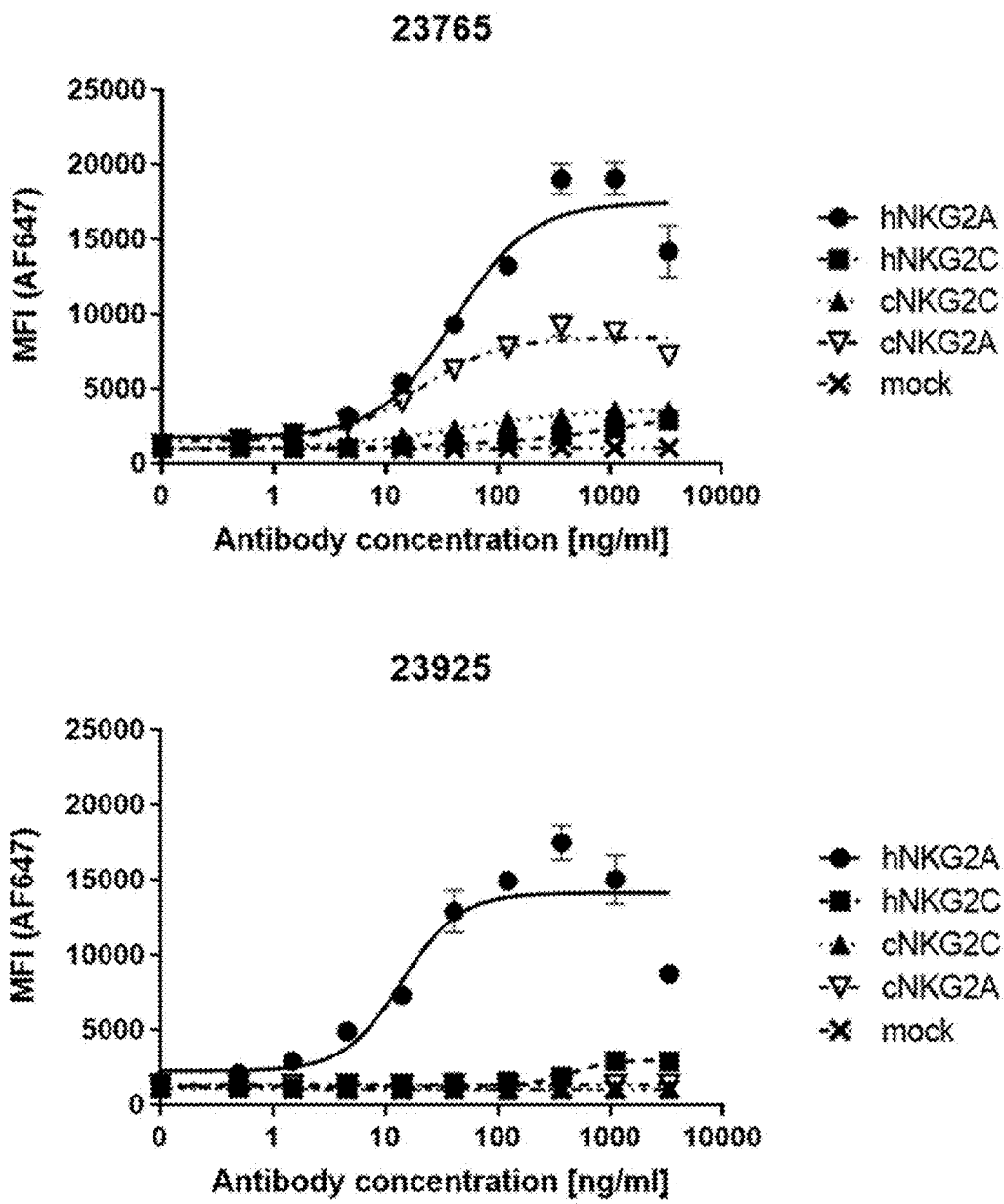
Figure 1:
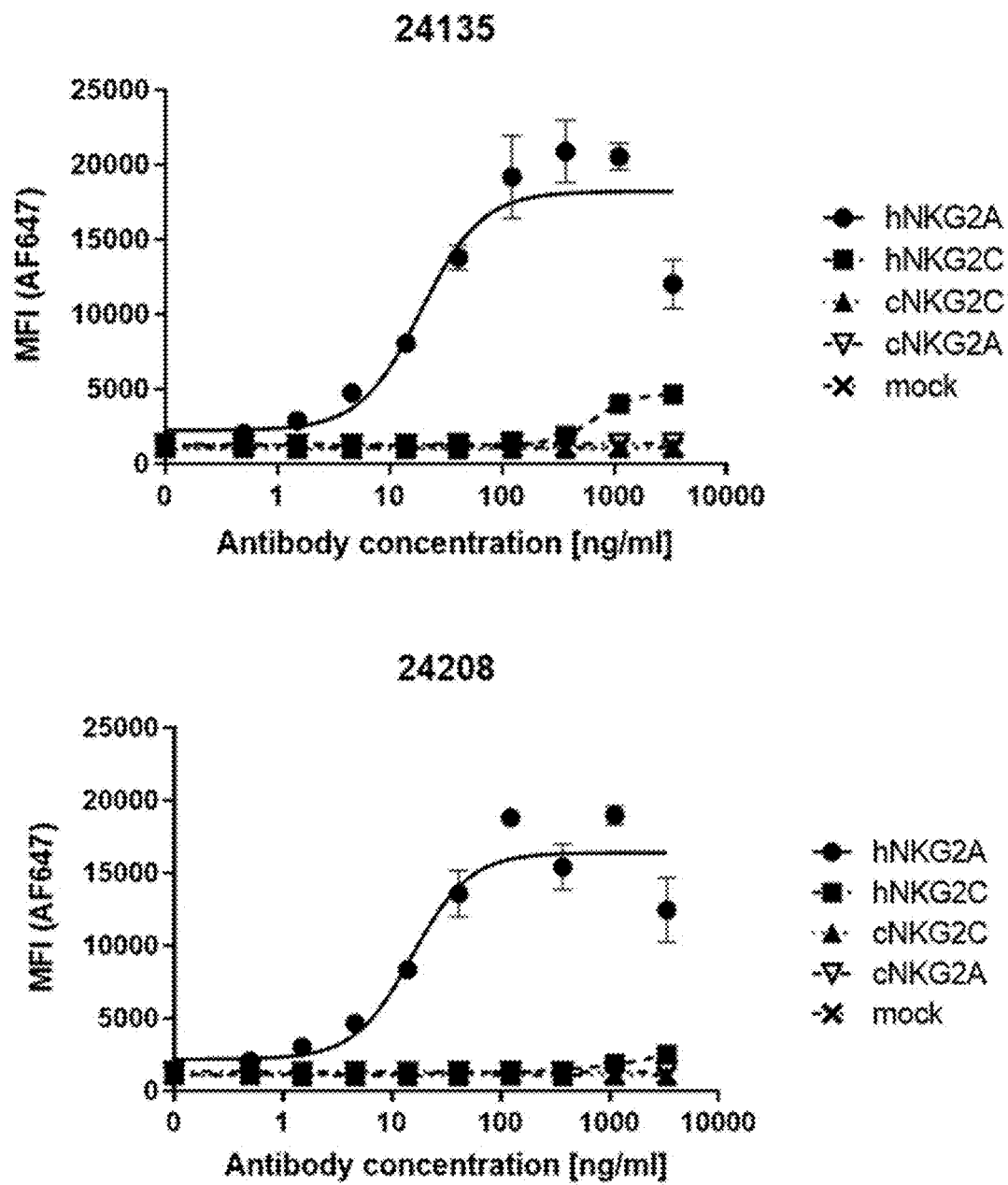
Figure 1:
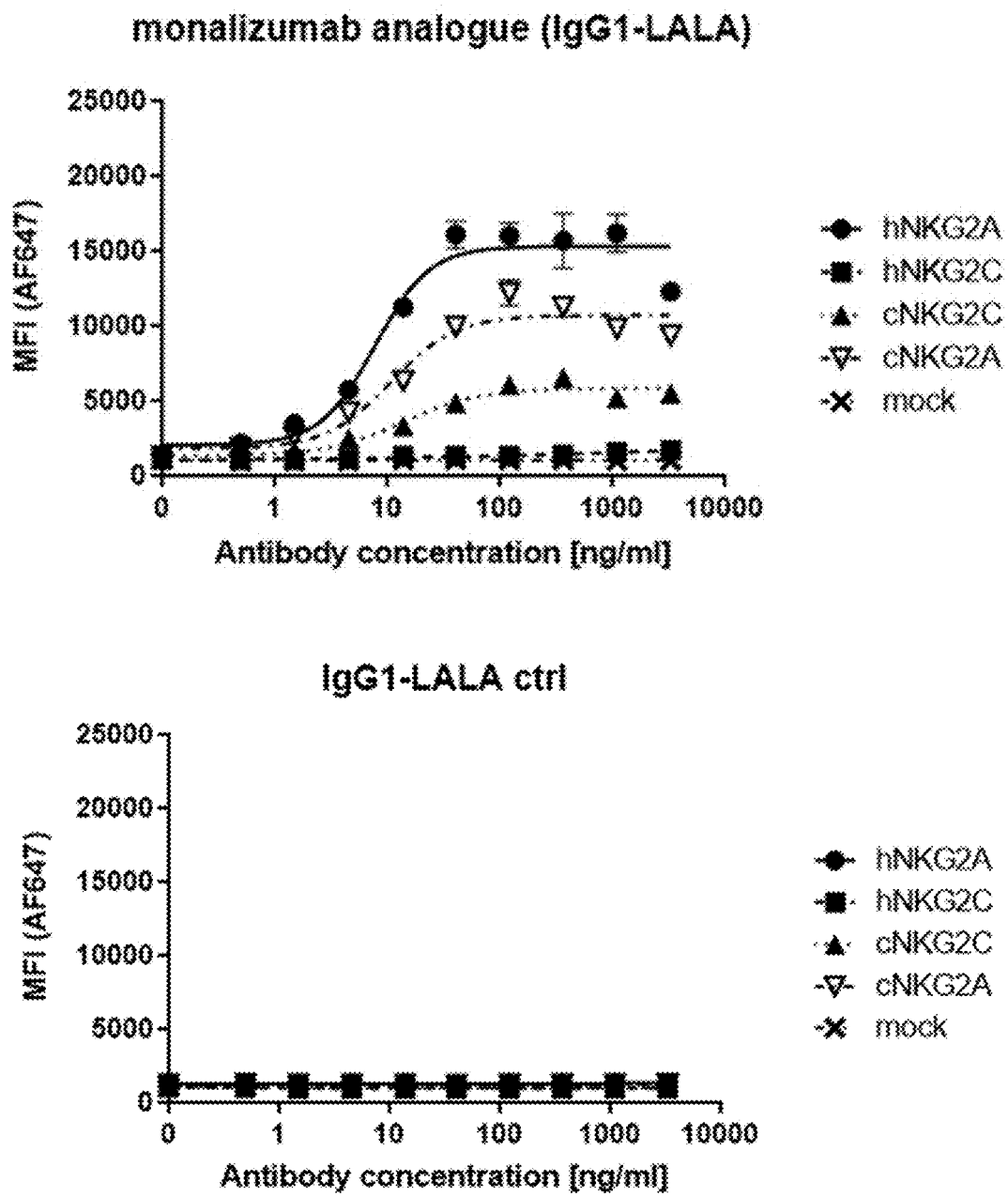

The present disclosure provides new antagonistic anti-human NKG2A antibodies that can be used to inhibit NKG2A activity in a patient, such as a cancer patient. Unless otherwise stated, as used herein, "NKG2A" refers to human NKG2A. A human NKG2A polypeptide sequence is available under UniProt Accession No. P26715 (NKG2A_HUMAN) (SEQ ID NO: 63), as shown below:

```
         10         20         30         40
MDNQGVIYSD LNLPPNPKRQ QRKPKGNKNS ILATEQEITY 50         60         70         80
AELNLQKASQ DFQGNDKTYH CKDLPSAPEK LIVGILGIIC 90        100        110        120
LILMASVVTI VVIPSTLIQR HNNSSLNTRT QKARHCGHCP 130        140        150        160
EEWITYSNSC YYIGKERRTW EESLLACTSK NSSLLSIDNE 170        180        190        200
EEMKFLSIIS PSSWIGVFRN SSHHPWVTMN GLAFKHEIKD 210        220        230
SDNAELNCAV LQVNRLKSAQ CGSSIIYHCK HKL
```

The term "antibody" (Ab) or "immunoglobulin" (Ig), as used herein, refers to a tetramer comprising two heavy (H) chains (about 50-70 kDa) and two light (L) chains (about 25 kDa) inter-connected by disulfide bonds. Each heavy chain is comprised of a heavy chain variable domain (VH) and a heavy chain constant region (CH). Each light chain is composed of a light chain variable domain (VL) and a light chain constant region (CL). The VH and VL domains can be subdivided further into regions of hypervariability, termed "complementarity determining regions" (CDRs), interspersed with regions that are more conserved, termed "framework regions" (FRs). Each VH and VL is composed of three CDRs (H-CDR herein designates a CDR from the heavy chain; and L-CDR herein designates a CDR from the light chain) and four FRs, arranged from amino-terminus to carboxyl-terminus in the following order: FR1, CDR1, FR2, CDR2, FR3, CDR3, FR4. The assignment of amino acid numbers, and of FR and CDR regions, in the heavy or light chain may be in accordance with IMGT® definitions (Eu numbering; Lefranc et al., *Dev Comp Immunol* 27(1):55-77 (2003)); or the definitions of Kabat, *Sequences of Proteins of Immunological Interest* (National Institutes of Health, Bethesda, MD (1987 and 1991)); Chothia & Lesk, *J. Mol. Biol.* 196:901-917 (1987); Chothia et al., Nature 342:878-883 (1989); MacCallum et al., *J. Mol. Biol.* 262:732-745 (1996); or Honegger and Plückthun, *J. Mol. Biol.* 309(3): 657-70 (2001).

The term "recombinant antibody" refers to an antibody that is expressed from a cell or cell line comprising the nucleotide sequence(s) that encode the antibody, wherein said nucleotide sequence(s) are not naturally associated with the cell.

The term "isolated protein," "isolated polypeptide" or "isolated antibody" refers to a protein, polypeptide or antibody that by virtue of its origin or source of derivation (1) is not associated with naturally associated components that accompany it in its native state, (2) is free of other proteins from the same species, (3) is expressed by a cell from a different species, and/or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "affinity" refers to a measure of the attraction between an antigen and an antibody. The intrinsic attractiveness of the antibody for the antigen is typically expressed as the binding affinity equilibrium constant ($K_D$) of a particular antibody-antigen interaction. An antibody is said to specifically bind to an antigen when the $K_D$ for the binding is ≤1 µM, e.g., ≤100 nM or ≤10 nM. A $K_D$ binding affinity constant can be measured, e.g., by surface plasmon resonance (BIAcore™) using the IBIS MX96 SPR system from IBIS Technologies or the Carterra LSA SPR platform, or by Bio-Layer Interferometry, for example using the Octet™ system from ForteBio.

The term "epitope" as used herein refers to a portion (determinant) of an antigen that specifically binds to an antibody or a related molecule such as a bi-specific binding molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. For example, an antibody to a linear epitope may be generated, e.g., by immunizing an animal with a peptide having the amino acid residues of the linear epitope. An antibody to a conformational epitope may be generated, e.g., by immunizing an animal with a mini-domain containing the relevant amino acid residues of the conformational epitope. An antibody to a particular epitope can also be generated, e.g., by immunizing an animal with the target molecule of interest (e.g., NKG2A) or a relevant portion thereof, then screening for binding to the epitope.

One can determine whether an antibody binds to the same epitope as or competes for binding with an anti-NKG2A antibody of the present disclosure by using methods known in the art, including, without limitation, competition assays, epitope binning, and alanine scanning. In some embodiments, one allows the anti-NKG2A antibody of the present disclosure to bind to NKG2A under saturating conditions, and then measures the ability of the test antibody to bind to NKG2A. If the test antibody is able to bind to NKG2A at the same time as the reference anti-NKG2A antibody, then the test antibody binds to a different epitope than the reference anti-NKG2A antibody. However, if the test antibody is not able to bind to NKG2A at the same time, then the test antibody binds to the same epitope, an overlapping epitope, or an epitope that is in close proximity to the epitope bound by the anti-NKG2A antibody of the present disclosure. This experiment can be performed using, e.g., ELISA, RIA, BIACORE™ SPR, Bio-Layer Interferometry or flow cytometry. To test whether an anti-NKG2A antibody cross-competes with another anti-NKG2A antibody, one may use the competition method described above in two directions, i.e., determining if the known antibody blocks the test antibody and vice versa. Such cross-competition experiments may be performed, e.g., using an IBIS MX96 or Carterra LSA SPR instrument or the Octet™ system.

The term "human antibody" refers to an antibody in which the variable domain and constant region sequences are derived from human sequences. The term encompasses antibodies with sequences that are derived from human genes but have been modified, e.g., to decrease immunogenicity, increase affinity, and/or increase stability. Further, the term encompasses antibodies produced recombinantly in nonhuman cells, which may impart glycosylation not typical of human cells. The term also encompasses antibodies produced in transgenic nonhuman organisms with human antibody genes (e.g., OmniRat® rats).

The term "antigen-binding portion" of an antibody (or simply "antibody portion"), as used herein, refers to one or more portions or fragments of an antibody that retain the ability to specifically bind to an antigen (e.g., human NKG2A, or a portion thereof). It has been shown that certain fragments of a full-length antibody can perform the antigen-binding function of the antibody. Examples of binding fragments encompassed within the term "antigen-binding portion" include (i) a Fab fragment: a monovalent fragment consisting of the VL, VH, CL and CH1 domains; (ii) a F(ab')2 fragment: a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated complementarity determining region (CDR) capable of specifically binding to an antigen. Furthermore, although the two domains of the Fv fragment, VL and VH, are encoded by separate genes, they can be joined, using recombinant methods, by a synthetic linker that enables them to be made as a single protein chain in which the VL and VH domains pair to form monovalent molecules (known as single chain Fv (scFv)). Also within the present disclosure are antigen-binding molecules comprising a VH and/or a VL. In the case of a VH, the molecule may also comprise one or more of a CH1, hinge, CH2, or CH3 region. Such single chain antibodies are also intended to be encompassed within the term "antigen-binding portion" of an antibody. Other forms of single chain antibodies, such as diabodies, are also encompassed. Diabodies are bivalent, bi-specific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites.

Antibody portions, such as Fab and F(ab')2 fragments, can be prepared from whole antibodies using conventional techniques, such as papain or pepsin digestion of whole antibodies. Moreover, antibodies, antibody portions and immunoadhesin molecules can be obtained using standard recombinant DNA techniques, e.g., as described herein.

The class (isotype) and subclass of anti-NKG2A antibodies may be determined by any method known in the art. In general, the class and subclass of an antibody may be determined using antibodies that are specific for a particular class and subclass of antibody. Such antibodies are available commercially. The class and subclass can be determined by ELISA or Western blot as well as other techniques. Alternatively, the class and subclass may be determined by sequencing all or a portion of the constant regions of the heavy and/or light chains of the antibodies, comparing their amino acid sequences to the known amino acid sequences of various classes and subclasses of immunoglobulins, and determining the class and subclass of the antibodies.

Unless otherwise indicated, all antibody amino acid residue numbers referred to in this disclosure are those under the IMGT® numbering scheme (EU numbering).

Anti-NKG2A Antibodies

The present disclosure provides antibodies directed against NKG2A, and antigen-binding portions thereof. In a particular aspect, the antibodies disclosed herein are human antibodies generated from transgenic animals (e.g., rats) that are able to produce antibodies encoded by rearranged human antibody genes. In certain embodiments, the human antibodies may contain certain mutations, e.g., to change primer-derived mutations back to the germ line sequence (see, e.g., the "Symplex-corrected" variant sequences in Table 1).

In some embodiments, the anti-NKG2A antibodies of the present disclosure have the "LALA" mutations (L234A/L235A) in the Fc region. These mutations hinder the antibodies' binding to human FcγR (Fc gamma receptors). Such antibodies are advantageous because they have a low level of secondary effector functions and hence do not deplete effector T cells or target other non-malignant cells.

In some embodiments, the anti-NKG2A antibody or antigen-binding portion competes or cross-competes for binding to human NKG2A with, or binds to the same epitope of human NKG2A as, an antibody comprising:

a) a heavy chain (HC) comprising the amino acid sequences of SEQ ID NOs: 3 and 61 and a light chain (LC) comprising the amino acid sequences of SEQ ID NOs: 4 and 62;

b) an HC comprising the amino acid sequences of SEQ ID NOs: 13 and 61 and an LC comprising the amino acid sequences of SEQ ID NOs: 14 and 62;

c) an HC comprising the amino acid sequences of SEQ ID NOs: 23 and 61 and an LC comprising the amino acid sequences of SEQ ID NOs: 24 and 62;

d) an HC comprising the amino acid sequences of SEQ ID NOs: 33 and 61 and an LC comprising the amino acid sequences of SEQ ID NOs: 34 and 62;

e) an HC comprising the amino acid sequences of SEQ ID NOs: 43 and 61 and an LC comprising the amino acid sequences of SEQ ID NOs: 44 and 62; or
f) an HC comprising the amino acid sequences of SEQ ID NOs: 53 and 61 and an LC comprising the amino acid sequences of SEQ ID NOs: 54 and 62.

In some embodiments, the anti-NKG2A antibody or antigen-binding portion has a heavy chain CDR3 (H-CDR3) amino acid sequence of SEQ ID NO: 7, 17, 27, 37, 47, or 57.

In some embodiments, the anti-NKG2A antibody or antigen-binding portion has heavy chain CDR1-3 (H-CDR1-3) comprising the amino acid sequences of SEQ ID NOs: 5-7, 15-17, 25-27, 35-37, 45-47, or 55-57, respectively.

In some embodiments, the anti-NKG2A antibody or antigen-binding portion has a heavy chain variable domain (VH) amino acid sequence that is at least 80%, 85%, 90%, 91%, 92%, 93%, 94%, 95%, 96%, 97%, 98%, or 99% A identical to the amino acid sequence of SEQ ID NO: 3, 13, 23, 33, 43, or 53.

In some embodiments, the anti-NKG2A antibody or antigen-binding portion has a VH comprising the amino acid sequence of SEQ ID NO: 3, 13, 23, 33, 43, or 53.

In some embodiments, the anti-NKG2A antibody has a VH amino acid sequence that is at least 80%, 85%, 90%, 91%, 92%, 93%, 94%, 95%, 96%, 97%, 98%, or 99% identical to the amino acid sequence of SEQ ID NO: 3, 13, 23, 33, 43, or 53; and a heavy chain constant region amino acid sequence that is at least 80%, 85%, 90%, 91%, 92%, 93%, 94%, 95%, 96%, 97%, 98%, or 99% A identical to the amino acid sequence of SEQ ID NO: 61.

In some embodiments, the anti-NKG2A antibody comprises a VH amino acid sequence of SEQ ID NO: 3, 13, 23, 33, 43, or 53 and a heavy chain constant region amino acid sequence of SEQ ID NO: 61.

In some embodiments, the anti-NKG2A antibody or antigen-binding portion has a light chain CDR3 (L-CDR3) amino acid sequence of SEQ ID NO: 10, 20, 30, 40, 50, or 60.

In some embodiments, the anti-NKG2A antibody or antigen-binding portion has light chain CDR1-3 (L-CDR1-3) comprising the amino acid sequences of SEQ ID NOs: 8-10, 18-20, 28-30, 38-40, 48-50, or 58-60, respectively.

In some embodiments, the anti-NKG2A antibody or antigen-binding portion has a light chain variable domain (VL) amino acid sequence that is at least 80%, 85%, 90%, 91%, 92%, 93%, 94%, 95%, 96%, 97%, 98%, or 99% identical to the amino acid sequence of SEQ ID NO: 4, 14, 24, 34, 44, or 54.

In some embodiments, the anti-NKG2A antibody or antigen-binding portion has a VL comprising the amino acid sequence of SEQ ID NO: 4, 14, 24, 34, 44, or 54.

In some embodiments, the anti-NKG2A antibody has a VL amino acid sequence that is at least 80%, 85%, 90%, 91%, 92%, 93%, 94%, 95%, 96%, 97%, 98%, or 99% identical to the amino acid sequence of SEQ ID NO: 4, 14, 24, 34, 44, or 54; and a light chain constant region amino acid sequence that is at least 80%, 85%, 90%, 91%, 92%, 93%, 94%, 95%, 96%, 97%, 98%, or 99% identical to the amino acid sequence of SEQ ID NO: 62.

In some embodiments, the anti-NKG2A antibody comprises a VL amino acid sequence of SEQ ID NO: 4, 14, 24, 34, 44, or 54 and a light chain constant region amino acid sequence of SEQ ID NO: 62.

In certain embodiments, the anti-NKG2A antibody comprises any one of the above-described heavy chains and any one of the above-described light chains.

In some embodiments, the anti-NKG2A antibody or antigen-binding portion of the present disclosure comprises the H-CDR1-3 and L-CDR1-3 amino acid sequences of:
a) SEQ ID NOs: 5-10, respectively;
b) SEQ ID NOs: 15-20, respectively;
c) SEQ ID NOs: 25-30, respectively;
d) SEQ ID NOs: 35-40, respectively;
e) SEQ ID NOs: 45-50, respectively; or
f) SEQ ID NOs: 55-60, respectively.

In some embodiments, the anti-NKG2A antibody or antigen-binding portion of the present disclosure comprises a VH and a VL that are 80%, 85%, 90%, 91%, 92%, 93%, 94%, 95%, 96%, 97%, 98%, or 99% identical (e.g., 90% identical) to the amino acid sequences of:
a) SEQ ID NOs: 3 and 4, respectively;
b) SEQ ID NOs: 13 and 14, respectively;
c) SEQ ID NOs: 23 and 24, respectively;
d) SEQ ID NOs: 33 and 34, respectively;
e) SEQ ID NOs: 43 and 44, respectively; or
f) SEQ ID NOs: 53 and 54, respectively.

In some embodiments, the anti-NKG2A antibody or antigen-binding portion of the present disclosure comprises a VH and a VL that comprise the amino acid sequences of:
a) SEQ ID NOs: 3 and 4, respectively;
b) SEQ ID NOs: 13 and 14, respectively;
c) SEQ ID NOs: 23 and 24, respectively;
d) SEQ ID NOs: 33 and 34, respectively;
e) SEQ ID NOs: 43 and 44, respectively; or
f) SEQ ID NOs: 53 and 54, respectively.

In some embodiments, the anti-NKG2A antibody of the present disclosure comprises:
a) a heavy chain (HC) comprising the amino acid sequences of SEQ ID NOs: 3 and 61 and a light chain (LC) comprising the amino acid sequences of SEQ ID NOs: 4 and 62;
b) an HC comprising the amino acid sequences of SEQ ID NOs: 13 and 61 and an LC comprising the amino acid sequences of SEQ ID NOs: 14 and 62;
c) an HC comprising the amino acid sequences of SEQ ID NOs: 23 and 61 and an LC comprising the amino acid sequences of SEQ ID NOs: 24 and 62;
d) an HC comprising the amino acid sequences of SEQ ID NOs: 33 and 61 and an LC comprising the amino acid sequences of SEQ ID NOs: 34 and 62;
e) an HC comprising the amino acid sequences of SEQ ID NOs: 43 and 61 and an LC comprising the amino acid sequences of SEQ ID NOs: 44 and 62; or
f) an HC comprising the amino acid sequences of SEQ ID NOs: 53 and 61 and an LC comprising the amino acid sequences of SEQ ID NOs: 54 and 62.

The present disclosure also provides an anti-NKG2A antibody or an antigen-binding portion thereof that competes or cross-competes for binding with, or binds to the same epitope as, antibody 24208, 23765, 23686, 23566, 23925 or 24135.

In some embodiments, the anti-NKG2A antibody or antigen-binding portion of the present disclosure comprises the H-CDR1-3 and L-CDR1-3 amino acid sequences of antibody 24208, 23765, 23686, 23566, 23925 or 24135.

In some embodiments, the anti-NKG2A antibody or antigen-binding portion of the present disclosure comprises a VH and a VL that are at least 80%, 85%, 90%, 91%, 92%, 93%, 94%, 95%, 96%, 97%, 98%, or 99% A identical in amino acid sequence to the VH and VL, respectively, of antibody 24208, 23765, 23686, 23566, 23925 or 24135.

In some embodiments, the anti-NKG2A antibody or antigen-binding portion of the present disclosure comprises a VH and a VL that are the VH and VL, respectively, of antibody 24208, 23765, 23686, 23566, 23925 or 24135.

In some embodiments, the anti-NKG2A antibody of the present disclosure is antibody 24208, 23765, 23686, 23566, 23925 or 24135, or an antibody with the same amino acid sequences as said antibody.

The class of an anti-NKG2A antibody obtained by the methods described herein may be changed or switched with another class or subclass. In some embodiments of the present disclosure, a nucleic acid molecule encoding VL or VH is isolated using methods well known in the art such that it does not include nucleic acid sequences encoding CL or CH, respectively. The nucleic acid molecules encoding VL or VH then are operatively linked to a nucleic acid sequence encoding a CL or CH, respectively, from a different class of immunoglobulin molecule. This may be achieved using a vector or nucleic acid molecule that comprises a CL or CH sequence, as described above. For example, an anti-NKG2A antibody that was originally IgM may be class switched to IgG. Further, the class switching may be used to convert one IgG subclass to another, e.g., from $IgG_1$ to $IgG_2$. A κ light chain constant region can be changed, e.g., to a λ light chain constant region, or vice-versa. An exemplary method for producing an antibody of the present disclosure with a desired Ig isotype comprises the steps of isolating a nucleic acid molecule encoding the heavy chain of an anti-NKG2A antibody and a nucleic acid molecule encoding the light chain of an anti-NKG2A antibody, obtaining the variable domain of the heavy chain, ligating a coding sequence for the variable domain of the heavy chain with a coding sequence for the constant region of a heavy chain of the desired isotype, expressing the light chain and the heavy chain encoded by the ligated sequence in a cell, and collecting the anti-NKG2A antibody with the desired isotype.

The anti-NKG2A antibody of the present disclosure can be an IgG, an IgM, an IgE, an IgA, or an IgD molecule, but is typically of the IgG isotype, e.g., of IgG subclass $IgG_1$, $IgG_2a$ or $IgG_2b$, $IgG_3$ or $IgG_4$. In some embodiments, the antibody is of the isotype subclass $IgG_1$.

In some embodiments, the anti-NKG2A antibody may comprise at least one mutation in the Fc region. A number of different Fc mutations are known, where these mutations alter the antibody's effector function. For example, in some embodiments, the anti-NKG2A antibody comprises at least one mutation in the Fc region that reduces effector function, e.g., mutations at one or more of positions 228, 233, 234 and 235, where amino acid positions are numbered according to the IMGT® numbering scheme.

In some embodiments, e.g., where the antibody is of the $IgG_1$ subclass, one or both of the amino acid residues at positions 234 and 235 may be mutated, for example from Leu to Ala (L234A/L235A). These mutations reduce effector function of the Fc region of $IgG_1$ antibodies. The amino acid positions are numbered according to the IMGT® numbering scheme.

In some embodiments, e.g., where the antibody is of the $IgG_4$ subclass, it may comprise the mutation S228P, where the amino acid position is numbered according to the IMGT® numbering scheme. This mutation is known to reduce undesired Fab arm exchange.

In some embodiments, the anti-NKG2A antibody or antigen-binding portion of the present disclosure is antagonistic.

In some embodiments, the anti-NKG2A antibody or antigen-binding portion binds to human NGK2A with a $K_D$ of 15, 10, 7, 5, 4, 3, 2, or 1 nM or less as measured by surface plasmon resonance. In some embodiments, the anti-NKG2A antibody or antigen-binding portion binds to human NGK2A with a $K_D$ that is at least 40, 30, 20, 10, or 5 times less than the $K_D$ with which it binds to human NKG2C.

In some embodiments, the anti-NKG2A antibody or antigen-binding portion does not specifically bind, or binds very little, to human NGK2C, cynomolgus NKG2A, cynomolgus NKG2C, or any combination thereof. In some embodiments, the anti-NKG2A antibody or antigen-binding portion specifically binds to human NGK2C, cynomolgus NKG2A, cynomolgus NKG2C, or any combination thereof.

In some embodiments, the anti-NKG2A antibody or antigen-binding portion binds to human NKG2A expressed on CHO-S cells, e.g., at a concentration of 30 μg/mL, 20 μg/mL, 10 μg/mL, 5 μg/mL, 1 μg/mL, 500 ng/mL, 250 ng/mL, 100, 50 ng/mL, 25 ng/mL, 10 ng/mL, 5 ng/mL, 1 ng/mL, or 0.5 ng/mL or less.

In some embodiments, the anti-NKG2A antibody or antigen-binding portion blocks binding of HLA-E to human NKG2A/CD94 heterodimer expressed on CHO-S cells, e.g., at a concentration of 10 μg/mL, 3 μg/mL, 1 μg/mL, 0.4 μg/mL, 0.1 μg/mL, 40 ng/mL, 14 ng/mL, or less.

In some embodiments, the anti-NKG2A antibody or antigen-binding portion enhances NK-92 cell-mediated killing of K562 cells transfected with HLA-E, e.g., at a concentration of 50 μg/mL, 25 μg/mL, 12.5 μg/mL, 6.25 μg/mL, 3.1 μg/mL, 1.7 μg/mL, 0.85 μg/mL, or 0.41 μg/mL or less. In certain embodiments, e.g., at one of said concentrations, the killing is enhanced by 10, 50, 100, 150, 200, 250, 300, 350, 400, 450, or 500% or more compared to untreated cells. In particular embodiments, the anti-NKG2A antibody or antigen-binding portion enhances NK-92 cell-mediated killing of K562 cells transfected with HLA-E more effectively than monalizumab.

In some embodiments, the anti-NKG2A antibody or antigen-binding portion enhances primary NK cell-mediated killing of K562 cells transfected with HLA-E, e.g., at a concentration of 50 μg/mL, 25 μg/mL, 12.5 μg/mL, 6.25 μg/mL, 3.1 μg/mL, 1.7 μg/mL, 0.85 μg/mL, or 0.41 μg/mL or less. In certain embodiments, e.g., at one of said concentrations, the killing is enhanced by 10, 50, 100, 150, 200, 250, 300, 350, 400, 450, or 500% or more compared to untreated cells. In particular embodiments, the anti-NKG2A antibody or antigen-binding portion enhances primary NK cell-mediated killing of K562 cells transfected with HLA-E more effectively than monalizumab, BMS-NKG2A.9, and/or BMS-NKG2A.11.

In some embodiments, the anti-NKG2A antibody or antigen-binding portion enhances γδ T cell-mediated killing of K562 cells transfected with HLA-E, e.g., at a concentration of 50 μg/mL, 25 μg/mL, 12.5 μg/mL, 6.25 μg/mL, 3.1 μg/mL, 1.7 μg/mL, 0.85 μg/mL, or 0.41 μg/mL or less. In certain embodiments, e.g., at one of said concentrations, the killing is enhanced by 10, 50, 100, 150, 200, 250, 300, 350, 400, 450, or 500% or more compared to untreated cells. In particular embodiments, the anti-NKG2A antibody or antigen-binding portion enhances γδ T cell-mediated killing of K562 cells transfected with HLA-E more effectively than monalizumab.

In some embodiments, the binding of the anti-NKG2A antibody or antigen-binding portion to human NKG2A is dependent on residue S170 (optionally in combination with S167 and/or I168) or residue E197 of human NKG2A.

In some embodiments, the anti-NKG2A antibody or antigen-binding portion binds to an epitope on human NKG2A comprising amino acid residue S170. In certain embodiments, the epitope further comprises amino acid residues S167 and I168. In some embodiments, the epitope (which may comprise amino acid residues S167, 1168, and/or S170) does not comprise amino acid residues E179 and/or M189.

The present disclosure also contemplates an anti-NKG2A antibody or antigen-binding portion with any combination of the above properties.

In some embodiments, an anti-NKG2A antibody or antigen-binding portion described herein has at least one (e.g., 1, 2, 3, 4, 5, 6, 7, 8, or all 9) of the following properties:
- a) binds to human NGK2A with a $K_D$ of 15 nM or less as measured by surface plasmon resonance;
- b) binds to human NKG2A expressed on CHO-S cells;
- c) blocks binding of HLA-E to human NKG2A/CD94 heterodimer expressed on CHO-S cells;
- d) enhances NK-92 cell-mediated killing of K562 cells transfected with HLA-E;
- e) enhances primary NK cell-mediated killing of K562 cells transfected with HLA-E;
- f) enhances γδ T cell-mediated killing of K562 cells transfected with HLA-E;
- g) binds to a different epitope on human NKG2A than monalizumab;
- h) enhances primary NK cell-mediated killing of HT-29, CCRF-CEM, A253, Detroit 562, CAL-120, and/or FaDu cells; and
- i) induces secretion of MIP-1β.
- For example, in certain embodiments, an anti-NKG2A antibody or antigen-binding portion described herein may have properties a)-f), a)-e), a)-g), a)-i), or a)-e) and g).

In some embodiments, an anti-NKG2A antibody or antigen-binding portion described herein may enhance NK cell and/or T cell activity in a patient.

In some embodiments, an anti-NKG2A antibody or antigen-binding portion described herein may inhibit tumor growth and/or induce tumor growth regression in vivo. In some embodiments, an anti-NKG2A antibody or antigen-binding portion described herein may slow down or reverse metastasis in a cancer patient. In some embodiments, an anti-NKG2A antibody or antigen-binding portion described herein may prolong survival of a cancer patient. Any combination of the above properties is also contemplated.

In certain embodiments, an antibody or antigen-binding portion thereof of the present disclosure may be part of a larger immunoadhesin molecule, formed by covalent or noncovalent association of the antibody or antibody portion with one or more other proteins or peptides. Examples of such immunoadhesin molecules include use of the streptavidin core region to make a tetrameric scFv molecule (Kipriyanov et al., *Human Antibodies and Hybridomas* 6:93-101 (1995)) and use of a cysteine residue, a marker peptide and a C-terminal polyhistidine tag to make bivalent and biotinylated scFv molecules (Kipriyanov et al., *Mol. Immunol.* 31:1047-1058 (1994)). Other examples include where one or more CDRs from an antibody are incorporated into a molecule either covalently or noncovalently to make it an immunoadhesin that specifically binds to an antigen of interest. In such embodiments, the CDR(s) may be incorporated as part of a larger polypeptide chain, may be covalently linked to another polypeptide chain, or may be incorporated noncovalently.

In another aspect, a fusion antibody or immunoadhesin may be made that comprises all or a portion of an anti-NKG2A antibody of the present disclosure linked to another polypeptide. In certain embodiments, only the variable domains of the anti-NKG2A antibody are linked to the polypeptide. In certain embodiments, the VH domain of an anti-NKG2A antibody is linked to a first polypeptide, while the VL domain of an anti-NKG2A antibody is linked to a second polypeptide that associates with the first polypeptide in a manner such that the VH and VL domains can interact with one another to form an antigen-binding site. In some embodiments, the VH domain is separated from the VL domain by a linker such that the VH and VL domains can interact with one another (e.g., single-chain antibodies). The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bi-specific antibody.

To create a single chain antibody (scFv), the VH- and VL-encoding DNA fragments are operatively linked to another fragment encoding a flexible linker, e.g., encoding the amino acid sequence (Gly$_4$-Ser)$_3$ (SEQ ID NO: 64), such that the VH and VL sequences can be expressed as a contiguous single-chain protein, with the VL and VH domains joined by the flexible linker. See, e.g., Bird et al., *Science* 242:423-426 (1988); Huston et al., *Proc. Natl. Acad. Sci. USA* 85:5879-5883 (1988); and McCafferty et al., *Nature* 348:552-554 (1990). The single chain antibody may be monovalent, if only a single VH and VL are used; bivalent, if two VH and VL are used; or polyvalent, if more than two VH and VL are used. Bi-specific or polyvalent antibodies may be generated that bind specifically to human NKG2A and to another molecule, for instance.

In other embodiments, other modified antibodies may be prepared using anti-NKG2A antibody-encoding nucleic acid molecules. For instance, "kappa bodies" (Ill et al., *Protein Eng.* 10:949-57 (1997)), "minibodies" (Martin et al., *EMBO J.* 13:5303-9 (1994)), "diabodies" (Holliger et al., *Proc. Natl. Acad. Sci. USA* 90:6444-6448 (1993)), or "Janusins" (Traunecker et al., *EMBO J.* 10:3655-3659 (1991) and Traunecker et al., *Int. J. Cancer (Suppl.)* 7:51-52 (1992)) may be prepared using standard molecular biological techniques following the teachings of the specification.

An anti-NKG2A antibody or antigen-binding portion of the present disclosure can be derivatized or linked to another molecule (e.g., another peptide or protein). In general, the antibodies or portions thereof are derivatized such that NKG2A binding is not affected adversely by the derivatization or labeling. Accordingly, the antibodies and antibody portions of the present disclosure are intended to include both intact and modified forms of the human anti-NKG2A antibodies described herein. For example, an antibody or antibody portion of the present disclosure can be functionally linked (by chemical coupling, genetic fusion, noncovalent association or otherwise) to one or more other molecular entities, such as another antibody (e.g., a bi-specific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by cross-linking two or more antibodies (of the same type or of different types, e.g., to create bi-specific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available, e.g., from Pierce Chemical Company, Rockford, IL An anti-NKG2A antibody or antigen-binding portion can also be derivatized with a chemical group such as polyethylene glycol (PEG), a methyl or ethyl group, or a carbohydrate group. These groups may be useful to improve the biological characteristics of the antibody, e.g., to increase serum half-life.

An antibody or antigen-binding portion according to the present disclosure may also be labeled. As used herein, the terms "label" or "labeled" refer to incorporation of another molecule in the antibody. In some embodiments, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In some embodiments, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In some embodiments, an antibody or antigen-binding portion according to the present disclosure may be conjugated to a cytotoxic agent to form an immunoconjugate. In some embodiments, an antibody or antigen-binding portion according to the present disclosure may be conjugated to a radioisotope.

In certain embodiments, the antibodies of the present disclosure may be present in a neutral form (including zwitterionic forms) or as a positively or negatively-charged species. In some embodiments, the antibodies may be complexed with a counterion to form a pharmaceutically acceptable salt.

Anti-NKG2A Antibody Compositions

The present disclosure also provides a combination therapy (e.g., a composition) that comprises one, two, three, four, or more of the anti-NKG2A antibodies or antigen-binding portions thereof described herein. In certain embodiments, the combination therapy (e.g., composition) comprises two of the anti-NKG2A antibodies or antigen-binding portions. The combination therapy may take the form of, e.g., a method of treatment using said antibodies or antigen-binding portions or a pharmaceutical composition comprising said antibodies or antigen-binding portions.

In some embodiments, the present disclosure provides a composition comprising a first anti-NKG2A antibody or an antigen-binding portion thereof and a second anti-NKG2A antibody or an antigen-binding portion thereof, wherein the first and second antibodies are:
antibodies 23765 and 23686, respectively;
antibodies 23765 and 24208, respectively;
antibodies 23765 and 23566, respectively;
antibodies 23765 and 23925, respectively;
antibodies 23765 and 24135, respectively;
antibodies 23686 and 24208, respectively;
antibodies 23686 and 23566, respectively;
antibodies 23686 and 23925, respectively;
antibodies 23686 and 24135, respectively;
antibodies 24208 and 23566, respectively;
antibodies 24208 and 23925, respectively;
antibodies 24208 and 24135, respectively;
antibodies 23566 and 23925, respectively;
antibodies 23566 and 24135, respectively; or
antibodies 23925 and 24135, respectively.

In some embodiments, the composition comprises antibodies or antigen-binding portions thereof that bind to the same epitope as, or compete for binding with, said first and second antibodies.

In some embodiments, the composition comprises an antibody or an antigen-binding portion thereof that comprises the H-CDR1-3 and L-CDR1-3 amino acid sequences of said first antibody, and an antibody or an antigen-binding portion thereof that comprises the H-CDR1-3 and L-CDR1-3 amino acid sequences of said second antibody.

In some embodiments, the composition comprises an antibody or an antigen-binding portion thereof that comprises a VH and a VL with amino acid sequences that are at least 80%, 85%, 90%, 91%, 92%, 93%, 94%, 95%, 96%, 97%, 98%, or 99% identical to the VH and VL amino acid sequences, respectively, of said first antibody, and an antibody or an antigen-binding portion thereof that comprises a VH and a VL with amino acid sequences that are at least 80%, 85%, 90%, 91%, 92%, 93%, 94%, 95%, 96%, 97%, 98%, or 99% A identical to the VH and VL amino acid sequences, respectively, of said second antibody.

In some embodiments, the composition comprises an antibody or an antigen-binding portion thereof that comprises the VH and VL amino acid sequences of said first antibody, and an antibody or an antigen-binding portion thereof that comprises the VH and VL amino acid sequences of said second antibody.

In some embodiments, the composition comprises an antibody or an antigen-binding portion thereof that comprises the HC and LC amino acid sequences of said first antibody, and an antibody or an antigen-binding portion thereof that comprises the HC and LC amino acid sequences of said second antibody.

In certain embodiments, said composition may comprise one, two, or more antibodies or antigen-binding portions thereof selected from the group consisting of:
a) an antibody comprising H-CDR1-3 that comprise the amino acid sequences of SEQ ID NOs: 5-7, 15-17, 25-27, 35-37, 45-47, or 55-57, respectively;
b) an antibody whose VH is at least 90% identical in sequence to the amino acid sequence of SEQ ID NO: 3, 13, 23, 33, 43, or 53;
c) an antibody whose VH comprises the amino acid sequence of SEQ ID NO: 3, 13, 23, 33, 43, or 53;
d) an antibody whose HC comprises the amino acid sequences of SEQ ID NOs: 3 and 61, 13 and 61, 23 and 61, 33 and 61, 43 and 61, or 53 and 61;
e) an antibody comprising L-CDR1-3 that comprise the amino acid sequences of SEQ ID NOs: 8-10, 18-20, 28-30, 38-40, 48-50, or 58-60, respectively;
f) an antibody whose VL is at least 90% identical in sequence to the amino acid sequence of SEQ ID NO: 4, 14, 24, 34, 44, or 54;
g) an antibody whose VL comprises the amino acid sequence of SEQ ID NO: 4, 14, 24, 34, 44, or 54;

h) an antibody whose LC comprises the amino acid sequences of SEQ ID NOs: 4 and 62, 14 and 62, 24 and 62, 34 and 62, 44 and 62, or 54 and 62;

i) an antibody whose H-CDR1-3 and L-CDR1-3 comprise the amino acid sequences of SEQ ID NOs: 5-10, 15-20, 25-30, 35-40, 45-50, or 55-60, respectively;

j) an antibody comprising VH and VL that comprise amino acid sequences at least 90% identical to the amino acid sequences of SEQ ID NOs: 3 and 4, 13 and 14, 23 and 24, 33 and 34, 43 and 44, or 53 and 54, respectively;

k) an antibody comprising VH and VL that comprise the amino acid sequences of SEQ ID NOs: 3 and 4, 13 and 14, 23 and 24, 33 and 34, 43 and 44, or 53 and 54, respectively; and l) an antibody comprising HC and LC that comprise the amino acid sequences of 3 and 61, and 4 and 62; 13 and 61, and 14 and 62; 23 and 61, and 24 and 62; 33 and 61, and 34 and 62; 43 and 61, and 44 and 62; or 53 and 61, and 54 and 62; respectively.

In some embodiments, an anti-NKG2A antibody composition described herein may inhibit tumor growth and/or induce tumor regression in vivo. In some embodiments, an anti-NKG2A antibody composition described herein may slow down or reverse metastasis in a cancer patient. In some embodiments, an anti-NKG2A antibody composition described herein may prolong survival of a cancer patient.

The present disclosure also provides a method for producing an anti-NKG2A antibody composition described herein, comprising providing a first anti-NKG2A antibody or antigen-binding portion and a second anti-NKG2A antibody or antigen-binding portion, and admixing the two antibodies or portions.

Bi-Specific Binding Molecules

The present disclosure also provides a bi-specific binding molecule having the binding specificity (e.g., comprising the antigen-binding portions, such as the six CDRs or the VH and VL) of an anti-NKG2A antibody described herein. In some embodiments, the bi-specific binding molecule additionally has the binding specificity of another, distinct anti-NKG2A antibody (e.g., another anti-NKG2A antibody described herein) or an antibody that targets a different protein, such as a cancer antigen or another cell surface molecule whose activity mediates a disease condition such as cancer. Such bi-specific binding molecules are known in the art, and examples of different types of bi-specific binding molecules are given elsewhere herein.

Nucleic Acid Molecules and Vectors

The present disclosure also provides nucleic acid molecules and sequences encoding anti-NKG2A antibodies or antigen-binding portions thereof described herein. In some embodiments, different nucleic acid molecules encode the heavy chain and light chain amino acid sequences of the anti-NKG2A antibody or antigen-binding portion. In other embodiments, the same nucleic acid molecule encodes the heavy chain and light chain amino acid sequences of the anti-NKG2A antibody or antigen-binding portion.

A reference to a nucleotide sequence encompasses its complement unless otherwise specified. Thus, a reference to a nucleic acid having a particular sequence should be understood to encompass its complementary strand, with its complementary sequence. The term "polynucleotide" as referred to herein means a polymeric form of nucleotides of at least 10 bases in length, either ribonucleotides or deoxynucleotides or a modified form of either type of nucleotide. The term includes single- and double-stranded forms.

In some embodiments, the present disclosure provides a nucleic acid molecule comprising a nucleotide sequence that encodes the heavy chain or an antigen-binding portion thereof, or a nucleotide sequence that encodes the light chain or an antigen-binding portion thereof, or both, of an anti-NKG2A antibody or antigen-binding portion thereof described herein.

The present disclosure also provides nucleotide sequences that are at least 70%, 75%, 80%, 85%, 90%, 95%, 97%, 98% or 99% A identical to one or more nucleotide sequences recited herein, e.g., to a nucleotide sequence selected from the group consisting of SEQ ID NOs: 1, 2, 11, 12, 21, 22, 31, 32, 41, 42, 51, and 52 or to a nucleotide sequence encoding an amino acid sequence selected from the group consisting of SEQ ID NOs: 3, 4, 13, 14, 23, 24, 33, 34, 43, 44, 53, and 54. The term "percent sequence identity" in the context of nucleic acid sequences refers to the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wisconsin FASTA, which includes, e.g., the programs FASTA2 and FASTA3, provides alignments and percent sequence identity of the regions of the best overlap between the query and search sequences (see, e.g., Pearson, *Methods Enzymol.* 183:63-98 (1990); Pearson, *Methods Mol. Biol.* 132:185-219 (2000); Pearson, *Methods Enzymol.* 266:227-258 (1996); and Pearson, *J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

In some embodiments, the present disclosure provides a nucleic acid molecule comprising a nucleotide sequence selected from the group consisting of SEQ ID NOs: 1, 2, 11, 12, 21, 22, 31, 32, 41, 42, 51, and 52. In certain embodiments, the nucleic acid molecule comprises the nucleotide sequences of SEQ ID NOs: 1 and 2, 11 and 12, 21 and 22, 31 and 32, 41 and 42, or 51 and 52.

In any of the above embodiments, the nucleic acid molecules may be isolated. Nucleic acid molecules referred to herein as "isolated" or "purified" are nucleic acids which (1) have been separated away from the nucleic acids of the genomic DNA or cellular RNA of their source of origin; and/or (2) do not occur in nature.

In a further aspect, the present disclosure provides a vector suitable for expressing one or both of the chains of an antibody or antigen-binding portion thereof as described herein. The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. Moreover, certain vectors are capable of directing the expression of genes to which they are operatively linked. Such vectors are referred to herein as "recombinant expression vectors" (or simply, "expression vectors").

The present disclosure provides vectors comprising nucleic acid molecules that encode the heavy chain, the light chain, or both the heavy and light chains of an anti-NKG2A antibody as described herein or an antigen-binding portion thereof. In certain embodiments, a vector of the present disclosure comprises a nucleic acid molecule described herein. The present disclosure further provides vectors comprising nucleic acid molecules encoding fusion proteins, modified antibodies, antibody fragments, and probes thereof. The vector may further comprise an expression control sequence.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

In some embodiments, a nucleic acid molecule as described herein comprises a nucleotide sequence encoding a VH domain from an anti-NKG2A antibody or antigen-binding portion as described herein joined in-frame to a nucleotide sequence encoding a heavy chain constant region from any source. Similarly, a nucleic acid molecule as described herein can comprise a nucleotide sequence encoding a VL domain from an anti-NKG2A antibody or antigen-binding portion as described herein joined in-frame to a nucleotide sequence encoding a light chain constant region from any source.

In a further aspect of the present disclosure, nucleic acid molecules encoding the VH and/or VL may be "converted" to full-length antibody genes. In some embodiments, nucleic acid molecules encoding the VH or VL domains are converted to full-length antibody genes by insertion into an expression vector already encoding heavy chain constant (CH) or light chain constant (CL) regions, respectively, such that the VH segment is operatively linked to the CH segment (s) within the vector, and/or the VL segment is operatively linked to the CL segment within the vector. In another aspect, nucleic acid molecules encoding the VH and/or VL domains are converted into full-length antibody genes by linking, e.g., ligating, a nucleic acid molecule encoding a VH and/or VL domain to a nucleic acid molecule encoding a CH and/or CL region using standard molecular biological techniques. Nucleic acid molecules encoding the full-length heavy and/or light chains may then be expressed from a cell into which they have been introduced and the anti-NKG2A antibody isolated.

In some embodiments, the framework region(s) are mutated so that the resulting framework region(s) have the amino acid sequence of the corresponding germ line gene. A mutation may be made in a framework region or constant region, e.g., to increase the half-life of the anti-NKG2A antibody. See, e.g., PCT Publication WO 00/09560. A mutation in a framework region or constant region also can be made to alter the immunogenicity of the antibody, and/or to provide a site for covalent or noncovalent binding to another molecule. According to the present disclosure, an antibody may have mutations in any one or more of the CDRs or framework regions of the variable domain or in the constant region.

Host Cells and Methods of Antibody and Antibody Composition Production

The present disclosure also provides methods for producing the antibody compositions and antibodies and antigen-binding portions thereof described herein. In some embodiments, the present disclosure relates to a method for producing an anti-NKG2A antibody or antigen-binding portion as described herein, comprising providing a host cell (e.g., a recombinant host cell) comprising a nucleotide sequence that encodes the heavy chain or an antigen-binding portion thereof, and a nucleotide sequence that encodes the light chain or an antigen-binding portion thereof, of an anti-NKG2A antibody or antigen-binding portion described herein; cultivating said host cell under conditions suitable for expression of the antibody or antigen-binding portion; and isolating the resulting antibody or antigen-binding portion. Antibodies or antigen-binding portions produced by such expression in such recombinant host cells are referred to herein as "recombinant" antibodies or antigen-binding portions. The present disclosure also provides progeny cells of such host cells, and antibodies or antigen-binding portions produced by same.

The term "recombinant host cell" (or simply "host cell"), as used herein, means a cell into which a recombinant expression vector has been introduced. By definition, a recombinant host cell does not occur in nature. The present disclosure provides host cells that may comprise, e.g., a vector as described herein. The present disclosure also provides host cells that comprise, e.g., a nucleotide sequence encoding the heavy chain or an antigen-binding portion thereof, a nucleotide sequence encoding the light chain or an antigen-binding portion thereof, or both, of an anti-NKG2A antibody or antigen-binding portion thereof described herein. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

Nucleic acid molecules encoding anti-NKG2A antibodies and antigen-binding portions thereof and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

It is likely that antibodies expressed by different cell lines or in transgenic animals will have different glycosylation patterns from each other. However, all antibodies encoded by the nucleic acid molecules provided herein, or comprising the amino acid sequences provided herein are part of the present disclosure, regardless of the glycosylation state of the antibodies, and more generally, regardless of the presence or absence of post-translational modification(s).

Pharmaceutical Compositions

Another aspect of the present disclosure is a pharmaceutical composition comprising as an active ingredient (or as the sole active ingredient) an anti-NKG2A antibody or antigen-binding portion thereof, antibody composition, or bi-specific binding molecule of the present disclosure. The pharmaceutical composition may additionally comprise a pharmaceutically acceptable excipient. In some embodiments, the pharmaceutical compositions are intended for amelioration, prevention, and/or treatment of cancer, e.g., a cancer described herein. In certain embodiments, the cancer is in a tissue such as skin, lung, intestine, colon, ovary, brain, prostate, kidney, soft tissues, the hematopoietic system, head and neck, liver, bone, bladder, breast, stomach, uterus, cervix, and pancreas.

Pharmaceutical compositions of the present disclosure will comprise one or more anti-NKG2A antibodies, antigen-binding portions, antibody compositions, or bi-specific binding molecules of the present disclosure, e.g., one or two anti-NKG2A antibodies, antigen-binding portions, or bi-specific binding molecules. In some embodiments, the composition comprises a single anti-NKG2A antibody of the present disclosure or an antigen-binding portion thereof. In another aspect, the composition comprises two distinct anti-NKG2A antibodies of the present disclosure or antigen-binding portions thereof.

In some embodiments, the pharmaceutical composition may comprise at least one anti-NKG2A antibody or antigen-binding portion thereof of the present disclosure, e.g., one anti-NKG2A antibody or portion, and one or more additional antibodies that target one or more relevant cell surface receptors, e.g., one or more cancer-relevant receptors.

In some embodiments, the pharmaceutical composition may comprise at least one anti-NKG2A antibody or antigen-binding portion thereof of the present disclosure, e.g., one anti-NKG2A antibody or portion, and one or more additional agents selected from, e.g., an immunostimulatory agent, a vaccine, a chemotherapeutic agent, an anti-neoplastic agent, an anti-angiogenic agent, and a tyrosine kinase inhibitor.

Generally, the antibodies, antigen-binding portions, and bi-specific binding molecules of the present disclosure are suitable to be administered as a formulation in association with one or more pharmaceutically acceptable excipient(s), e.g., as described below.

The term "excipient" is used herein to describe any ingredient other than the compound(s) of the present disclosure. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present disclosure and methods for their preparation will be readily apparent to those skilled in the art. Such compositions and methods for their preparation may be found, for example, in *Remington's Pharmaceutical Sciences,* 19th Edition (Mack Publishing Company, 1995). Pharmaceutical compositions are preferably manufactured under GMP (good manufacturing practices) conditions.

A pharmaceutical composition of the present disclosure may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In some embodiments of a formulation for parenteral administration, the active ingredient is provided in dry (i.e., powder or granular) form for reconstitution with a suitable vehicle (e.g., sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation.

Therapeutic Uses of Antibodies and Compositions of the Present Disclosure

In some embodiments, the anti-NKG2A antibodies and antigen-binding portions thereof, anti-NKG2A antibody compositions, and bi-specific binding molecules of the present disclosure are used to enhance or activate the immune system in a patient (e.g., a mammal such as a human) in need thereof, e.g., by enhancing the activity of NKG2A$^+$ NK cells or T cells. In certain embodiments, the patient is immune-suppressed. In certain embodiments, a physician can boost the anti-cancer activity of a patient's own immune system by administering an anti-NKG2A antibody or antigen-binding portion thereof, composition, or bi-specific binding molecule as described herein. For example, a physician can boost anti-tumor activity in a patient by administering an anti-NKG2A antibody or antigen-binding portion, antibody composition, or bi-specific binding molecule of the present disclosure, alone or in combination with other therapeutic agents (sequentially or concurrently).

In certain embodiments, the antibodies or antigen-binding portions thereof, compositions, or bi-specific binding molecules of the present disclosure are for use in the treatment of cancer. The cancer may be in one or more tissues such as skin, lung, intestine, colon, ovary, brain, prostate, kidney, soft tissues, the hematopoietic system, head and neck, liver, bone, bladder, breast, stomach, uterus, cervix, and pancreas.

In some embodiments, cancers treated by the anti-NKG2A antibodies, antigen-binding portions, compositions, and bi-specific binding molecules of the present disclosure may include, e.g., melanoma (e.g., advanced or metastatic melanoma), skin basal cell cancer, glioblastoma, glioma, gliosarcoma, astrocytoma, meningioma, neuroblastoma, adrenocortical cancer, head and neck squamous cell cancer, oral cancer, salivary gland cancer, nasopharyngeal cancer, breast cancer, lung cancer (e.g., non-small cell lung cancer (NSCLC), small cell lung cancer, and squamous cell lung cancer), esophageal cancer, gastroesophageal junction cancer, gastric cancer, gastrointestinal cancer, primary peritoneal cancer, liver cancer, hepatocellular carcinoma, biliary tract cancer, colon cancer, rectal cancer, colorectal carcinoma, ovarian cancer, fallopian tube cancer, bladder cancer, upper urinary tract cancer, urothelial cancer, renal cell carcinoma, kidney cancer, genitourinary cancer, cervical cancer, prostate cancer, fibrosarcoma, liposarcoma, rhabdomyosarcoma, osteosarcoma, histiocytoma, pancreatic cancer, endometrial cancer, cancer of the appendix, advanced Merkel cell cancer, multiple myeloma, sarcomas, choriocarcinoma, erythroleukemia, acute lymphoblastic leukemia, acute monocytic leukemia, acute promyelocytic leukemia, acute myeloid leukemia, chronic myeloid leukemia, chronic lymphocytic leukemia, acute lymphoblastic leukemia, mast cell leukemia, small lymphocytic lymphoma, Burkitt's lymphoma, Hodgkin's lymphoma, non-Hodgkin's lymphoma, diffuse large B cell lymphoma, follicular lymphoma, monocytic lymphoma, HTLV-associated T cell leukemia/lymphoma, mesothelioma, and solid tumors. The cancer may be, e.g., at an early, intermediate, late, locally advanced, or metastatic stage, and may be relapsed or refractory to other therapeutics (e.g., other anti-NKG2A therapeutics, or checkpoint inhibitors) or there may be no standard therapy available.

In some embodiments, conditions treated by the anti-NKG2A antibodies, antigen-binding portions, compositions, and bi-specific binding molecules of the present disclosure may include, e.g., head and neck cancer, breast cancer (e.g., HER2-positive breast cancer), colorectal cancer, lung cancer (e.g., non-small cell lung cancer), esophageal cancer, acute myeloid leukemia, acute lymphoblastic leukemia, myelodysplastic syndromes, multiple myeloma, chronic lymphoid leukemia, chronic myeloid leukemia, myeloproliferative neoplasm, Hodgkin's lymphoma, and non-Hodgkin's lymphoma.

In some embodiments, the antibodies or antigen-binding portions thereof, compositions, or bi-specific binding molecules of the present disclosure are for use in the treatment of an immune disorder.

In some embodiments, the antibody or antigen-binding portion, composition, or bi-specific binding molecule may be used to treat a patient who is, or is at risk of being, immunocompromised (e.g., due to chemotherapeutic or radiation therapy). In some embodiments, the antibody or antigen-binding portion, composition, or bi-specific binding molecule may be used to expand stem cells in a patient after stem cell transplantation.

In some embodiments, the antibody or antigen-binding portion, composition, or bi-specific binding molecule is for use in treating viral and/or parasitic infections, e.g., where the pathogens inhibit the host immune response. The pathogen may be, e.g., HIV, hepatitis (A, B, or C), human papilloma virus (HPV), lymphocytic choriomeningitis virus (LCMV), adenovirus, flavivirus, echovirus, rhinovirus, coxsackie virus, coronavirus, respiratory syncytial virus, mumps virus, rotavirus, measles virus, rubella virus, parvovirus, vaccinia virus, human T-cell lymphotrophic virus (HTLV), human cytomegalovirus (HCMV), dengue virus, molluscum virus, poliovirus, rabies virus, John Cunningham (JC) virus, arboviral encephalitis virus, simian immunodeficiency virus (SIV), influenza, herpes, Giardia, malaria, *Leishmania, Staphylococcus aureus,* or *Pseudomonas aeruginosa.*

"Treat," "treating," and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

"Therapeutically effective amount" refers to the amount of the therapeutic agent being administered that will relieve to some extent one or more of the symptoms of the disorder being treated. A therapeutically effective amount of an anti-cancer therapeutic may, for example, result in delayed tumor growth, tumor shrinkage, increased survival, elimination of cancer cells, slowed or decreased disease progression, reversal of metastasis, or other clinical endpoints desired by healthcare professionals.

The anti-NKG2A antibodies or antigen-binding portions thereof, antibody compositions, or bi-specific binding molecules described herein may be administered alone or in combination with one or more other drugs or antibodies (or as any combination thereof). The pharmaceutical compositions, methods and uses described herein thus also encompass embodiments of combinations (co-administration) with other active agents, as detailed below.

As used herein, the terms "co-administration," "co-administered" and "in combination with," referring to the anti-NKG2A antibodies and antigen-binding portions thereof, antibody compositions, and bi-specific binding molecules of the present disclosure with one or more other therapeutic agents, is intended to mean, and does refer to and include the following:

a) simultaneous administration of such combination of antibody/antigen-binding portion/antibody composition/bi-specific binding molecule of the present disclosure and therapeutic agent(s) to a patient in need of treatment, when such components are formulated together into a single dosage form which releases said components at substantially the same time to said patient, b) substantially simultaneous administration of such combination of antibody/antigen-binding portion/antibody composition/bi-specific binding molecule of the present disclosure and therapeutic agent(s) to a patient in need of treatment, when such components are formulated apart from each other into separate dosage forms which are taken at substantially the same time by said patient, whereupon said components are released at substantially the same time to said patient, c) sequential administration of such combination of antibody/antigen-binding portion/antibody composition/bi-specific binding molecule of the present disclosure and therapeutic agent(s) to a patient in need of treatment, when such components are formulated apart from each other into separate dosage forms which are taken at consecutive times by said patient with a significant time interval between each administration, whereupon said components are released at substantially different times to said patient; and d) sequential administration of such combination of antibody/antigen-binding portion/antibody composition/bi-specific binding molecule of the present disclosure and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

The anti-NKG2A antibodies or antigen-binding portions thereof, antibody compositions, or bi-specific binding molecules of the present disclosure may be administered without additional therapeutic treatments, i.e., as a stand-alone therapy (monotherapy). Alternatively, treatment with the anti-NKG2A antibodies or antigen-binding portions thereof, antibody compositions, or bi-specific binding molecules of the present disclosure may include at least one additional therapeutic treatment (combination therapy), e.g., another immunostimulatory agent, an anti-cancer agent (e.g., a chemotherapeutic agent, an anti-neoplastic agent, an anti-angiogenic agent, or a tyrosine kinase inhibitor), or a vaccine (e.g., a tumor vaccine).

In some embodiments, the antibody or antigen-binding portion thereof, antibody composition, or bi-specific binding molecule may be co-administered or formulated with another medication/drug for the treatment of cancer. The additional therapeutic treatment may comprise, e.g., an immunostimulatory agent, a vaccine, a chemotherapeutic agent, an anti-neoplastic agent, an anti-angiogenic agent, a tyrosine kinase inhibitor, and/or radiation therapy. In some embodiments, the additional therapeutic treatment may comprise a different anti-cancer antibody.

Pharmaceutical articles comprising an anti-NKG2A antibody or antigen-binding portion thereof, antibody composition, or bi-specific binding molecule described herein and at least one other agent (e.g., a chemotherapeutic, anti-neoplastic, or anti-angiogenic agent) may be used as a combination treatment for simultaneous, separate or successive administration in cancer therapy. The other agent may by any agent suitable for treatment of the particular cancer in question, for example, an agent selected from the group consisting of alkylating agents, e.g., platinum derivatives such as cisplatin, carboplatin and/or oxaliplatin; plant alkoids, e.g., paclitaxel, docetaxel and/or irinotecan; antitumor antibiotics, e.g., doxorubicin (adriamycin), daunorubicin, epirubicin, idarubicin mitoxantrone, dactinomycin, bleomycin, actinomycin, luteomycin, and/or mitomycin; topoisomerase inhibitors such as topotecan; antimetabolites, e.g., fluorouracil and/or other fluoropyrimidines; FOLFOX; osimertinib; cyclophosphamide; anthracycline; dacarbazine; gemcitabine; or any combination thereof. In some embodiments, the anti-NKG2A antibody or antigen-binding portion thereof, antibody composition, or bi-specific binding molecule described herein reestablishes responsiveness to the other agent.

An anti-NKG2A antibody or antigen-binding portion thereof, antibody composition, or bi-specific binding molecule of the present disclosure may also be used in combination with other anti-cancer therapies such as vaccines, cytokines, enzyme inhibitors, immunostimulatory compounds, and T cell therapies. In the case of a vaccine, it may be, e.g., a protein, peptide, or DNA vaccine containing one or more antigens which are relevant for the cancer being treated, or a vaccine comprising dendritic cells along with an antigen. Suitable cytokines include, for example, IL-2, IFN-gamma and GM-CSF. An example of a type of enzyme inhibitor that has anti-cancer activity is an indoleamine-2,3-dioxygenase (IDO) inhibitor, for example, 1-methyl-D-tryptophan (1-D-MT). Also contemplated is adoptive T cell therapy, which refers to various immunotherapy techniques that involve expanding or engineering patients' own T cells to recognize and attack their tumors.

It is also contemplated that an anti-NKG2A antibody or antigen-binding portion thereof, antibody composition, or bi-specific binding molecule of the present disclosure may be used in adjunctive therapy in connection with tyrosine kinase inhibitors. These are synthetic, mainly quinazoline-derived, low molecular weight molecules that interact with the intracellular tyrosine kinase domain of receptors and inhibit ligand-induced receptor phosphorylation, e.g., by competing for the intracellular Mg-ATP binding site.

In some embodiments, the antibody or antigen-binding portion thereof, antibody composition, or bi-specific binding molecule may be used in combination with a medication/drug that mediates immune system activation, including, but not limited to, an agent that modulates the expression or activity of A2AR, A1AR, A2BR, A3AR, ADA, ALP, AXL, BTLA, B7-H3, B7-H4, CTLA-4, CD116, CD123, CD27, CD28, CD39, CD40, CD47, CD55, CD73, CD122, CD137, CD160, CGEN-15049, CHK1, CHK2, CTLA-3, CEACAM (e.g., CEACAM-1 and/or CEACAM-5), EGFR, FLT3, NKG2AL, GAL9, GITR, HVEM, LAG-3, LILRB1, LY108, LAIR1, MET, ICOS, IDO, IL2R, IL4R, KIR, LAIR1, PAP, PD-1/PD-L1/PD-L2, OX40, STING, TIGIT, TIM-3, TGFR-beta, TLR1, TLR2, TLR3, TLR4, TLR5, TLR6, TLR7, TLR8, TLR9 and TLR10, TNFR2, VEGFR, VEGF, VISTA, LILRB2, CMTM6 and/or 2B4. In certain embodiments, the agent is a small molecule inhibitor. In certain embodiments, the agent is an antibody or an antigen-binding fragment thereof that binds to one of the above molecules. It is also contemplated that an anti-NKG2A antibody or antigen-binding portion thereof, antibody composition, or bi-specific binding molecule of the present disclosure may be used in combination with a cytokine (e.g., IL-1, IL-2, IL-12, IL-15 or IL-21), an EGFR inhibitor, a VEGF inhibitor, etc.

In some embodiments, the antibody or antigen-binding portion thereof, antibody composition, or bi-specific binding molecule may be used in combination with trastuzumab, pembrolizumab, nivolumab, durvalumab, ibrutinib, cetuximab, avelumab, rituximab, margetuximab, tafasitamab, bevacizumab, trastuzumab deruxtecan, trifluridine, tipiracil, trifluridine/tipiracil, irinotecan, gemcitabine, oxaliplatin, bendamustine, FOLFOX (e.g., mFOLFOX6), or any combination thereof.

In particular embodiments, the antibody or antigen-binding portion thereof, antibody composition, or bi-specific binding molecule may be used in combination with an agent that modulates the expression or activity of CD94, an agent that modulates the expression or activity of HLA-E, or both.

The present disclosure also contemplates the use of sequences (e.g., the six CDR or VH and VL sequences) of an anti-NKG2A antibody or antigen-binding portion described herein in the preparation of a chimeric antigen receptor, which may be for use in CAR-T technology.

It is understood that the antibodies and antigen-binding portions thereof, antibody compositions, and bi-specific binding molecules of the present disclosure may be used in a method of treatment as described herein, may be for use in a treatment as described herein, and/or may be for use in the manufacture of a medicament for a treatment as described herein.

Dose and Route of Administration

The antibodies or antigen-binding portions thereof, antibody compositions, or bi-specific binding molecules of the present disclosure may be administered in an effective amount for treatment of the condition in question, i.e., at dosages and for periods of time necessary to achieve a desired result. A therapeutically effective amount may vary according to factors such as the particular condition being treated, the age, sex and weight of the patient, and whether the antibodies are being administered as a stand-alone treatment or in combination with one or more additional anti-cancer treatments.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the present disclosure are generally dictated by and directly dependent on (a) the unique characteristics of the therapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen are adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present disclosure.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the embodied composition. Further, the dosage regimen with the compositions of the present disclosure may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-patient dose-escalation as determined by the skilled artisan. Determining of appropriate dosages and regimens is well-known in the relevant art and would be understood to be encompassed by the skilled artisan once provided the teachings disclosed herein.

An effective amount for tumor therapy may be measured by its ability to stabilize disease progression and/or ameliorate symptoms in a patient, and preferably to reverse disease progression, e.g., by reducing tumor size. The ability of an antibody, antigen-binding portion, antibody composition, or bi-specific binding molecule of the present disclosure to inhibit cancer may be evaluated by in vitro assays, e.g., as described in the examples, as well as in suitable animal models that are predictive of the efficacy in human tumors. Suitable dosage regimens will be selected in order to provide an optimum therapeutic response in each particular situation, for example, administered as a single bolus or as a continuous infusion, and with possible adjustment of the dosage as indicated by the exigencies of each case.

The antibodies or antigen-binding portions thereof, antibody compositions, or bi-specific binding molecules of the present disclosure may be administered by any method for administering peptides, proteins or antibodies accepted in the art, and are typically suitable for parenteral administration. As used herein, "parenteral administration" includes any route of administration characterized by physical breaching of a tissue of a subject and administration through the breach in the tissue, thus generally resulting in the direct administration into the blood stream, into muscle, or into an internal organ. Parenteral administration thus includes, but is not limited to, administration by injection, by application through a surgical incision, by application through a tissue-penetrating non-surgical wound, and the like. In particular, parenteral administration is contemplated to include, but is not limited to, subcutaneous, intraperitoneal, intramuscular, intrasternal, intracisternal, intravenous, intraarterial, intrathecal, intraurethral, intracranial, intratumoral, and intrasynovial injection or infusions. Particular embodiments include the intravenous and the subcutaneous routes.

Diagnostic Uses and Compositions

The antibodies and antigen-binding portions of the present disclosure also are useful in diagnostic processes (e.g., in vitro, ex vivo). For example, the antibodies and antigen-binding portions can be used to detect and/or measure the level of NKG2A in a sample from a patient (e.g., a tissue sample, or a body fluid sample such as an inflammatory exudate, blood, serum, bowel fluid, saliva, or urine). Suitable detection and measurement methods include immunological methods such as flow cytometry, enzyme-linked immunosorbent assays (ELISA), chemiluminescence assays, radioimmunoassays, and immunohistology. The present disclosure further encompasses kits (e.g., diagnostic kits) comprising the antibodies and antigen-binding portions described herein.

Articles of Manufacture and Kits

The present disclosure also provides articles of manufacture, e.g., kits, comprising one or more containers (e.g., single-use or multi-use containers) containing a pharmaceutical composition of an anti-NKG2A antibody or antigen-binding portion thereof, composition, or bi-specific binding molecule described herein, optionally an additional biologically active molecule (e.g., another therapeutic agent), and instructions for use. The antibody or antigen-binding portion, composition, or bi-specific binding molecule, and optional additional biologically active molecule, can be packaged separately in suitable packing such as a vial or ampule made from non-reactive glass or plastic. In certain embodiments, the vial or ampule holds a concentrated stock (e.g., 2×, 5×, 10× or more) of the antibody or antigen-binding portion, composition, or bi-specific binding molecule and optionally the biologically active molecule. In certain embodiments, the articles of manufacture such as kits include a medical device for administering the antibody or antigen-binding portion, composition, or bi-specific binding molecule and/or biologically active molecule (e.g., a syringe and a needle); and/or an appropriate diluent (e.g., sterile water and normal saline). The present disclosure also includes methods for manufacturing said articles.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control.

Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein.

Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers.

All publications and other references mentioned herein are incorporated by reference in their entirety. Although a number of documents are cited herein, this citation does not constitute an admission that any of these documents forms part of the common general knowledge in the art.

In order that the present disclosure may be better understood, the following examples are set forth. These examples are for purposes of illustration only and are not to be construed as limiting the scope of the present disclosure in any manner.

EXAMPLES

Example 1. Cloning of Anti-NKG2A Antibodies from Rat B Cells

Materials and Methods

Antibodies against human NKG2A were isolated from an antibody repertoire derived from OmniRat® rats (Osborn et al., *J Immunol.* 190(4):1481-90 (2013)), a transgenic rat strain from Ligand Pharmaceuticals Inc. that produces antibodies with fully human idiotypes. Cloning of rat-derived antibody genes from single-cell sorted antibody-secreting B cells (ASC) was performed by means of Symplex™ antibody discovery technology (Meijer et al., *J Mol Biol* 358 (3):764-72 (2006)).

Antibody repertoire constructs encoding fully human immunoglobulins in IgG$_1$-LALA format (see below) were transfected into HEK293 cells. Cell supernatants were screened for binding to NKG2A expressed on the surface of CHO cells using flow cytometry in a high-throughput format. NKG2A reactive clones were analyzed by DNA sequencing and antibody-encoding DNA sequences were extracted. Selected antibody clones were expressed and tested functionally as described below.

Missense mutations in the amino termini of heavy and light chains that were introduced by the use of degenerate primers in the Symplex™ cloning of the antibody-encoding cDNA fragments were corrected back to germline sequence. Table 1 shows the heavy and light chain variable domain nucleotide sequences of the germlined antibodies designated 23765, 23686, 24208, 23566, 23925 and 24135. The correction process involves amino terminal sequence correction to germline as well as codon usage optimization. The targets for matching to human germ line sequences were identified by blast homology searches for the heavy chain and the light chain variable regions.

Protein sequences of the variable domains, the constant regions and the complementarity determining regions (CDRs) of antibodies 24208, 23765, 23686, 23566, 23925 and 24135 are shown in Table 2, Table 3, and Table 4, respectively.

Results

Table 1 shows nucleotide sequences encoding the variable domains of antibodies 24208, 23765, 23686, 23566, 23925 and 24135.

TABLE 1

Variable domain nucleotide sequences of antibodies 24208, 23765, 23686, 23566, 23925 and 24135

| Ab | Sequence (5' to 3') | SEQ |
|---|---|---|
| 24208 VH | CAGGTGCAGCTGGTCGAGAGCGGAGGAGGACTGGTGAAGCCAGGTGG AAGTCTGCGACTGTCATGCGCCGCTTCCGGATTCACCTTTTCTGACT ACTATATGAGGTGGATCCGGCAGGCCCCTGGAAAAGGGCTGGAATGG GTGTCACACATCTCCACTAGCGGCTCTACCATCTACTATGCTGACTC CGTCAAGGGCAGATTCACAATTAGCCGCGATAACGCAAAAAATTCTC TGTACCTGCAAATGAACAGTCTGCGCGCAGAGGACACTGCCGTGTAC TATTGCGCCAGGGACCATTACTATAGTCGTGGAGTGATCGGGTATTG GGGTCAGGGCACCCTGGTCACAGTCTCG | 1 |

TABLE 1-continued

Variable domain nucleotide sequences of antibodies
24208, 23765, 23686, 23566, 23925 and 24135

| Ab | Sequence (5' to 3') | SEQ |
|---|---|---|
| 23765 VH | GAGGTGCAGCTGGTCGAAAGTGGAGGAGGACTGGTGAAGCCAGGTGG<br>ATCTCTGAGACTGAGTTGCGCCGCTTCAGGGTTCACATTTTCTTGCT<br>GTCGCATGAACTGGGTGCGGCAGGCACCTGGAAAAGGACTGGAGTGG<br>GTCTCCAGCATCTCTTCTTCATCCTCTTACATCTACTATGCTGACTC<br>CGTGAAGGGAAGATTCACTATCTCCCGCGATAACGCAAAAAATAGCC<br>TGTATCTGCAGATGAACTCTCTGCAGCAGAAGACACCGCCGTCTAC<br>TATTGTGCTAGGGATGGCTGGAATGACGTGTTTGATTACTGGGGTCA<br>GGGCACCCTGGTCACAGTCTCG | 11 |
| 23686 VH | GAGGTGCAGCTGGTCGAAAGTGGAGGAGGACTGGTGAAGCCAGGTGG<br>ATCACTGCGACTGTCCTGCGCCGCCTCCGGCTTCACATTTTCCTCTT<br>ACTCTATGAACTGGGTTAGGCAGGCCCCTGGAAAAGGGCTGGAGTGG<br>GTCTCTAGTATCTCATCCAGCTCTAGTTACATCTACTATGCTGACTC<br>TGTGAAGGGCAGGTTCACTATCTCTCGGGATAACGCAAAAAATAGTC<br>TGTATCTGCAGATGAATTCACTGAGAGCAGAGGAGACCGCCGTGTAC<br>TATTGTGCTCGCGACGAATGGGACTGCTGGGGTTTGATTCCTGGGG<br>TCAGGGCACCCTGGTCACAGTCTCG | 21 |
| 23566 VH | GAGGTGCAGCTGCTGGAAAAGCGGAGGAGACCTGGTCCAGCCAGGAGG<br>TTCCCTGCGACTGAGCTGCGCCGCTTCTGGCTTCACTTTTGATAACT<br>ACGCCATGCACTGGGTGAGGCAGGCTCCTGGGAAGGGTCTGGAGTGG<br>GTCTCCACTATCACCAATAGCGGCGGAACCACATACTATGCAGACTC<br>TGTGAAGGGGAGGTTCACCCTGAGTCGGGATAACTCAAAAAATACAC<br>TGTACCTGCAGATGAACAGTCTGAGAGCTGAAGACACAGCAGTGTAC<br>TATTGTGCAAAAGCCCATTACTATGCTCGCGGCTATTTCGATTTTTG<br>GGGCCAGGGAACACTGGTCACTGTCTCG | 31 |
| 23925 VH | GAGGTGCAGCTGGTCGAATCCGGAGGAGGACTGGTGCAGCCAGGTGG<br>ATCACTGCGACTGTCCTGCGCCGCCTCCGGATTCACCTTTTCCAGTT<br>ACGCCATGAACTGGGTTAGGCAGGCTCCTGGCAAGGGACTGGAGTGG<br>GTCTCAACAATCTCTAATAGTGGAGGGACCACATACTATGCAGACTC<br>TGTGAAGGGCAGGTTCACAATTTCTCGGGACAACAGTAAAGATACTC<br>TGTATCTGCAAATGAATTCCCTGAGAGCTGAAGACACCGCAGTGTAG<br>TATTGTGCAAAAGCCCACTACTATGCTCGCGGCTACTTTGATTATTG<br>GGGACAGGGGACTCTGGTCACCGTCTCG | 41 |
| 24135 VH | CAGGTGCAGCTGCAGGAGAGCGGGCCAGGTCTGGTGAAGCCCTCTGA<br>AACACTGAGTCTGACATGCACTGTTAGTGGCGGATCAGTCTCCAGCG<br>GCCACTACTATTGGTCTTGGATTAGACAACCCCCTGGCAAGGGACTG<br>GAGTGGATCGGCTATATCTACTATTCAGGATCCACCACATACAACCC<br>TTCCCTGAAAAGCCGGGTGAGCATTTCTGTCGACACTTCAAAGCATC<br>AGTTCAGTCTGAAACTGTCTAGTGTGACCGCCGCTGATACAGCTGTC<br>TACTATTGTGCAAGATGGGCCGGGTCCTATCAGCCATACTATTACTA<br>TTACGGCATGGACGTGTGGGGGCAGGGTACTACCGTCACCGTCTCG | 51 |
| 24208 VL | GACATCCAGATGACCCAGTCCCCTTCCAGCGTTAGTGCTTCAGTCGG<br>AGATAGGGTGACCATCACATGCCGGGCTTCCCAGGGGATTTCTAGTT<br>GGCTGGCATGGTACCAGCAGAAGCCCGGAAAAGCCCCTAAGCTGCTG<br>ATCTATGCCGCTTCATCCCTGCAAAGTGGCGTCCCATCTAGATTCTC<br>CGGCAGCGGATCTGGGACCGACTTTACTCTGACCATTAGTTCTCTGC<br>AGCCAGAGGATTTCGCAACATACTATTGTCAGCAGGCCAACAGCTTC<br>CCCTACACATTTGGTCAGGGCACTAAACTGGAAATTAAG | 2 |
| 23765 VL | GAGATCGTGCTGACTCAGAGCCCAGCAACCCTGTCACTGTCCCCCGG<br>AGAAAGGGCAACCCTGTCTTGCCGGGCCAGCCAGTCTGTCCTCTT<br>ACCTGGCTTGGTATCAGCAAAAGCCCGGGCAGGCACCTCGACTGCTG<br>ATCTACGACGCCAGTAACAGAGCTACCGGAATTCCCGCCCGCTTCAG<br>TGGTTCAGGCTCCGGAACAGACTTTACCCTGACAATCTCTAGTCTGG<br>AGCCTGAAGATTTCGCCGTGTACTATTGTCAGCAGAGGTCTAATTGG<br>CCACTGACATTTGGCGGAGGGACTAAGGTCGAGATCAAG | 12 |
| 23686 VL | GAGATCGTGCTGACTCAGTCTCCTGCAACCCTGTCTCTGAGTCCCGG<br>CGAAAGGGCAACTCTGTCCTGCCGGGCCTCACAGTCCATTTCTAACT<br>ACCTGGCTTGGTATCAGCAAAAGCCAGGACAGGCACCCCGACTGCTG<br>ATCTACGACGCCTCCAATAGAGCTACCGGCATTCCCGCCCGCTTCTC<br>TGGCTCTGGATCAGGGACAGACTTCACCCTGACAATCTCCAGCCTGG<br>AGCCTGAAGACTTCGCCGTGTACTATTGTCAGCAGAGGACAGATTGG<br>CCCCCTTGGACATTTGGTCAGGGCACTAAGGTCGAGATCAAG | 22 |
| 23566 VL | GACATGCAGATGACCCAGACACCTTCGAGCGTTAGTGCTTGAGTCGG<br>AGATAGGGTGACTATCACCTGCCGGGCTTCCCAGGGGATTTCTAGTT<br>GGCTGGCATGGTACCAGCAGAAGCCCGGAAAAGCCCCTAAGCTGCTG | 32 |

TABLE 1-continued

Variable domain nucleotide sequences of antibodies 24208, 23765, 23686, 23566, 23925 and 24135

| Ab | Sequence (5' to 3') | SEQ |
|---|---|---|
| | ATCTATGCCGCTTCATCCCTGCAAAGTGGCGTCCCATCTAGATTCTC<br>CGGCAGCGGATCTGGGACTGACTTTACACTGACTATTAGCTCTCTGC<br>AGCCAGAGGATTTCGCAACATACTATTGTCAGCAGGCCAACTCCTTC<br>CCCTACACCTTTGGTCAGGGCACAAAACTGGAAATTAAG | |
| 23925 VL | GACATCCAGATGACCCAGAGCCCCTCCAGCGTTAGTGCTTCAGTCGG<br>AGATAGGGTGACCATCACATGCCGGGCTAGTCAGGGGATTTCTAGTT<br>GGCTGGCATGGTACCAGCAGAAGTCTGGAAAAGCCCCCAAGCTGCTG<br>ATCTATGCCGCTTCATCCCTGCAAATTGGCGTCCCTTCCCGATTCTC<br>CGGCAGCGGATCTGGGACCGACTTTACTCTGACCATCAGCTCTCTGC<br>AGCCAGAGGATTTCGCAACATACTATTGTCAGCAGGCCAACTCCTTC<br>CCCTACACATTTGGTCAGGGCACTAAACTGGAAATTAAG | 42 |
| 24135 VL | GACATCCAGATGACCCAGAGTCCTTCCAGCCTGTCAGCATCCGTGGG<br>CGACAGAGTCACCATCACATGCCAGGCCTCACAGGATATTTCCAACT<br>ACCTGAATTGGTATCAGCAGAAGCCCGGGAAAGCCCCTAAGCTGCTG<br>ATCTACGACGCCTCCAACCTGGAGAGGGGAGTGCCATCTCGGTTCAG<br>CGGTTCTGGCAGTGGAACCGATTTCACTTTTACCATCTCTTCTCTGC<br>AACCAGAGGACATTGCTAGATACTACTGTCAGCAGTACGATAACTTC<br>CCCCTGACATTTGGCGGAGGGACTAAAGTCGAAATCAAG | 52 |

SEQ: SEQ ID NO.

Table 2 shows the deduced amino acid sequences of antibodies 24208, 23765, 23686, 23566, 23925 and 24135. CDRs are in bold/underlined.

TABLE 2

Variable domain amino acid sequences of antibodies 24208, 23765, 23686, 23566, 23925 and 24135

| Ab | Sequence (N-terminal to C-terminal) | SEQ |
|---|---|---|
| 24208 VH | QVQLVESGGGLVKPGGSLRLSCAASGFTFSDYYMRWIRQAPGKGLEWV<br>SHISTSGSTIYYADSVKGRFTISRDNAKNSLYLQMNSLRAEDTAVYYC<br>ARDHYYSRGVIGYWGQGTLVTSS | 3 |
| 23765 VH | EVQLVESGGGLVKPGGSLRLSCAASGFTFSCCRMNWVRQAPGKGLEWV<br>SSISSSSSYIYYADSVKGRFTISRDNAKNSLYLQMNSLRAEDTAVYYC<br>ARDGWNDVFDYWGQGTLVTVSS | 13 |
| 23686 VH | EVQLVESGGGLVKPGGSLRLSCAASGFTFSSYSMNWVRQAPGKGLEWV<br>SSISSSSSYIYYADSVKGRFTISRDNAKNSLYLQMNSLRAEDTAVYYC<br>ARDEWGLLGFDSWGQGTLVTVSS | 23 |
| 23566 VH | EVQLLESGGDLVQPGGSLRLSCAASGFTFDNYAMHWVRQAPGKGLEWV<br>STITNSGGTTYYADSVKGRFTLSRDNSKNTLYLQMNSLRAEDTAVYYC<br>AKAHYYARGYFDFWGQGTLVTVSS | 33 |
| 23925 VH | EVQLVESGGGLVQPGGSLRLSCAASGFTFSSYAMNWVRQAPGKGLEWV<br>STISNSGGTTYYADSVKGRFTISRDNSKDTLYLQMNSLRAEDTAVYYC<br>AKAHYYARGYFDYWGQGTLVTVSS | 43 |
| 24135 VH | QVQLQESGPGLVKPSETLSLTCTVSGGSVSSGHYYWSWIRQPPGKGLE<br>WIGYIYYSGSTTYNPSLKSRVSISVDTSKHQFSLKLSSVTAADTAVYY<br>CARWAGSYQPYYYYYGMDVWGQGTTVTVSS | 53 |
| 24208 VL | DIQMTQSPSSVSASVGDRVTITCRASQGISSWLAWYQQKPGKAPKLLI<br>YAASSLQSGVPSRFSGSGSGTDFTLTISSLQPEDFATYYCQQANSFPY<br>TFGQGTKLEIK | 4 |
| 23765 VL | EIVLTQSPATLSLSPGERATLSCRASQSVSSYLAWYQQKPGQAPRLLI<br>YDASNRATGIPARFSGSGSGTDFTLTISSLEPEDFAVYYCQQRSNWPL<br>TFGGGTKVEIK | 14 |
| 23686 VL | EIVLTQSPATLSLSPGERATLSCRASQSISNYLAWYQQKPGQAPRLLI<br>YDASNRATGIPARFSGSGSGTDFTLTISSLEPEDFAVYYCQQRTDWPP<br>WTFGQGTKVEIK | 24 |
| 23566 VL | DIQMTQTPSSVSASVGDRVTITCRASQGISSWLAWYQQKPGKAPKLLI<br>YAASSLQSGVPSRFSGSGSGTDFTLTISSLQPEDFATYYCQQANSFPY<br>TFGQGTKLEIK | 34 |

TABLE 2-continued

Variable domain amino acid sequences of antibodies
24208, 23765, 23686, 23566, 23925 and 24135

| Ab | Sequence (N-terminal to C-terminal) | SEQ |
|---|---|---|
| 23925 VL | DIQMTQSPSSVSASVGDRVTITCRASQGISSWLAWYQQKSGKAPKLLI YAASSLQIGVPSRFSGSGSGTDFTLTISSLQPEDFATYYCQQANSFPY TFGQGTKLEIK | 44 |
| 24135 VL | DIQMTQSPSSLSASVGDRVTITCQASQDISNYLNWYQQKPGKAPKLLI YDASNLERGVPSRFSGSGSGTDFTFTISSLQPEDIATYYCQQYDNFPL TFGGGTKVEIK | 54 |

SEQ: SEQ ID NO.

Table 3 shows heavy and light chain constant region amino acid sequences (CH and CL, respectively). "IgG$_1$ LALA" refers to the presence of "LALA" mutations in the heavy chain (L234A/L235A, numbered according to the IMGT® numbering scheme) that are known to reduce effector function of the Fc region of IgG$_1$ antibodies (Hezareh et al., *J Virol.* 75(24):12161-68 (2001); Hessell et al., *Nature* 449(7158):101-04 (2007)).

TABLE 3

Constant region amino acid sequences of antibodies
24208, 23765, 23686, 23566, 23925 and 24135

| Fragment | Sequence (N-terminal to C-terminal) | SEQ |
|---|---|---|
| IgG$_1$-LALA CH added to the VH | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPEAAGGPSVFLFPPKPKDTLMISRTPEVTC VVVDVSHEDPEVKFNWYVDGVEVHNAKTKPREEQYNSTYRVVSVLTVL HQDWLNGKEYKCKVSNKALPAPIEKTISKAKGQPREPQVYTLPPSREE MTKNQVSLTCLVKGFYPSDIAVEWESNGQPENNYKTTPPVLDSDGSFF LYSKLTVDKSRWQQGNVFSCSVMHEALHNHYTQKSLSLSPGK | 61 |
| Kappa CL added to the VL | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC | 62 |

SEQ: SEQ ID NO.

Table 4 shows heavy and light chain CDR amino acid sequences of antibodies 24208, 23765, 23686, 23566, 23925 and 24135, wherein the CDRs are defined according to the IMGT® system.

TABLE 4

CDR amino acid sequences of antibodies
24208, 23765, 23686, 23566, 23925 and 24135

Sequence (N-terminal to C-terminal)

| Ab | H-CDR1 | H-CDR2 | H-CDR3 | L-CDR1 | L-CDR2 | L-CDR3 |
|---|---|---|---|---|---|---|
| 24208 | GFTFSDYY SEQ: 5 | ISTSGSTI SEQ: 6 | CARDHYYSRG VIGYW SEQ: 7 | QGISSW SEQ: 8 | AAS SEQ: 9 | CQQANSFPYTF SEQ: 10 |
| 23765 | GFTFSCCR SEQ: 15 | ISSSSSYI SEQ: 16 | CARDGWNDVF DYW SEQ: 17 | QSVSSY SEQ: 18 | DAS SEQ: 19 | CQQRSNWPLTF SEQ: 20 |
| 23686 | GFTFSSYS SEQ: 25 | ISSSSSYI SEQ: 26 | CARDEWGLLG FDSW SEQ: 27 | QSISNY SEQ: 28 | DAS SEQ: 29 | CQQRTDWPPWTF SEQ: 30 |
| 23566 | GFTFDNYA SEQ: 35 | ITNSGGTT SEQ: 36 | CAKAHYYARG YFDFW SEQ: 37 | QGISSW SEQ: 38 | AAS SEQ: 39 | CQQANSFPYTF SEQ: 40 |

TABLE 4-continued

CDR amino acid sequences of antibodies
24208, 23765, 23686, 23566, 23925 and 24135

Sequence (N-terminal to C-terminal)

| Ab | H-CDR1 | H-CDR2 | H-CDR3 | L-CDR1 | L-CDR2 | L-CDR3 |
|---|---|---|---|---|---|---|
| 23925 | GFTFSSYA SEQ: 45 | ISNSGGTT SEQ: 46 | CAKAHYYARG YFDYW SEQ: 47 | QGISSW SEQ: 48 | AAS SEQ: 49 | CQQANSFPYTF SEQ: 50 |
| 24135 | GGSVSSGHYY SEQ: 55 | IYYSGST SEQ: 56 | CARWAGSYQP YYYYYGMDVW SEQ: 57 | QDISNY SEQ: 58 | DAS SEQ: 59 | CQQYDNFPLTF SEQ: 60 |

SEQ: SEQ ID NO:

Table 5 shows SEQ ID NO information for antibodies 24208, 23765, 23686, 23566, 23925 and 24135. Unless otherwise stated, the sequences are amino acid sequences.

TABLE 5

SEQ ID NOs for antibodies
24208, 23765, 23686, 23566, 23925 and 24135

| Name | VH nt | VL nt | VH aa | VL aa | H-CDR1 | H-CDR2 | H-CDR3 | L-CDR1 | L-CDR2 | L-CDR3 |
|---|---|---|---|---|---|---|---|---|---|---|
| 24208 | 1 | 2 | 3 | 4 | 5 | 6 | 7 | 8 | 9 | 10 |
| 23765 | 11 | 12 | 13 | 14 | 15 | 16 | 17 | 18 | 19 | 20 |
| 23686 | 21 | 22 | 23 | 24 | 25 | 26 | 27 | 28 | 29 | 30 |
| 23566 | 31 | 32 | 33 | 34 | 35 | 36 | 37 | 38 | 39 | 40 |
| 23925 | 41 | 42 | 43 | 44 | 45 | 46 | 47 | 48 | 49 | 50 |
| 24135 | 51 | 52 | 53 | 54 | 55 | 56 | 57 | 58 | 59 | 60 | nt: nucleotide aa: amino acid

Example 2. Cloning of Anti-NKG2A Reference Antibody Analogues

This example lists the sources of the amino acid sequences and the final antibody format used for generation of anti-NKG2A reference antibody analogues.

Materials and Methods

The amino acid sequences of the heavy and light chain variable domains of the antibody analogues in Table 6 were obtained from the listed patent publication. The protein sequences were reverse translated to DNA sequences with human codon usage. The corresponding DNA sequences were gene synthesized and cloned into expression vectors containing human heavy or light chain constant domains, resulting in expression of full-length antibodies. The human antibody isotype selected for expression is listed in the antibody format column together with additional mutations introduced in the Fc region. CHO cells were transfected with the resulting expression plasmids using a standard protein expression system. The antibody supernatants were purified using standard protein A purification column chromatography.

TABLE 6

Listing of gene-synthesized antibody analogues
and the corresponding antibody format

| Antibody | Antibody format | Source |
|---|---|---|
| Monalizumab Analogue | IgG$_4$-S228P | WO 2016/062851_A1 (SEQ ID NOs: 2 and 7) |
| Monalizumab-IgG$_1$-LALA | IgG$_1$-LALA | WO 2016/062851_A1 (SEQ ID NOs: 2 and 7) |

Example 3. Measurement of Antibody Binding Kinetics Towards Human NKG2A/CD94 and NKG2C/CD94 Heterodimers This example measures the binding of anti-NKG2A antibodies to recombinant human NKG2A/CD94 and NKG2C/CD94 heterodimers (extracellular domains) as measured by surface plasmon resonance (SPR).

Materials and Methods

Kinetic binding analysis of anti-NKG2A monoclonal antibodies (mAbs) was performed by Surface Plasmon Resonance (SPR) using a Continuous Flow Microspotter (CFM, Wasatch Microfluidics, Salt Lake City, US) combined with an IBIS MX96 SPR instrument (IBIS Technologies, The Netherlands). The extracellular domains (ECDs) of human his-tagged NKG2A, NKG2C and FLAG-tagged CD94 were co-expressed using an Expi293™ expression system and purified by standard Ni-NTA chromatography followed by anti-Flag M2 affinity gel (A2220, Sigma). Binding kinetics were measured by capturing mAbs on a G-a-hu-IgG Fc SensEye® for 15 minutes using the CFM. After spotting, the SensEye® was positioned in the IBIS MX96 biosensor and immobilized mAbs were fixed by SensEye FixIt kit. Kinetic analysis was performed by applying a kinetic titration series injecting increasing concentrations of antigens from 1.6 nM to 400 nM as 2-fold dilutions. After each cycle of antigen injection, the surface was regenerated by 100 mM $H_3PO_4$, pH 3. Antigen association and dissociation were measured for 15 minutes. The recorded binding responses were fitted to a simple 1:1 binding model with Scrubber 2.0 software for calculation of the on-rate ($k_{on}$ or $k_a$), off-rate ($k_{off}$ or $k_d$) and affinity ($K_D$) constants. Binding kinetic parameters were measured as an average of three independent measuring points.

Results

The binding affinities and kinetic parameters of the anti-NKG2A mAbs binding to NKG2A/CD94 and NKG2C/

CD94 heterodimers are shown in Table 7. The binding affinities ($K_D$) of mAb 24208, 23925, 23566, and 24135 for NKG2A/CD94 were 30-50 times stronger than their binding affinities to NKG2C/CD94. MAb 23686 had similar binding affinities to NKG2A/CD94 and NKG2C/CD94. None of the mAbs bound to CD94 homodimer (data not shown).

In summary, anti-NKG2A mAbs, 24208, 23925, 23566, and 24135 have high binding specificity for NKG2A in comparison to NKG2C. MAb 23686 binds NKG2A and NKG2C with similar affinities.

TABLE 7

Binding kinetics of anti-NKG2A mAbs to human NKG2A/CD94 or NKG2C/CD94 ECDs as measured by SPR

| MAb | ECD | ka ($M^{-1} s^{-1}$) | kd ($s^{-1}$) | $K_D$ (nM) | SD, n = 3, $K_D$ (nM) |
|---|---|---|---|---|---|
| 24208 | HuNKG2A/huCD94 | 5.9E+05 | 1.5E−03 | 2.6 | 0.3 |
|  | HuNKG2C/huCD94 | 1.0E+04 | 1.2E−03 | 123 | 11 |
| 23925 | HuNKG2A/huCD94 | 1.9E+05 | 4.2E−04 | 2.23 | 0.01 |
|  | HuNKG2C/huCD94 | 8.8E+03 | 6.0E−04 | 68 | 1 |
| 23566 | HuNKG2A/huCD94 | 4.2E+05 | 1.1E−03 | 2.5 | 0.1 |
|  | HuNKG2C/huCD94 | 8.5E+03 | 8.3E−04 | 98 | 10 |
| 24135 | HuNKG2A/huCD94 | 3.4E+05 | 1.3E−03 | 3.7 | 0.1 |
|  | HuNKG2C/huCD94 | 6.7E+03 | 9.8E−04 | 147 | 3 |
| 23765 | HuNKG2A/huCD94 | 8.8E+04 | 1.3E−03 | 15.0 | 0.5 |
|  | HuNKG2C/huCD94 | 2.18E+03 | 1.56E−03 | 717 | 30 |
| 23686 | HuNKG2A/huCD94 | 2.0E+05 | 1.4E−04 | 0.72 | 0.02 |
|  | HuNKG2C/huCD94 | 6.7E+05 | 2.6E−03 | 3.9 | 0.1 |

Example 4. In Vitro Binding of Anti-Human NKG2A Antibodies to CHO-S Cells Transiently Transfected with Human or Cynomolgus NKG2A and NKG2C This example describes in vitro binding of six anti-human NKG2A monoclonal antibodies to human and cynomolgus NKG2A and NKG2C receptors expressed on transiently transfected CHO-S cells. Reference antibody analogues and isotype controls were included for comparison.

Materials and Methods

CHO-S cells were transiently transfected with human NKG2A and human CD94, human NKG2C and human CD94, cynomolgus NKG2A and cynomolgus CD94 or cynomolgus NKG2C and cynomolgus CD94 constructs. Mock transfected CHO-S cells were included in the assay as a negative control. Antibodies were tested for binding to the transfected cells in 3-fold dilutions from 30 µg/mL down to 0.5 ng/mL antibody, and 0 µg/mL antibody, and incubated for 30 min at 4° C. Following a washing step, the cells were incubated with a fluorescent goat anti-human IgG (H+L) secondary antibody (A-21445, Invitrogen) for 30 min at 4° C. in the dark. After a second wash, the cells were tested by high throughput flow cytometry (IQue screener, Sartorius). Data were transferred to Excel and graphs were generated using GraphPad Prism® software.

Results

FIG. 1 shows dose-response curves of antibody binding to human or cynomolgus NKG2A and NKG2C expressed on transiently transfected CHO-S cells. All antibodies bound strongly and dose dependently to human NKG2A. Antibody 23686 bound all four different constructs. Four antibodies, 23566, 23925, 24135 and 24208, exhibited very weak binding to human NKG2C. Antibody 23765 bound cynomolgus NKG2A, but only weakly bound human and cynomolgus NKG2C. The monalizumab analogue bound both cynomolgus NKG2A and cynomolgus NKG2C.

Example 5. In Vitro Blocking of HLA-E Binding to NKG2A and NKG2C by Anti-Human NKG2A Antibodies This example describes in vitro blocking by six anti-human NKG2A monoclonal antibodies of HLA-E binding to human and cynomolgus NKG2A and NKG2C transiently expressed on CHO-S cells. A reference antibody analogue and an isotype control were included for comparison.

Materials and Methods

CHO-S cells were transiently transfected with constructs for expression of human NKG2A and human CD94, human NKG2C and human CD94, cynomolgus NKG2A and cynomolgus CD94, or cynomolgus NKG2C and cynomolgus CD94. Mock transfected CHO-S cells were included in the assay as negative control. A PE-conjugated HLA-E pentamer was tested for binding to the heterodimers in the presence of anti-human NKG2A antibodies in 3-fold serial dilutions from 10 µg/mL down to 14 ng/mL antibody, and 0 µg/mL antibody. The antibodies were allowed to bind for 30 min at 4° C. prior to the addition of the HLA-E pentamer in a 1:50 dilution. The fluorescence intensity of HLA-E binding to the transfected cells was measured by high throughput flow cytometry (IQue screener, Sartorius). Data were transferred to Excel and graphs were generated using GraphPad Prism® software.

Results

Figure 2:
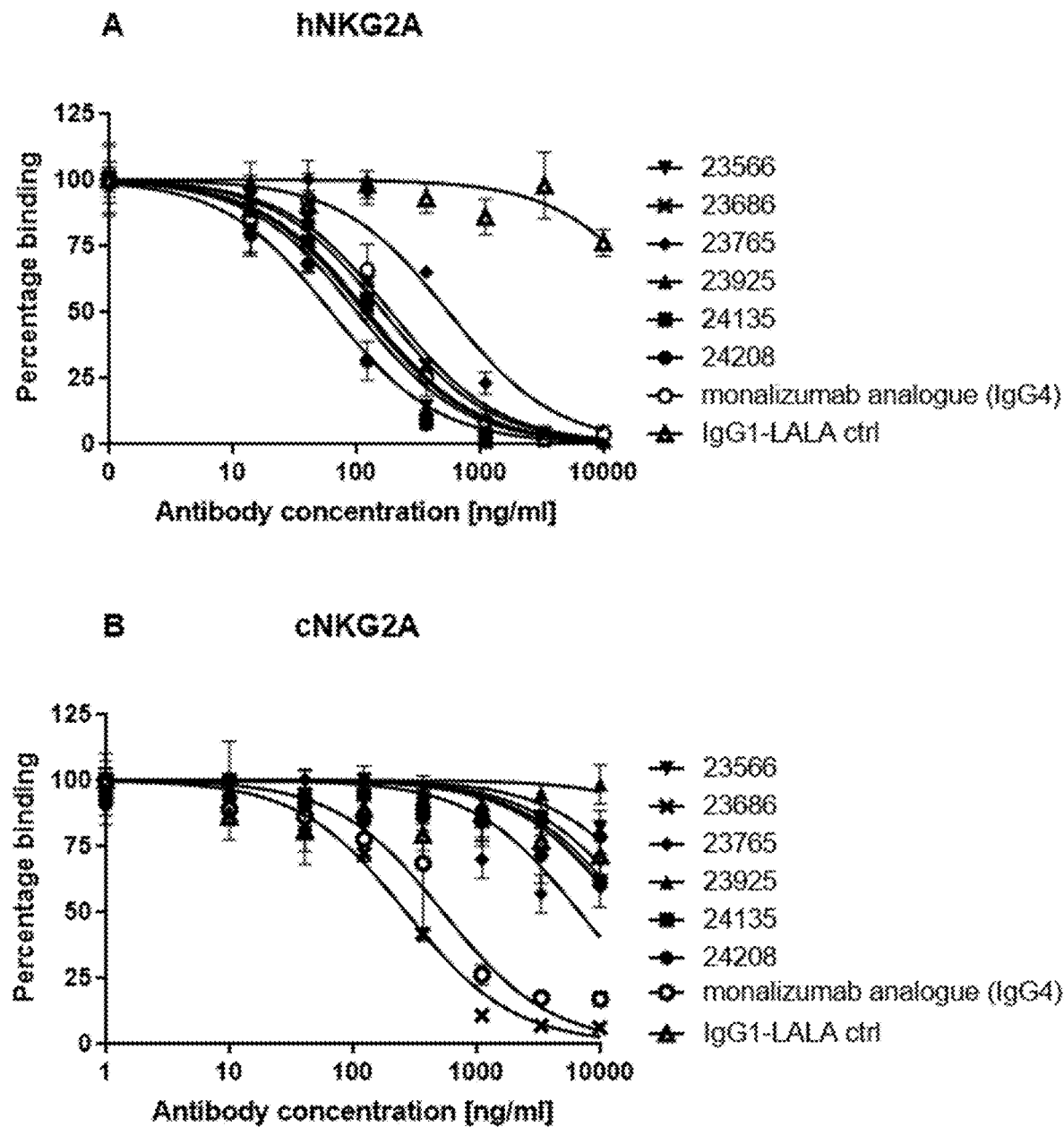
FIG. 2 is a set of graphs showing the ability of six anti-human NKG2A antibodies, a reference antibody, and a control antibody to block the binding of HLA-E to CHO-S cells transiently transfected with human NKG2A (Panel A), cynomolgus NKG2A (Panel B), human NKG2C (Panel C) or cynomolgus NKG2C (Panel D).
Figure 2:
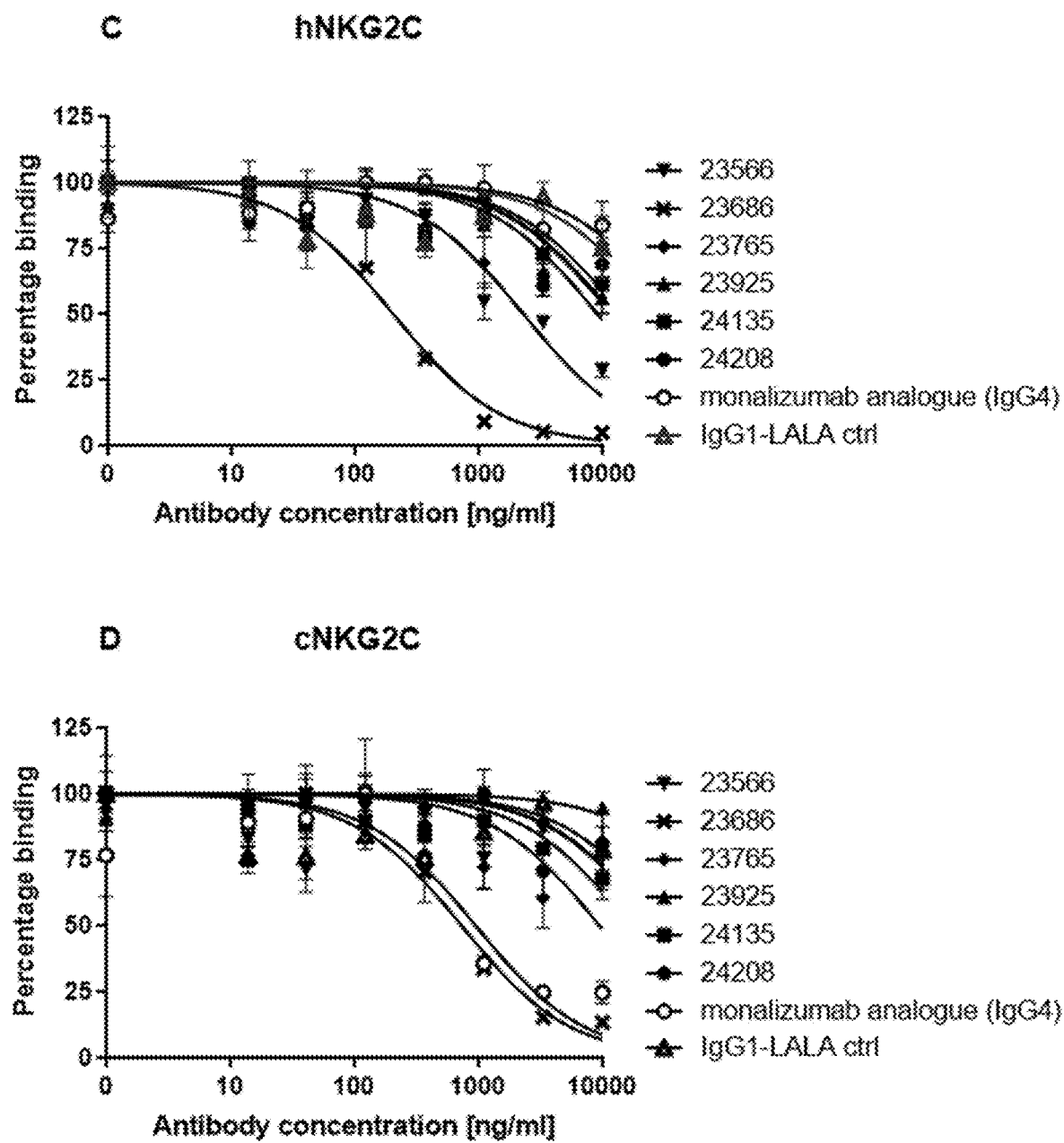

As shown in FIG. 2, all of the antibodies inhibited HLA-E binding to human NKG2A in a dose dependent manner (Panel A). Only 23686 and the monalizumab analogue ($IgG_4$) fully blocked HLA-E binding to cynomolgus NKG2A (Panel B). HLA-E binding to human NKG2C was blocked by 23686, and with lower potency by 23566 (Panel C). Only the monalizumab analogue ($IgG_4$) and 23686 fully blocked HLA-E binding to cynomolgus NKG2C (Panel D).

Example 6. Binding of Anti-Human NKG2A Antibodies to NKG2A Epitopes

This example describes in vitro binding of anti-human NKG2A monoclonal antibodies to different NKG2A/CD94 heterodimers in which one residue from the human NKG2A ECD has been exchanged with a human NKG2C residue in the corresponding position. Six different constructs encoding heterodimers with one amino acid substitution, and one construct encoding a heterodimer with three amino acid substitutions, were transiently transfected into CHO-S cells, with mock transfected CHO-S cells serving as negative control. A reference antibody analogue and an isotype control antibody were included for comparison.

Materials and Methods

Figure 3:
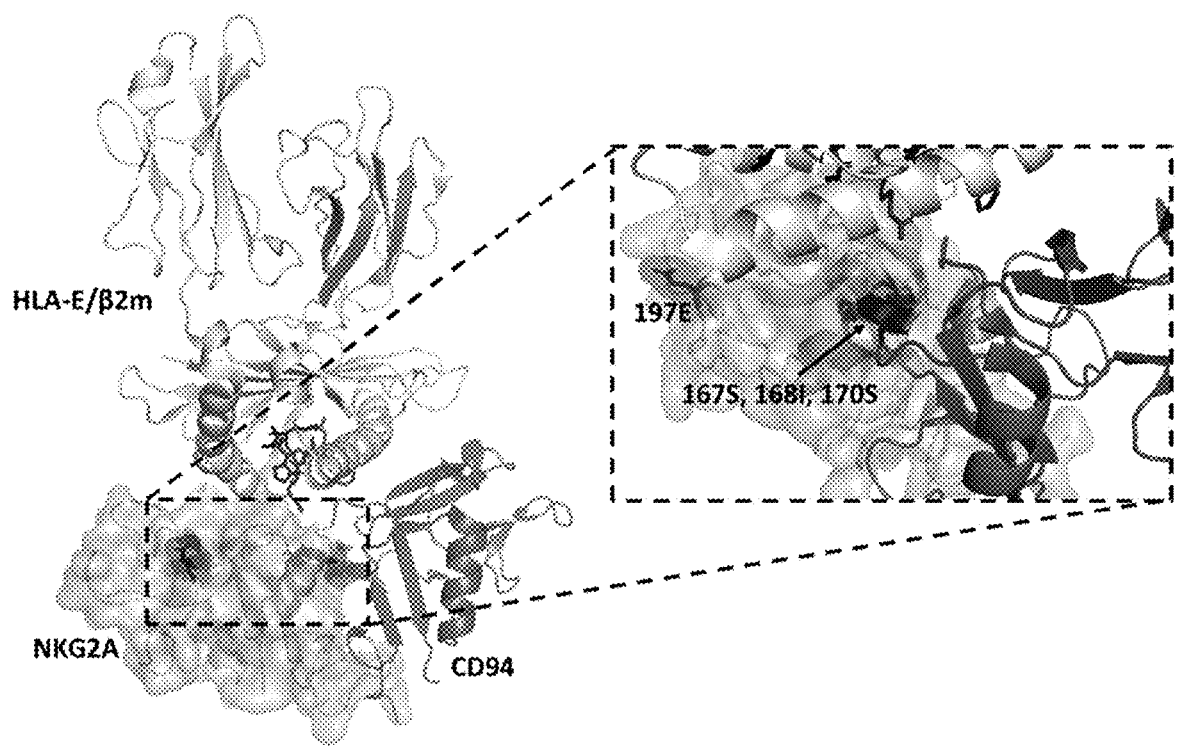
FIG. 3 depicts the crystal structure of human NKG2A/CD94 in complex with HLA-E/$\beta$2m (PDB: 3CDG). HLA-E/$\beta$2m and CD94 are shown as ribbons. NKG2A is shown as surface representation. Key binding epitope residues for certain anti-human NKG2A antibodies (as discussed in Example 6) are highlighted in black as sticks.

CHO-S cells were transiently transfected with nucleic acid constructs encoding human NKG2A and human CD94 ECD with one of the following NKG2A amino acid substitutions: S167A, I168S, S5170L, M189I, E197K, I225M, or the triple substituted S167A+I168S+S170L (corresponding to residues on the receptor that are part of the binding site for HLA-E) (Kaiser et al., *Proc Natl Acad Sci USA* (2008) 105(18):6696-701). FIG. 3 shows four of the amino acid substitutions highlighted on the crystal structure of the human NKG2A/CD94 heterodimer in complex with HLA-E (PDB: 3CDG).

Six anti-human NKG2A antibodies were tested for binding to the different heterodimers expressed. Antibodies were tested for binding to the transfected cells in 3-fold serial dilutions from 1 µg/mL antibody, and 0 µg/ml antibody, and incubated for 30 min at 4° C. Following a washing step, the cells were incubated with a fluorescent goat anti-human IgG (H+L) secondary antibody (A-21445, Invitrogen) for 30 min at 4° C. in the dark. After a second wash, the cells were tested by high throughput flow cytometry (IQue screener, Sartorius). Data were transferred to Excel and graphs were generated using GraphPad Prism® software. A reference antibody analogue and an isotype control were included for comparison.

Results

Figure 4:
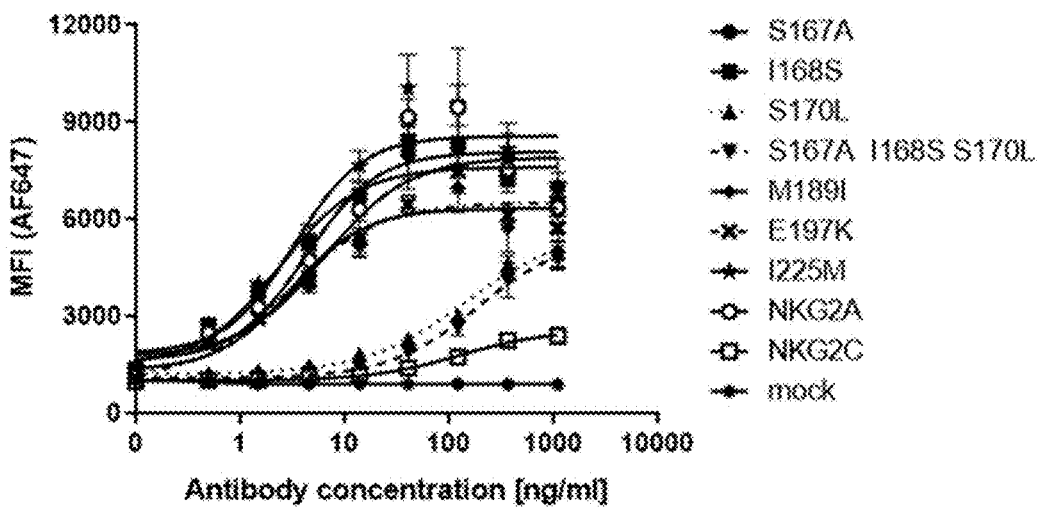
FIG. 4 is a set of graphs showing the binding of six anti-human NKG2A antibodies, a reference antibody, and a control antibody to human NKG2A extracellular domains (ECDs) with single or triple amino acid substitutions to the residue(s) at the corresponding position(s) of human NKG2C. MFI: Mean fluorescence intensity; mock: mock-transfected cells.
Figure 4:
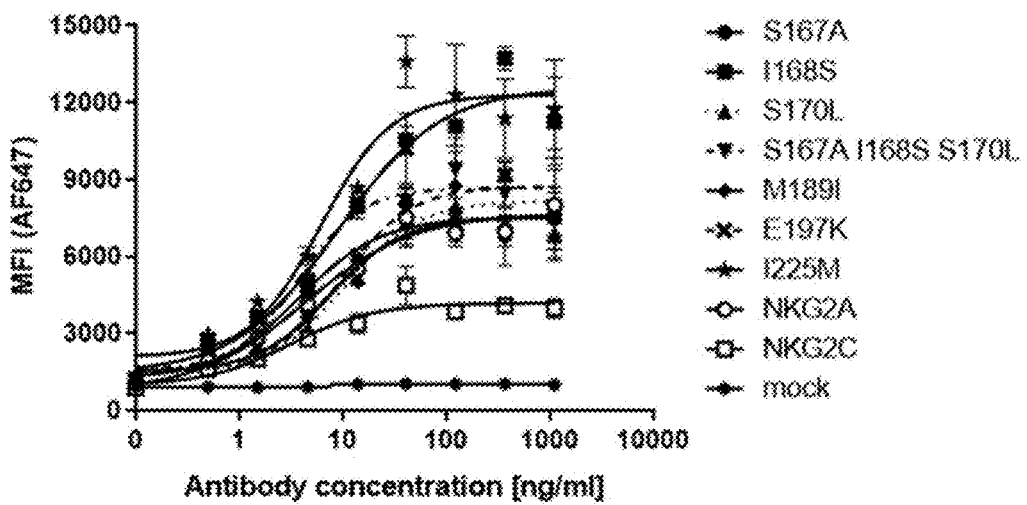
Figure 4:
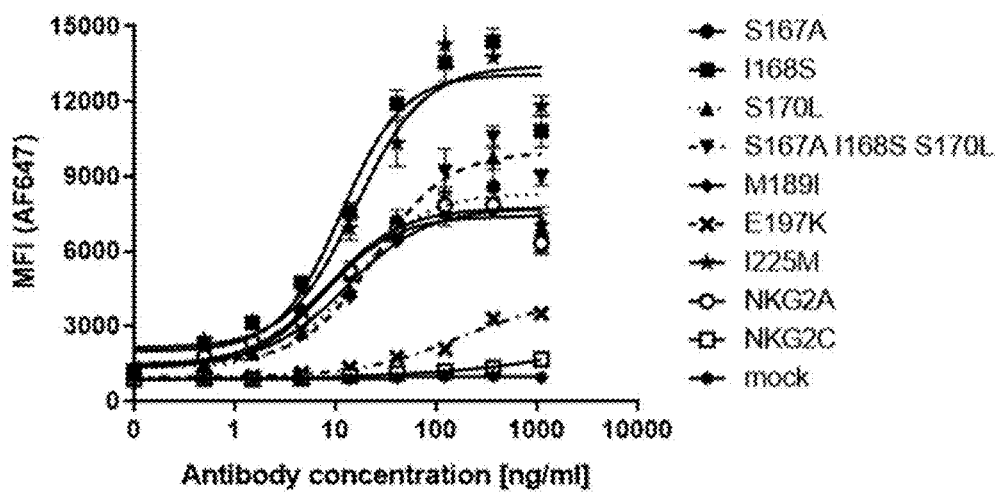
Figure 4:
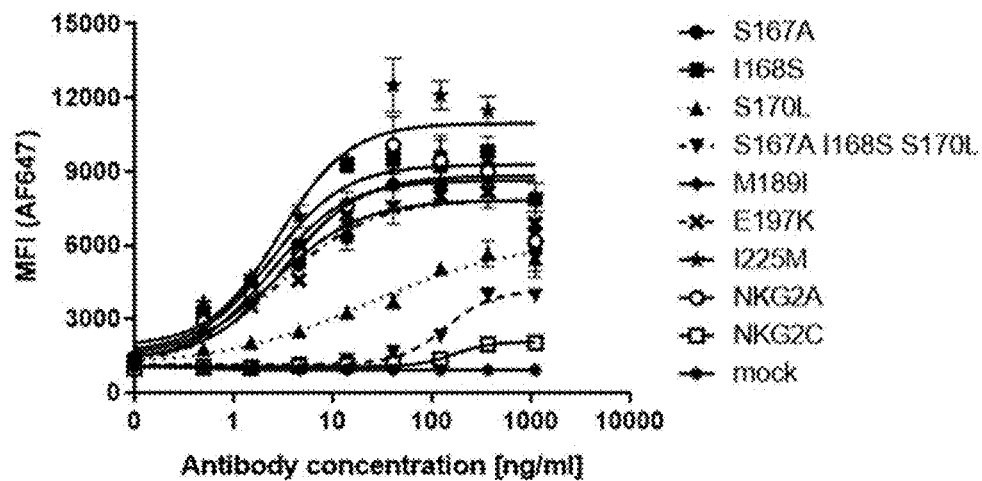
Figure 4:
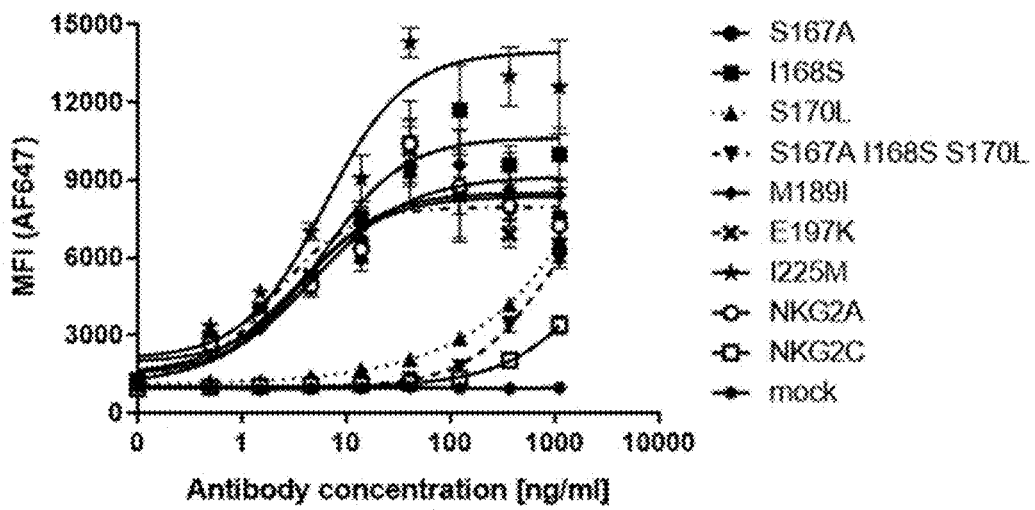
Figure 4:
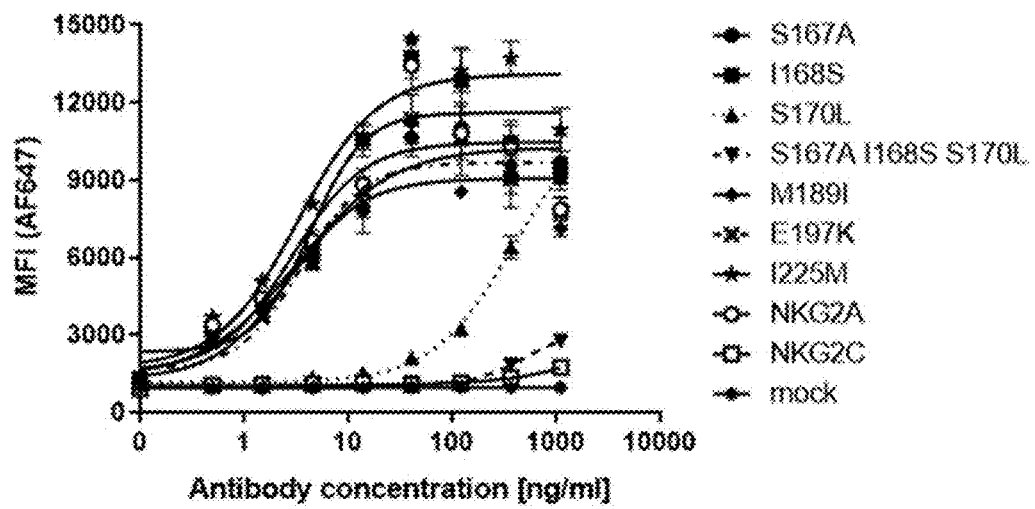
Figure 4:
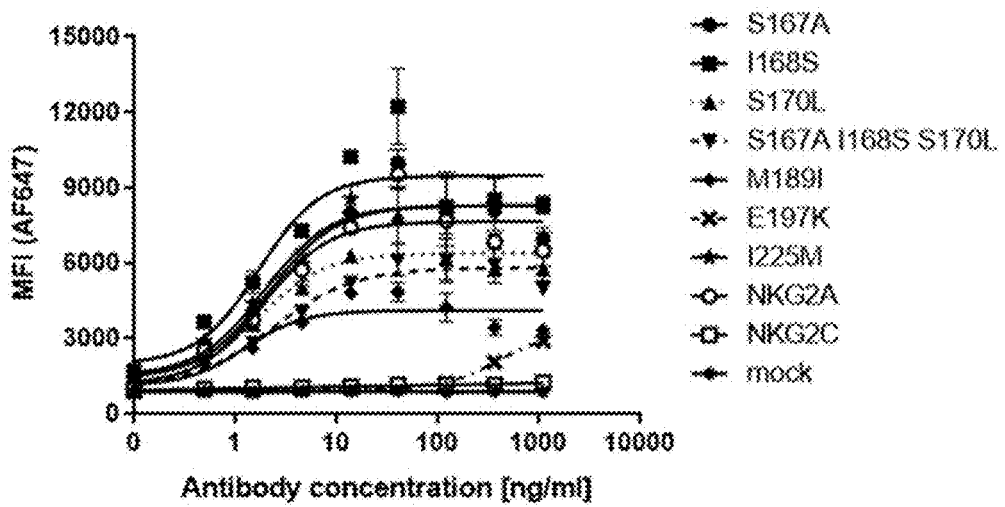
Figure 4:
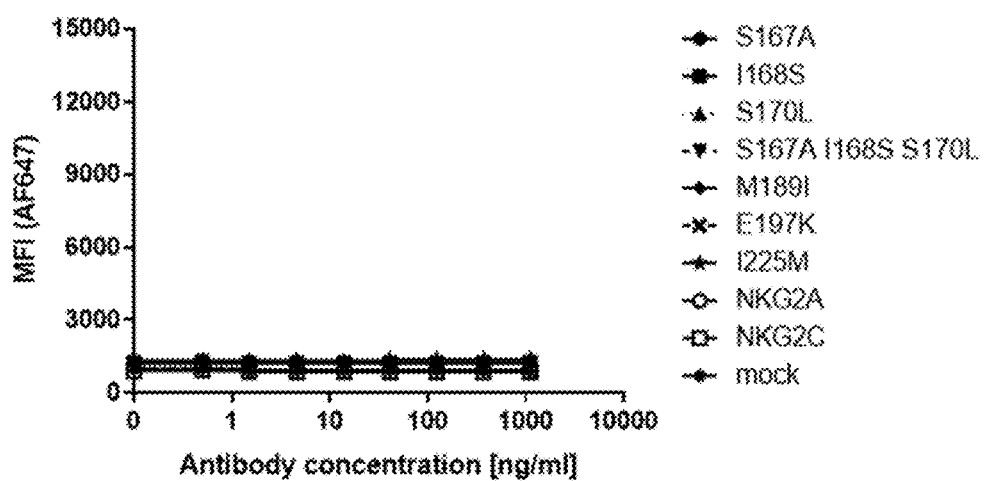

As shown in FIG. 4, four of the antibodies (23566, 23925, 24135, and 24208) showed reduced binding to the heterodimer with the NKG2A S170L substitution as well as to the heterodimer with the NKG2A triple substitution (S167A, I168S, S170L). This indicates that for those four antibodies, binding to human NKG2A is dependent on at least residue S170. The reduced binding for 23925 and 24208 was greater for the triple substitution than for the single S170L substitution, indicating an additional influence of the concurrent mutations S167A and I168S. Antibody 23765 and the monalizumab analogue showed reduced binding to the heterodimer with the NKG2A E197K substitution, demonstrating the need for glutamic acid at position 197 for proper binding of these two antibodies to human NKG2A. Monalizumab also showed reduced binding, to the heterodimer with the M189I substitution, indicating some influence of methionine at position 189.

Example 7. Screening of Anti-NKG2A Antibodies in NK Cell-Mediated Killing of K562-HLA-E Cells A panel of anti-NKG2A antibodies was evaluated for the ability to enhance the killing of K562 chronic myeloid leukemia cells transfected with HLA-E (K562-HLA-E) by the NK cell line NK-92, or by primary NK cells from a healthy donor.

Materials and Methods

K562-HLAE cells were HLA-B*0701 peptide-loaded and NK-92 cells were IL-2 starved overnight. The next day, NK cells were isolated from a healthy donor and anti-NKG2A antibodies were incubated at a concentration of 25 µg/mL with NK-92 or primary NK cells, followed by addition of calcein-loaded K562-HLA-E target cells and incubation for 90 minutes. The killing capacity of NK-92 or primary NK cells was measured by calcein release to the supernatant. Specific lysis was calculated by subtracting spontaneous lysis (calcein-loaded 562-HLA-E cells only) and normalizing to maximum lysis (Triton X-100 lysis of calcein-loaded K562-HLA-E cells).

Results

Figure 5:
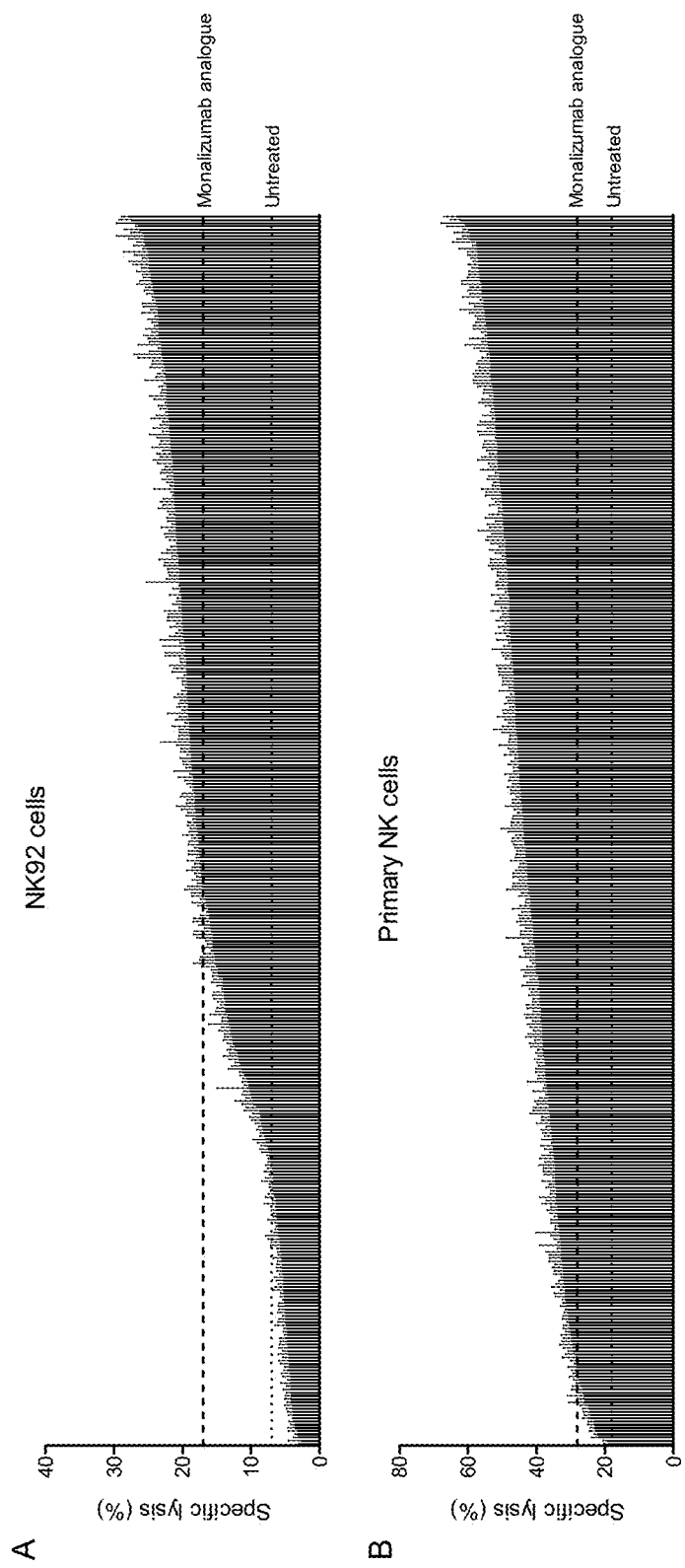
FIG. 5 is a set of graphs showing lysis of K562-HLA-E cells mediated by either NK92 cells (Panel A) or primary NK cells (Panel B) after incubation with a panel of anti-human NKG2A antibodies. Data are presented as mean±SEM, n=3. The correlation of data presented in Panels A and B is shown in Panel C. Dotted lines indicate levels of lysis in samples not treated with antibodies ("untreated") or treated with a monalizumab analogue.
Figure 5:
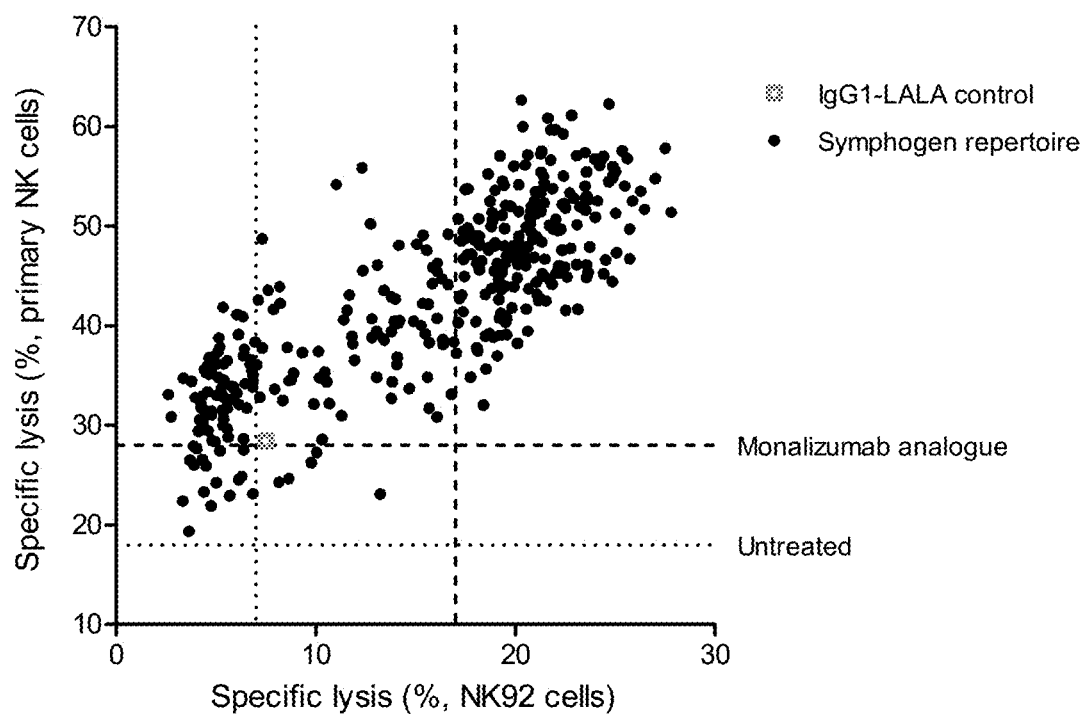

FIG. 5 shows specific lysis of K562-HLA-E cells after treatment with the panel of anti-NKG2A antibodies. It is evident that the level of lysis after treatment with the different anti-NKG2A antibodies varied strongly, showing that some antibodies had no functionality in this assay, whereas other antibodies strongly enhanced killing of K562-HLA-E cells and to a higher level than a monalizumab analogue (IgG4) (Panels A and B). A positive correlation was observed between the levels of killing using NK-92 and primary NK cells (Panel C).

Example 8. Functional Activity of Anti-Human NKG2A Antibodies in NK-92 Cell-Mediated Killing of K562-HLA-E Cells This example describes in vitro functional evaluation of several anti-NKG2A antibodies (24208, 23925, 23566, 23765, 23686) with the purpose of demonstrating dose-dependent antagonistic activity. The antibodies were evaluated for their ability to enhance NK-92 cell-mediated killing of K562 cells transfected with HLA-E (K562-HLA-E). A monalizumab analogue (IgG4) was included for comparison.

Materials and Methods

K562-HLA-E cells were HLA-B*0701 peptide-loaded and NK-92 cells were IL-2 starved overnight. The next day, NK-92 cells and anti-NKG2A antibodies were incubated with a two-fold titration of the indicated antibodies starting from 25 µg/m L, followed by addition of calcein-loaded K562-HLA-E target cells and incubation for 90 minutes. The killing capacity of NK-92 cells was measured by calcein release to the supernatant. Specific lysis was calculated by subtracting spontaneous lysis (calcein-loaded 562-HLAE cells only) and normalizing to maximum lysis (Triton X-100 lysis of calcein-loaded K562-HLAE cells).

Results

Figure 6:
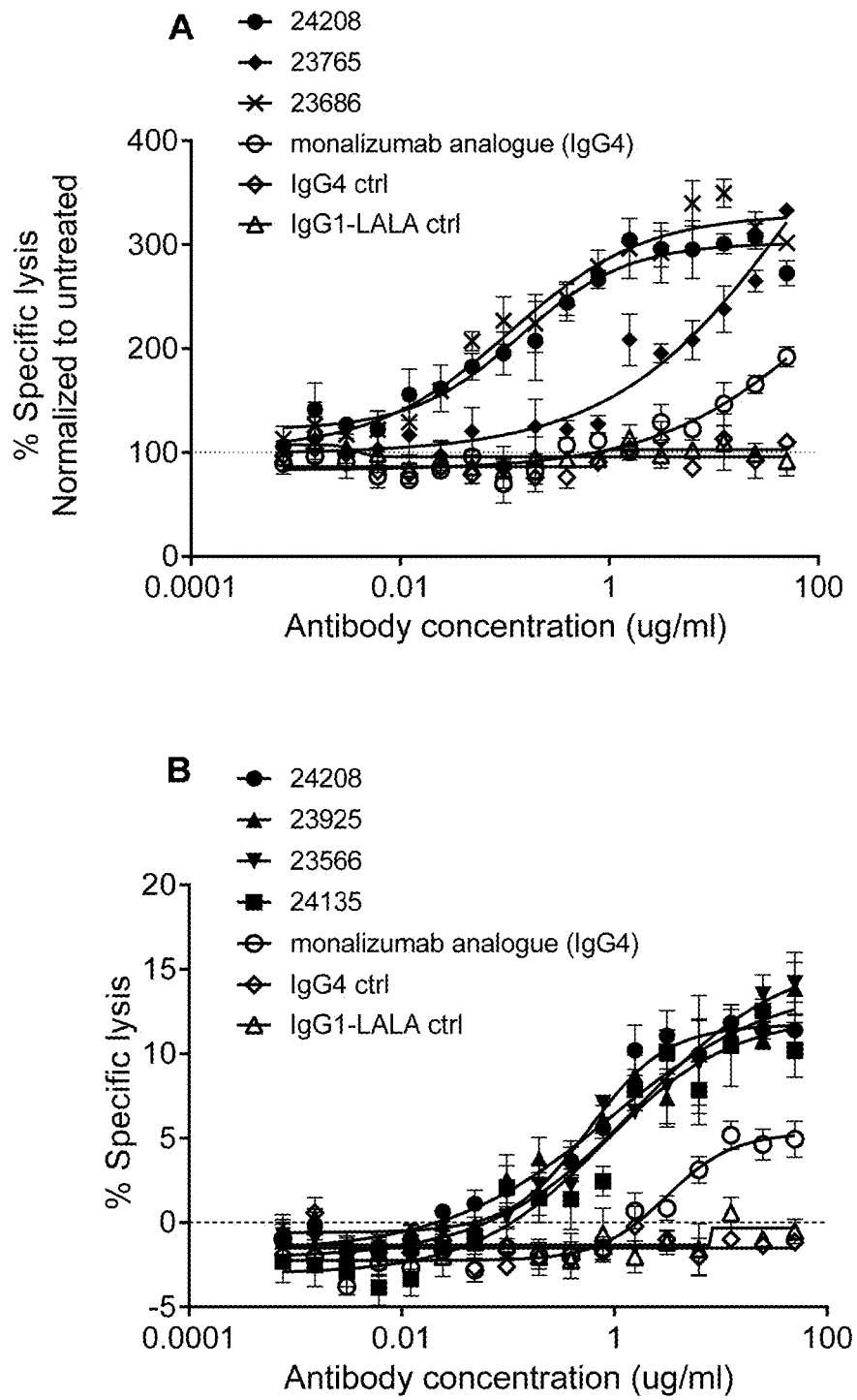
FIG. 6 is a pair of graphs showing lysis of K562-HLA-E cells mediated by NK-2 cells after incubation with the indicated anti-NKG2A mAbs, a reference antibody, an IgG$_4$ control ("ctrl") antibody, and an IgG$_1$-LALA control antibody. Data are normalized to untreated control in Panel A.

The killing of K562-HLA-E cells upon treatment with the anti-NKG2A antibodies is shown in FIG. 6. Several anti-NKG2A antibodies showed superior activity compared to the monalizumab analogue.

Example 9. Functional Activity of Anti-Human NKG2A Antibodies in Primary NK Cell-Mediated Killing of K562-HLA-E Cells This example describes in vitro functional evaluation of several anti-NKG2A antibodies (24208, 23925, 23566, 23765, 23686) with the purpose of demonstrating dose-dependent antagonistic activity. The antibodies were evaluated for their ability to enhance primary NK cell-mediated killing of K562 cells transfected with HLA-E (K562-HLA-E). A monalizumab analogue (IgG4) was included for comparison.

Materials and Methods

K562-HLA-E cells were HLA-B*0701 peptide-loaded and primary NK cells were isolated from fresh PBMCs from healthy donors. The next day, primary NK cells and anti-NKG2A antibodies were incubated with a two-fold titration of the indicated antibodies starting from 25 µg/mL, followed by addition of calcein-loaded K562-HLA-E target cells (1:10 E:T ratio) and incubation for 90 minutes. The killing capacity of primary NK cells was measured by calcein release to the supernatant. Specific lysis was calculated by subtracting spontaneous lysis (calcein-loaded 562-HLA-E cells only) and normalizing to maximum lysis (Triton X-100 lysis of calcein-loaded K562-HLA-E cells).

Results

Figure 7:
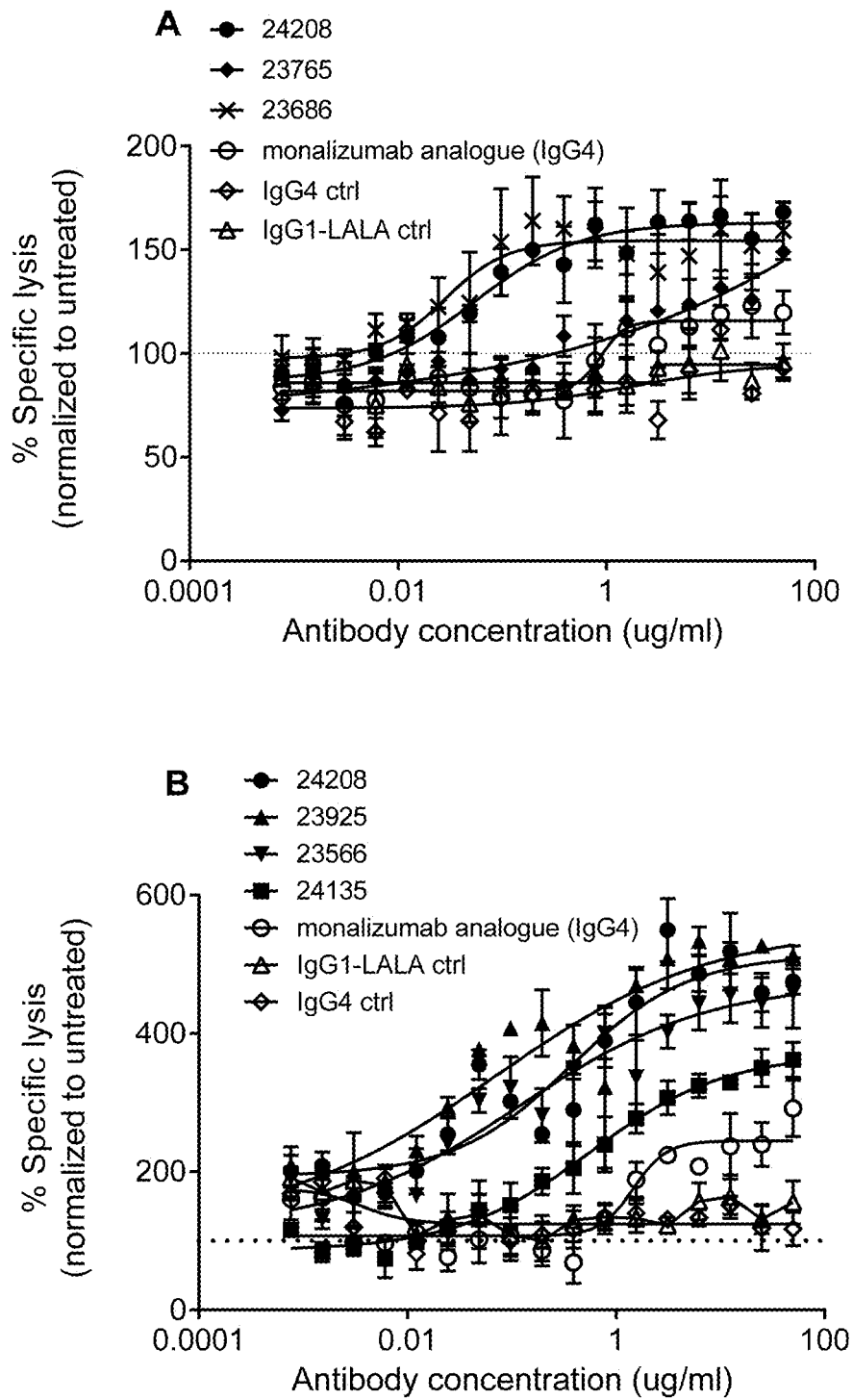
FIG. 7 is a pair of graphs showing lysis of K562-HLA-E cells mediated by primary NK cells after incubation with the indicated anti-NKG2A mAbs, a reference antibody, an IgG$_4$ control ("ctrl") antibody, and an IgG$_1$-LALA control antibody. Data are normalized to untreated control.

The killing of K562-HLA-E cells upon treatment with the anti-NKG2A antibodies is shown in FIG. 7. Several anti-NKG2A antibodies showed superior activity compared to the monalizumab analogue (IgG4).

Example 10. Functional Activity of Anti-Human NKG2A Antibodies in γδ T Cell-Mediated Killing of K562-HLA-E Cells This example describes in vitro functional evaluation of selected anti-NKG2A antibodies with the purpose of demonstrating dose-dependent antagonistic activity. The antibodies were evaluated for their ability to enhance γδ T cell mediated killing of K562 cells transfected with HLA-E (K562-HLA-E). A monalizumab analogue (IgG$_4$) was included for comparison.

Materials and Methods

K562-HLA-E cells were HLA-B*0701 peptide-loaded and NKG2A+γδ T cells were isolated. The next day, NKG2A+γδ T cells and anti-NKG2A antibodies were incubated with a two-fold titration of the indicated antibodies starting from 25 μg/m L, followed by addition of calcein-loaded K562-HLA-E target cells and incubation for 3 hours. The killing capacity of γδ T cells was measured by calcein release to the supernatant. Specific lysis was calculated by subtracting spontaneous lysis (calcein-loaded 562-HLA-E cells only) and normalizing to maximum lysis (Triton X-100 lysis of calcein-loaded K562-HLAE cells).

Results

Figure 8:
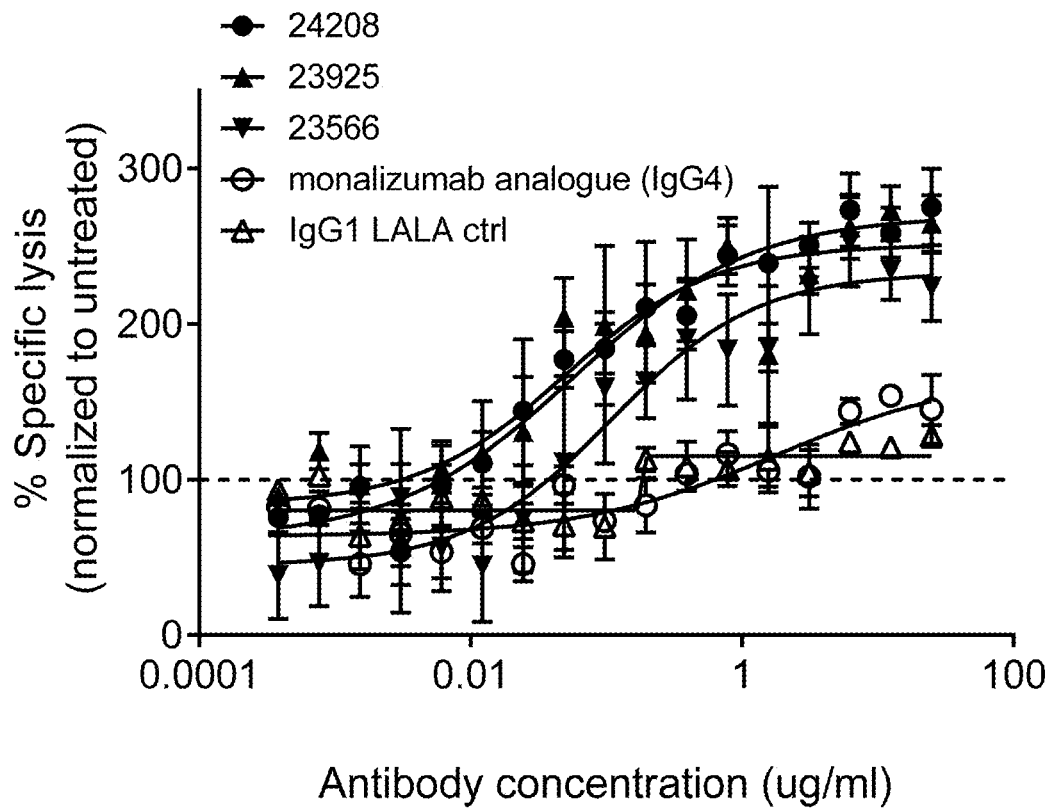
FIG. 8 is a graph showing lysis of K562-HLA-E cells mediated by γδ T cells after incubation with the indicated anti-NKG2A antibodies, a reference antibody, and a control antibody ("ctrl"). Data are normalized to untreated control.

The killing of K562-HLA-E cells upon treatment with the anti-NKG2A antibodies is shown in FIG. 8. Several anti-NKG2A antibodies showed superior activity to the monalizumab analogue.

Example 11. EC50 and Efficacy of Killing of Cancer Cells

This example describes in vitro functional evaluation of the anti-NKG2A antibody 24208 with the purpose of demonstrating cytotoxic activity. The antibodies were evaluated for their ability to enhance primary human NK cell-mediated killing of K562 cells transfected with HLA-E (K562-HLA-E). A monalizumab analogue (IgG$_4$) and two BMS analogues, BMS-NKG2A.9 (HC: SEQ ID NO: 65, LC: SEQ ID NO: 66) and BMS-NKG2A.11 (HC: SEQ ID NO: 65, LC: SEQ ID NO: 67), were included for comparison.

Material and Methods

K562-HLA-E cells were HLA-B*0701 peptide-loaded and primary human NK cells were IL2 starved overnight. The next day, primary human NK cells and anti-NKG2A antibodies were incubated with a two-fold titration of the indicated antibodies starting from 50 μg/mL followed by addition of calcein-loaded K562-HLA-E target cells and incubation for 90 minutes. The killing capacity of primary human NK cells was measured by calcein release to the supernatant. Specific lysis was calculated by subtracting spontaneous lysis (calcein-loaded 562-HLAE cells only) and normalizing to maximum lysis (Triton X-100 lysis of calcein-loaded K562-HLAE cells).

Results

Figure 9:
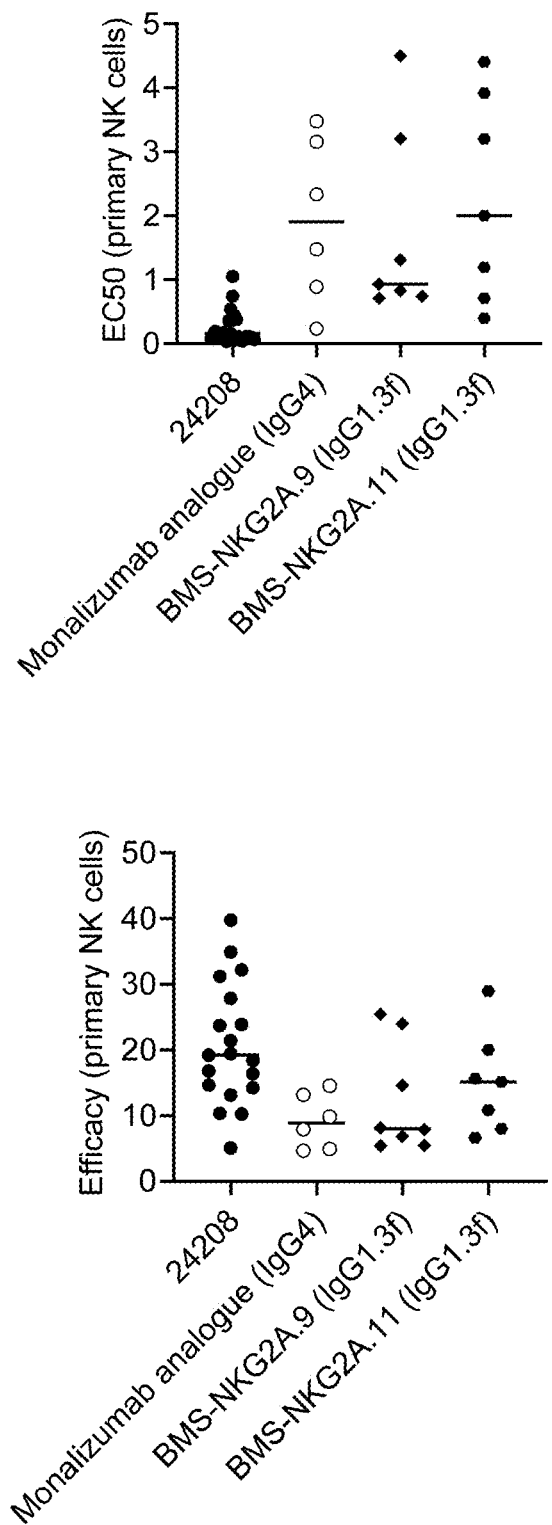
FIG. 9 is a pair of graphs showing EC50 (top) and efficacy (bottom) of primary human NK cell-mediated killing of K562-HLA-E cancer cells after incubation with the indicated anti-NKG2A antibodies. EC50 values as well as efficacy data were extracted from NK cell killing assays and summarized for comparison.

The killing of K562-HLA-E cells after treatment with the anti-NKG2A antibodies is shown in Table 8 and in FIG. 9. The 24208 anti-NKG2A antibody showed superior activity compared to the monalizumab analogue and the BMS-NKG2A.9 and BMS-NKG2A.11 analogues.

TABLE 8

Summary of induced NK cell cytotoxicity (EC50)

| EC50 (μg/mL) | 24208 (IgG$_1$ LALA) (n = 19) | Monalizumab (IgG$_4$) (n = 6) | BMS NKG2A.9 (IgG$_1$3f) (n = 7) | BMS NKG2A.11 (IgG$_1$3f) (n = 6) |
|---|---|---|---|---|
| Median | 0.19 | 0.89 | 1.07 | 0.71 |
| Range | 0.04-1.05 | 0.24-3.16 | 0.71-4.50 | 0.40-4.41 |

Example 12. NK Cell-Mediated Killing Induced by 24208 in Selected Cell Lines Expressing Endogenous HLA-E This example describes the expression of endogenous HLA-E on the surface of tumor cell lines (HT-29, CCRF-CEM, A253, Detroit 562, CAL-120, FaDu) and the effect of 24208 on NK cell-mediated killing of these tumor cell lines in vitro.

Materials and Methods

The expression of endogenous HLA-E in six different cell lines (HT-29, CCRF-CEM, A253, Detroit 562, CAL-120, and FaDu) was investigated by flow cytometry. Isolated human primary NK cells from healthy individuals were co-cultured with six different calcein-labeled target cells expressing endogenous HLA-E (loaded with HLA-B*0701 peptide) in a 10:1 ratio and treated with a single concentration of 24208 or isotype control (IgG$_1$ LALA). Release of calcein was measured after 1.5 hours and percentage specific lysis was calculated.

Results

Figure 10:
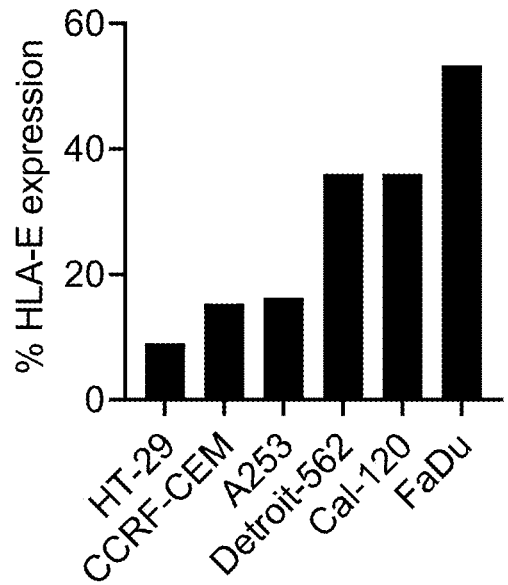
FIG. 10 is a pair of graphs showing the expression of endogenous HLA-E at the surface of six different tumor cell lines (Panel A) and the effect of antibody 24208 on NK-mediated killing of these six tumor cell lines (Panel B).
Figure 10:
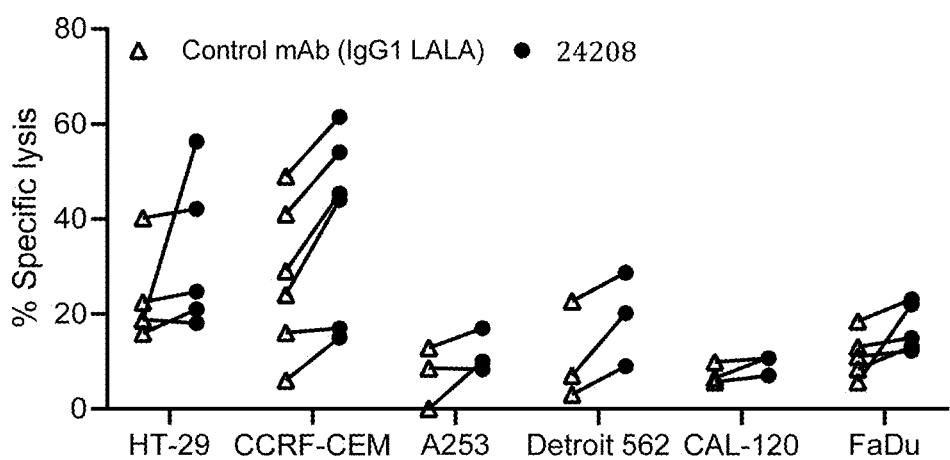

All six human tumor cell lines were shown to express endogenous HLA-E on the surface (FIG. 10, Panel A). Treatment with 24208 induced NK-mediated killing of these tumor cell lines compared to IgG$_1$ LALA treatment (FIG. 10, Panel B).

Example 13. MIP-1β Release in NK-Cancer Cell Co-Cultures

This example describes in vitro functional evaluation of the anti-NKG2A antibody 24208 with the purpose of demonstrating cytotoxic activity. The antibodies were evaluated for their ability to induce secretion of the pro-inflammatory cytokine Macrophage-inflammatory protein-1β (MIP-1β) upon co-culture of primary human NKG2A+NK cells with either of the cancer cell lines A549 and JIMT-1.

Material and Methods

Primary human NKG2A+NK cells were incubated with a two-fold titration of 24208 or IgG$_1$ LALA (starting from 50 μg/mL) and cultured with stable HLA-E expressing cancer cells transduced with the HLAE-trimer. After 48 hours of co-culture, MIP-1β concentrations in the co-culture supernatants were measured by ELISA.

Results

Figure 11:
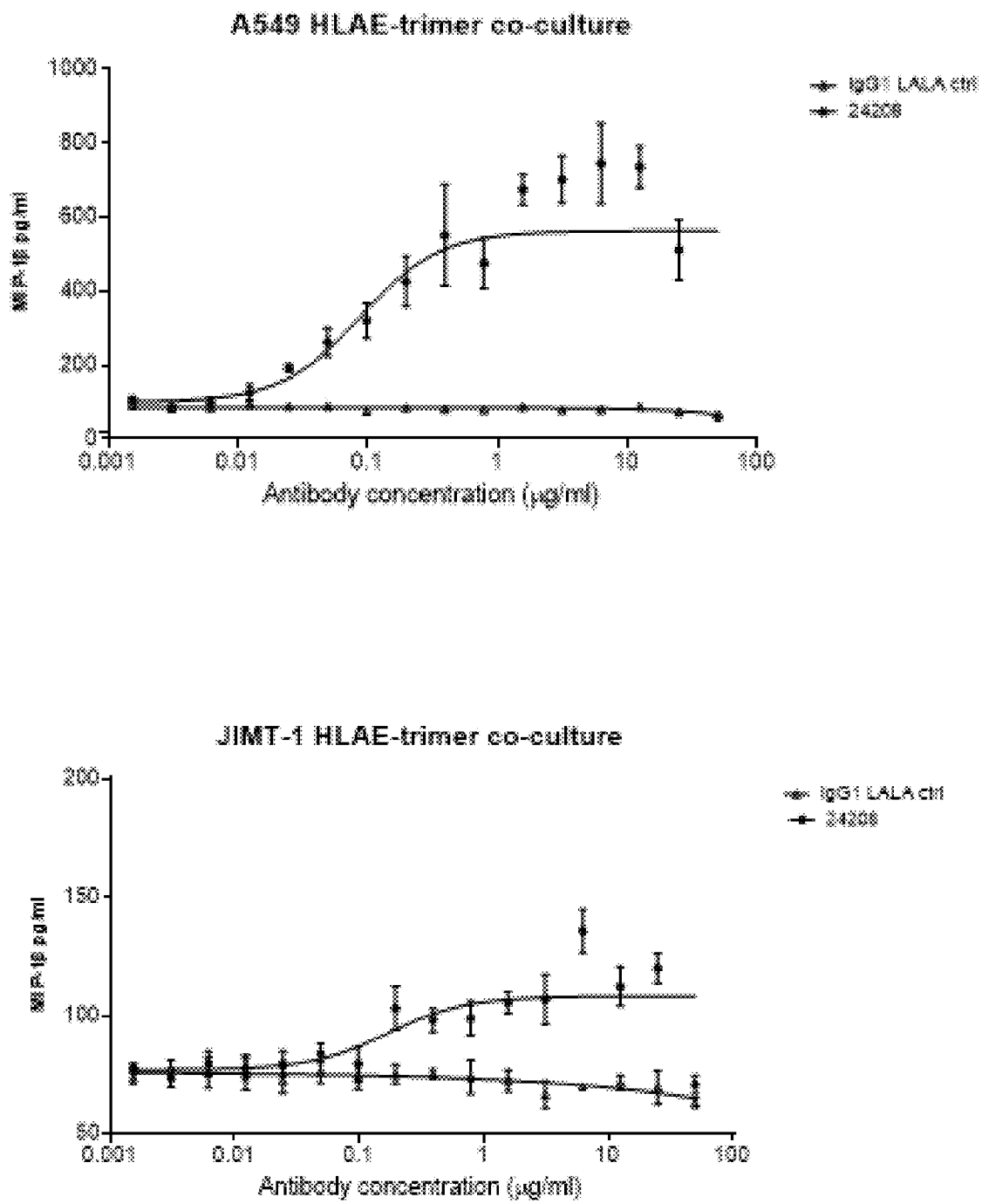
FIG. 11 is a pair of graphs showing the concentration of MIP-1β upon co-culture of A549 HLAE-trimer cells (top) or JIMT-1 HLAE-trimer cells (bottom) with primary human NK cells treated with antibody 24208 or IgG$_1$ LALA.

The concentration of MIP-1β in the co-culture supernatants upon co-culture of A549 HLAE-trimer cells or JIMT-1 HLAE-trimer cells with primary human NK cells treated with 24208 or IgG$_1$ LALA is shown in FIG. 11. The 24208 anti-NKG2A antibody showed superior induction of MIP-1β compared to the IgG$_1$ LALA control antibody.

The invention claimed is:

1. An anti-NKG2A antibody or an antigen-binding portion thereof, wherein said antibody comprises H-CDR1-3 and L-CDR1-3 amino acid sequences of:
   a) SEQ ID NOs: 5-10, respectively;
   b) SEQ ID NOs: 15-20, respectively;
   c) SEQ ID NOs: 25-30, respectively;
   d) SEQ ID NOs: 35-40, respectively;
   e) SEQ ID NOs: 45-50, respectively; or
   f) SEQ ID NOs: 55-60, respectively.

2. The antibody or antigen-binding portion of claim 1, wherein said antibody comprises a heavy chain variable domain and a light chain variable domain comprising the amino acid sequences of:
   a) SEQ ID NOs: 3 and 4, respectively;
   b) SEQ ID NOs: 13 and 14, respectively;
   c) SEQ ID NOs: 23 and 24, respectively;
   d) SEQ ID NOs: 33 and 34, respectively;
   e) SEQ ID NOs: 43 and 44, respectively; or
   f) SEQ ID NOs: 53 and 54, respectively.

3. The anti-NKG2A antibody or antigen-binding portion of claim 1, wherein the antibody or antigen-binding portion has at least one property selected from:
   a) binds to human NGK2A with a $K_D$ of 15 nM or less as measured by surface plasmon resonance;
   b) binds to human NKG2A expressed on CHO-S cells;
   c) blocks binding of HLA-E to human NKG2A/CD94 heterodimer expressed on CHO-S cells;

d) enhances NK-92 cell-mediated killing of K562 cells transfected with HLA-E;
e) enhances primary NK cell-mediated killing of K562 cells transfected with HLA-E;
f) enhances γδ T cell-mediated killing of K562 cells transfected with HLA-E; and
g) binds to a different epitope on human NKG2A than monalizumab.

4. An anti-NKG2A antibody that comprises:
a) a heavy chain (HC) comprising the amino acid sequences of SEQ ID NOs: 3 and 61 and a light chain (LC) comprising the amino acid sequences of SEQ ID NOs: 4 and 62;
b) an HC comprising the amino acid sequences of SEQ ID NOs: 13 and 61 and an LC comprising the amino acid sequences of SEQ ID NOs: 14 and 62;
c) an HC comprising the amino acid sequences of SEQ ID NOs: 23 and 61 and an LC comprising the amino acid sequences of SEQ ID NOs: 24 and 62;
d) an HC comprising the amino acid sequences of SEQ ID NOs: 33 and 61 and an LC comprising the amino acid sequences of SEQ ID NOs: 34 and 62;
e) an HC comprising the amino acid sequences of SEQ ID NOs: 43 and 61 and an LC comprising the amino acid sequences of SEQ ID NOs: 44 and 62; or
f) an HC comprising the amino acid sequences of SEQ ID NOs: 53 and 61 and an LC comprising the amino acid sequences of SEQ ID NOs: 54 and 62.

5. A pharmaceutical composition comprising the anti-NKG2A antibody or antigen-binding portion of claim 1 and a pharmaceutically acceptable excipient.

6. The pharmaceutical composition of claim 5, further comprising an immunostimulatory agent, a vaccine, a chemotherapeutic agent, an anti-neoplastic agent, an anti-angiogenic agent, or a tyrosine kinase inhibitor.

7. A bi-specific binding molecule comprising the antigen-binding domain of an anti-NKG2A antibody according to claim 1 and the antigen-binding domain of another, distinct antibody.

8. A method of using the anti-NKG2A antibody or antigen-binding portion of claim 1 in a diagnostic process comprising: (a) contacting a patient sample with said antibody or antigen-binding portion; and (b) detecting and/or measuring the level of NKG2A.

9. A method for enhancing immune activity in a human patient in need thereof, comprising administering to said patient a therapeutically effective amount of the anti-NKG2A antibody or antigen-binding portion of claim 1.

10. A method for treating cancer in a human patient in need thereof, comprising administering to said patient a therapeutically effective amount of the anti-NKG2A antibody or antigen-binding portion of claim 1.

11. The method of claim 10, wherein the cancer is:
a) in a tissue selected from the group consisting of skin, lung, intestine, colon, ovary, brain, prostate, kidney, soft tissues, the hematopoietic system, head and neck, liver, bone, bladder, breast, stomach, uterus, cervix, and pancreas; or
b) head and neck cancer, breast cancer, colorectal cancer, lung cancer, esophageal cancer, acute myeloid leukemia, acute lymphoblastic leukemia, a myelodysplastic syndrome, multiple myeloma, chronic lymphoid leukemia, chronic myeloid leukemia, myeloproliferative neoplasm, Hodgkin's lymphoma, or non-Hodgkin's lymphoma.

12. The method of claim 9, further comprising administering to the patient an immunostimulatory agent, a vaccine, a chemotherapeutic agent, an anti-neoplastic agent, an anti-angiogenic agent, a tyrosine kinase inhibitor, or radiation therapy.

13. A method for treating an immune disorder in a human patient in need thereof, comprising administering to said patient a therapeutically effective amount of the anti-NKG2A antibody or antigen-binding portion of claim 1.

14. An anti-NKG2A antibody that comprises a heavy chain (HC) comprising the amino acid sequences of SEQ ID NOs: 3 and 61 and a light chain (LC) comprising the amino acid sequences of SEQ ID NOs: 4 and 62.

15. A pharmaceutical composition comprising the anti-NKG2A antibody of claim 14 and a pharmaceutically acceptable excipient.

16. A method of using the anti-NKG2A antibody or antigen-binding portion of claim 14 in a diagnostic process comprising: (a) contacting a patient sample with said antibody or antigen-binding portion; and (b) detecting and/or measuring the level of NKG2A.

17. A method for enhancing immune activity in a human patient in need thereof, comprising administering to said patient a therapeutically effective amount of the anti-NKG2A antibody of claim 14.

18. The method of claim 17, further comprising administering to the patient an immunostimulatory agent, a vaccine, a chemotherapeutic agent, an anti-neoplastic agent, an anti-angiogenic agent, a tyrosine kinase inhibitor, or radiation therapy.

19. A method for treating cancer in a human patient in need thereof, comprising administering to said patient a therapeutically effective amount of the anti-NKG2A antibody of claim 14.

20. A method for treating an immune disorder in a human patient in need thereof, comprising administering to said patient a therapeutically effective amount of the anti-NKG2A antibody of claim 14.

* * * * *

SEQUENCE LISTING

<160> NUMBER OF SEQ ID NOS: 67

<210> SEQ ID NO 1
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggtgcagc tggtcgagag cggaggagga ctggtgaagc caggtggaag tctgcgactg      60
tcatgcgccg cttccggatt caccttttct gactactata tgaggtggat ccggcaggcc     120
cctggaaaag gctggaatg gtgtcacac atctccacta gcggctctac catctactat       180
gctgactccg tcaagggcag attcacaatt agccgcgata acgcaaaaaa ttctctgtac     240
ctgcaaatga acagtctgcg cgcagaggac actgccgtgt actattgcgc cagggaccat     300
tactatagtc gtggagtgat cgggtattgg ggtcagggca ccctggtcac agtctcg       357

<210> SEQ ID NO 2
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gacatccaga tgacccagtc cccttccagc gttagtgctt cagtcggaga tagggtgacc      60
atcacatgcc gggcttccca ggggattct agttggctgg catggtacca gcagaagccc     120
ggaaaagccc ctaagctgct gatctatgcc gcttcatccc tgcaaagtgg cgtcccatct     180
agattctccg gcagcggatc tgggaccgac tttactctga ccattagttc tctgcagcca     240
gaggatttcg caacatacta ttgtcagcag gccaacagct tcccctacac atttggtcag     300
ggcactaaac tggaaattaa g                                                321

<210> SEQ ID NO 3
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Arg Trp Ile Arg Gln Ala Pro Gly Lys Gly Leu Glu Trp Val
        35                  40                  45

Ser His Ile Ser Thr Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp His Tyr Tyr Ser Arg Gly Val Ile Gly Tyr Trp Gly Gln
            100                 105                 110

Gly Thr Leu Val Thr Val Ser Ser
            115                 120

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
            100                 105

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Thr Phe Ser Asp Tyr Tyr
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Ser Thr Ser Gly Ser Thr Ile
1               5

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Ala Arg Asp His Tyr Tyr Ser Arg Gly Val Ile Gly Tyr Trp
1               5                   10                  15

```
<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gly Ile Ser Ser Trp
1               5

<210> SEQ ID NO 9
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Ser
1

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Gln Gln Ala Asn Ser Phe Pro Tyr Thr Phe
1               5                   10

<210> SEQ ID NO 11
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaggtgcagc tggtcgaaag tggaggagga ctggtgaagc caggtggatc tctgagactg      60
agttgcgccg cttcagggtt cacattttct tgctgtcgca tgaactgggt gcggcaggca     120
cctggaaaag gactggagtg ggtctccagc atctcttctt catcctctta catctactat     180
gctgactccg tgaagggaag attcactatc tcccgcgata acgcaaaaaa tagcctgtat     240
ctgcagatga actctctgcg agcagaagac accgccgtct actattgtgc tagggatggc     300
tggaatgacg tgtttgatta ctggggtcag ggcaccctgg tcacagtctc g              351

<210> SEQ ID NO 12
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gagatcgtgc tgactcagag cccagcaacc ctgtcactgt cccccggaga aagggcaacc      60
ctgtcttgcc gggccagcca gtctgtctcc tcttacctgg cttggtatca gcaaaagccc     120
```

```
gggcaggcac ctcgactgct gatctacgac gccagtaaca gagctaccgg aattcccgcc      180
cgcttcagtg gttcaggctc cggaacagac tttacccctga caatctctag tctggagcct     240
gaagatttcg ccgtgtacta ttgtcagcag aggtctaatt ggccactgac atttggcgga     300
gggactaagg tcgagatcaa g                                                 321
```

```
<210> SEQ ID NO 13
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Cys Cys
            20                  25                  30

Arg Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Trp Asn Asp Val Phe Asp Tyr Trp Gly Gln Gly Thr
            100                 105                 110

Leu Val Thr Val Ser Ser
        115

```
<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

```
<210> SEQ ID NO 15
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 15

Gly Phe Thr Phe Ser Cys Cys Arg
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile Ser Ser Ser Ser Ser Tyr Ile
1               5

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Ala Arg Asp Gly Trp Asn Asp Val Phe Asp Tyr Trp
1               5                   10

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ser Val Ser Ser Tyr
1               5

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Ala Ser
1

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Gln Gln Arg Ser Asn Trp Pro Leu Thr Phe
1               5                   10
```

<210> SEQ ID NO 21
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gaggtgcagc tggtcgaaag tggaggagga ctggtgaagc caggtggatc actgcgactg      60
tcctgcgccg cctccggctt cacatttttcc tcttactcta tgaactgggt taggcaggcc    120
cctggaaaag gctggagtg gtctctagt atctcatcca gctctagtta catctactat      180
gctgactctg tgaagggcag gttcactatc tctcgggata cgcaaaaaa tagtctgtat     240 ctgcagatga attcactgag agcagaggac accgccgtgt actattgtgc tcgcgacgaa    300
tggggactgc tggggtttga ttcctggggt cagggcaccc tggtcacagt ctcg          354

<210> SEQ ID NO 22
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gagatcgtgc tgactcagtc tcctgcaacc ctgtctctga gtcccggcga aagggcaact      60
ctgtcctgcc gggcctcaca gtccatttct aactacctgg cttggtatca gcaaaagcca    120
ggacaggcac cccgactgct gatctacgac gcctccaata gagctaccgg cattcccgcc    180
cgcttctctg gctctggatc agggacagac ttcaccctga caatctccag cctggagcct    240
gaagacttcg ccgtgtacta ttgtcagcag aggacagatt ggccccttg gacatttggt     300 cagggcacta aggtcgagat caag                                           324

<210> SEQ ID NO 23
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Trp Gly Leu Leu Gly Phe Asp Ser Trp Gly Gln Gly
            100                 105                 110

```
Thr Leu Val Thr Val Ser Ser
        115
```

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Thr Asp Trp Pro Pro
                85                  90                  95

Trp Thr Phe Gly Gln Gly Thr Lys Val Glu Ile Lys
            100                 105
```

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Gly Phe Thr Phe Ser Ser Tyr Ser
1               5
```

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Ile Ser Ser Ser Ser Ser Tyr Ile
1               5
```

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Cys Ala Arg Asp Glu Trp Gly Leu Leu Gly Phe Asp Ser Trp
1               5                   10
```

<210> SEQ ID NO 28

<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ser Ile Ser Asn Tyr
1               5

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Ala Ser
1

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Gln Gln Arg Thr Asp Trp Pro Pro Trp Thr Phe
1               5                   10

<210> SEQ ID NO 31
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gaggtgcagc tgctggaaag cggaggagac ctggtccagc caggaggttc cctgcgactg     60
agctgcgccg cttctggctt cacttttgat aactacgcca tgcactgggt gaggcaggct    120
cctgggaagg gtctggagtg ggtctccact atcaccaata gcggcggaac cacatactat    180
gcagactctg tgaaggggag gttcaccctg agtcgggata actcaaaaaa tacactgtac    240
ctgcagatga acagtctgag agctgaagac acagcagtgt actattgtgc aaaagcccat    300
tactatgctc gcggctattt cgattttttgg ggccagggaa cactggtcac tgtctcg     357

<210> SEQ ID NO 32
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gacatccaga tgacccagac accttccagc gttagtgctt cagtcggaga tagggtgact     60
atcacctgcc gggcttccca ggggattttct agttggctgg catggtacca gcagaagccc    120
ggaaaagccc ctaagctgct gatctatgcc gcttcatccc tgcaaagtgg cgtcccatct    180

```
agattctccg gcagcggatc tgggactgac tttacactga ctattagctc tctgcagcca    240
gaggatttcg caacatacta ttgtcagcag gccaactcct tccccctacac ctttggtcag   300 ggcacaaaac tggaaattaa g                                              321
```

<210> SEQ ID NO 33
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Asp Asn Tyr
            20                  25                  30

Ala Met His Trp Val Arg Gln Ala Pro Gly Lys Gly Leu Glu Trp Val
        35                  40                  45

Ser Thr Ile Thr Asn Ser Gly Gly Thr Thr Tyr Tyr Ala Asp Ser Val
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Tyr Tyr Ala Arg Gly Tyr Phe Asp Phe Trp Gly Gln
            100                 105                 110

Gly Thr Leu Val Thr Val Ser Ser
        115                 120
```

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Asp Ile Gln Met Thr Gln Thr Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
            100                 105
```

<210> SEQ ID NO 35
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 35

Gly Phe Thr Phe Asp Asn Tyr Ala
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Thr Asn Ser Gly Gly Thr Thr
1               5

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Cys Ala Lys Ala His Tyr Tyr Ala Arg Gly Tyr Phe Asp Phe Trp
1               5                   10                  15

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Gly Ile Ser Ser Trp
1               5

<210> SEQ ID NO 39
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Ala Ser
1

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Gln Gln Ala Asn Ser Phe Pro Tyr Thr Phe
1               5                   10
```

<210> SEQ ID NO 41
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
gaggtgcagc tggtcgaatc cggaggagga ctggtgcagc caggtggatc actgcgactg    60
tcctgcgccg cctccggatt cacctttcc agttacgcca tgaactgggt taggcaggct   120
cctggcaagg gactggagtg gtctcaaca atctctaata gtggagggac cacatactat   180
gcagactctg tgaagggcag gttcacaatt tctcgggaca cagtaaaga tactctgtat   240
ctgcaaatga attccctgag agctgaagac accgcagtgt actattgtgc aaaagcccac   300
tactatgctc gcggctactt tgattattgg ggacagggga ctctggtcac cgtctcg     357
```

<210> SEQ ID NO 42
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42

```
gacatccaga tgacccagag cccctccagc gttagtgctt cagtcggaga tagggtgacc    60
atcacatgcc gggctagtca ggggatttct agttggctgg catggtacca gcagaagtct   120
ggaaaagccc ccaagctgct gatctatgcc gcttcatccc tgcaaattgg cgtcccttcc   180
cgattctccg gcagcggatc tgggaccgac tttactctga ccatcagctc tctgcagcca   240
gaggatttcg caacatacta ttgtcagcag gccaactcct tcccctacac atttggtcag   300
ggcactaaac tggaaattaa g                                             321
```

<210> SEQ ID NO 43
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Asn Ser Gly Gly Thr Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Tyr Tyr Ala Arg Gly Tyr Phe Asp Tyr Trp Gly Gln
            100                 105                 110

Gly Thr Leu Val Thr Val Ser Ser
        115                 120
```

```
                115                 120

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Ser Gly Lys Ala Pro Lys Leu Leu Ile
        35                  40                  45

Tyr Ala Ala Ser Ser Leu Gln Ile Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
            100                 105

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Phe Thr Phe Ser Ser Tyr Ala
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Ser Asn Ser Gly Gly Thr Thr
1               5

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys Ala Lys Ala His Tyr Tyr Ala Arg Gly Tyr Phe Asp Tyr Trp
1               5                   10                  15

<210> SEQ ID NO 48
<211> LENGTH: 6
```

```
<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Gly Ile Ser Ser Trp
1               5

<210> SEQ ID NO 49
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Ala Ser
1

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Cys Gln Gln Ala Asn Ser Phe Pro Tyr Thr Phe
1               5                   10

<210> SEQ ID NO 51
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
caggtgcagc tgcaggagag cgggccaggt ctggtgaagc cctctgaaac actgagtctg      60
acatgcactg ttagtggcgg atcagtctcc agcggccact actattggtc ttggattaga    120
caaccccctg gcaagggact ggagtggatc ggctatatct actattcagg atccaccaca    180 tacaacccctt ccctgaaaag ccgggtgagc atttctgtcg acacttcaaa gcatcagttc   240
agtctgaaac tgtctagtgt gaccgccgct gatacagctg tctactattg tgcaagatgg    300
gccgggtcct atcagccata ctattactat tacggcatgg acgtgtgggg gcagggtact    360
accgtcaccg tctcg                                                     375

<210> SEQ ID NO 52
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
gacatccaga tgacccagag tccttccagc ctgtcagcat ccgtgggcga cagagtcacc      60
atcacatgcc aggcctcaca ggatatttcc aactacctga attggtatca gcagaagccc    120
```

```
gggaaagccc ctaagctgct gatctacgac gcctccaacc tggagagggg agtgccatct    180
cggttcagcg gttctggcag tggaaccgat ttcacttta ccatctcttc tctgcaacca    240
gaggacattg ctacatacta ctgtcagcag tacgataact tccccctgac atttggcgga    300
gggactaaag tcgaaatcaa g                                             321
```

```
<210> SEQ ID NO 53
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

His Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Thr Tyr Asn Pro Ser
    50                  55                  60

Leu Lys Ser Arg Val Ser Ile Ser Val Asp Thr Ser Lys His Gln Phe
65                  70                  75                  80

Ser Leu Lys Leu Ser Ser Val Thr Ala Ala Asp Thr Ala Val Tyr Tyr
                85                  90                  95

Cys Ala Arg Trp Ala Gly Ser Tyr Gln Pro Tyr Tyr Tyr Tyr Gly
            100                 105                 110

Met Asp Val Trp Gly Gln Gly Thr Thr Val Thr Val Ser Ser
        115                 120                 125

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Arg Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Phe Pro Leu
                85                  90                  95

Thr Phe Gly Gly Gly Thr Lys Val Glu Ile Lys
            100                 105

<210> SEQ ID NO 55
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 55

Gly Gly Ser Val Ser Ser Gly His Tyr Tyr
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Tyr Tyr Ser Gly Ser Thr
1               5

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Cys Ala Arg Trp Ala Gly Ser Tyr Gln Pro Tyr Tyr Tyr Tyr Gly
1               5                   10                  15

Met Asp Val Trp
            20

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Asp Ile Ser Asn Tyr
1               5

<210> SEQ ID NO 59
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Ala Ser
1

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60
```

```
Cys Gln Gln Tyr Asp Asn Phe Pro Leu Thr Phe
1               5                   10
```

<210> SEQ ID NO 61
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 63
<211> LENGTH: 233
<212> TYPE: PRT
<213> ORGANISM: Homo sapiens

<400> SEQUENCE: 63

Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Asn Ser Ile Leu
            20                  25                  30

Ala Thr Glu Gln Glu Ile Thr Tyr Ala Glu Leu Asn Leu Gln Lys Ala
        35                  40                  45

Ser Gln Asp Phe Gln Gly Asn Asp Lys Thr Tyr His Cys Lys Asp Leu
    50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Thr
                85                  90                  95

Leu Ile Gln Arg His Asn Asn Ser Ser Leu Asn Thr Arg Thr Gln Lys
            100                 105                 110

Ala Arg His Cys Gly His Cys Pro Glu Glu Trp Ile Thr Tyr Ser Asn
        115                 120                 125

Ser Cys Tyr Tyr Ile Gly Lys Glu Arg Arg Thr Trp Glu Glu Ser Leu
    130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ile Ser Pro Ser Ser Trp Ile Gly
                165                 170                 175

Val Phe Arg Asn Ser Ser His His Pro Trp Val Thr Met Asn Gly Leu
            180                 185                 190

Ala Phe Lys His Glu Ile Lys Asp Ser Asp Asn Ala Glu Leu Asn Cys
        195                 200                 205

Ala Val Leu Gln Val Asn Arg Leu Lys Ser Ala Gln Cys Gly Ser Ser
```

```
              210                 215                 220
Ile Ile Tyr His Cys Lys His Lys Leu
225                 230

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gly Gly Gly Ser Gly Gly Gly Gly Ser Gly Gly Gly Gly Ser
1               5                   10                  15

<210> SEQ ID NO 65
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser His
                20                  25                  30

Ser Met Asn Trp Val Arg Gln Ala Pro Gly Lys Gly Leu Glu Trp Val
            35                  40                  45

Ser Ala Ile Ser Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Ala Glu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
```

```
                    260                 265                 270
Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 66
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 67
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Pro Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```